US00RE47636E

(19) United States
(12) Reissued Patent
Vintonyak et al.

(10) Patent Number: US RE47,636 E
(45) Date of Reissued Patent: Oct. 8, 2019

(54) SUBSTITUTED SPIROCYCLES

(71) Applicant: Boehringer Ingelheim International GmbH, Ingelheim am Rhein (DE)

(72) Inventors: Viktor Vintonyak, Warthausen (DE); Matthias Grauert, Biberach an der Riss (DE); Marc Grundl, Biberach an der Riss (DE); Alexander Pautsch, Biberach an der Riss (DE)

(73) Assignee: Boehringer Ingelheim International GmbH, Ingelheim am Rhein (DE)

(21) Appl. No.: 15/827,433

(22) Filed: Nov. 30, 2017

Related U.S. Patent Documents

Reissue of:
(64) Patent No.: 9,540,373
Issued: Jan. 10, 2017
Appl. No.: 14/849,710
Filed: Sep. 10, 2015

(30) Foreign Application Priority Data

Sep. 12, 2014 (EP) ..... 14184613

(51) Int. Cl.

| | |
|---|---|
| ***C07D 215/00*** | (2006.01) |
| ***A61K 45/06*** | (2006.01) |
| ***C07D 519/00*** | (2006.01) |
| ***C07D 471/10*** | (2006.01) |
| ***C07D 491/10*** | (2006.01) |
| ***A61K 31/47*** | (2006.01) |
| ***C07D 471/08*** | (2006.01) |
| ***C07D 491/20*** | (2006.01) |
| ***C07D 401/12*** | (2006.01) |
| ***A61K 31/438*** | (2006.01) |
| ***A61K 31/4355*** | (2006.01) |
| ***A61K 31/435*** | (2006.01) |
| ***C07D 491/107*** | (2006.01) |
| ***C07D 487/10*** | (2006.01) |

(52) U.S. Cl.
CPC ..... *C07D 491/20* (2013.01); *A61K 31/435* (2013.01); *A61K 31/438* (2013.01); *A61K 31/4355* (2013.01); *A61K 45/06* (2013.01); *C07D 401/12* (2013.01); *C07D 471/08* (2013.01); *C07D 471/10* (2013.01); *C07D 487/10* (2013.01); *C07D 491/10* (2013.01); *C07D 491/107* (2013.01); *C07D 519/00* (2013.01)

(58) Field of Classification Search
CPC .. C07D 491/20; C07D 401/12; C07D 487/10; C07D 491/107; C07D 471/08; C07D 471/10; C07D 491/10; C07D 519/00; A61K 31/438; A61K 31/435; A61K 31/4355; A61K 45/06
See application file for complete search history.

(56) References Cited

U.S. PATENT DOCUMENTS

| | | | |
|---|---|---|---|
| 4,125,727 | A | 11/1978 | Los |
| 7,012,075 | B2 | 3/2006 | Prasit et al. |
| 7,902,181 | B2 | 3/2011 | Furber et al. |
| 8,859,774 | B2 | 10/2014 | Hunt et al. |
| 8,877,775 | B2 * | 11/2014 | Anderskewitz et al. ..... C07D 221/22 514/311 |
| 8,933,236 | B2 | 1/2015 | Chowdhury et al. |
| 8,952,151 | B2 | 2/2015 | Chen et al. |
| 8,987,249 | B2 | 3/2015 | Anderskewitz et al. |
| 8,999,975 | B2 | 4/2015 | Grundl et al. |
| 9,006,242 | B2 | 4/2015 | Kuntz et al. |
| 9,056,874 | B2 | 6/2015 | Adams et al. |
| 9,066,946 | B2 | 6/2015 | Vaca et al. |
| 9,145,387 | B2 | 9/2015 | Haq et al. |
| 9,156,824 | B2 | 10/2015 | Dally et al. |
| 9,180,169 | B2 | 11/2015 | Tolborg et al. |
| 9,181,271 | B2 | 11/2015 | Li et al. |
| 9,233,974 | B2 | 1/2016 | Link et al. |

(Continued)

FOREIGN PATENT DOCUMENTS

| | | |
|---|---|---|
| GE | 20012487 | 4/2001 |
| WO | 9105282 A1 | 4/1991 |

(Continued)

OTHER PUBLICATIONS

International Search Report and Written Opinion for PCT/EP2015/070449 dated Oct. 22, 2015.
Abstract in English for GE 20012487, publication date Apr. 10, 2001.
International Search Report and Written Opinion for PCT/EP2015/067271 dated Sep. 22, 2015.
International Search Report for PCT/EP2014/054794 dated Apr. 2, 2014.
International Search Report for PCT/EP2014/054798 dated Apr. 4, 2014.
International Search Report for PCT/EP2014/054802 dated Apr. 10, 2014.

(Continued)

*Primary Examiner* — Alan D Diamond
(74) *Attorney, Agent, or Firm* — Philip I. Datlow

(57) ABSTRACT

This invention relates to a compound of formula I

I wherein A and Cy have one of the meanings as indicated in the specification and their use as inhibitors of Cathepsin C, pharmaceutical compositions containing the same and methods of using the same as agents for treatment and/or prevention of diseases connected with dipeptidyl peptidase I activity, e.g. respiratory diseases.

44 Claims, 1 Drawing Sheet

(56) References Cited

U.S. PATENT DOCUMENTS

| | | | |
|---|---|---|---|
| 9,242,969 | B2 | 1/2016 | Barsani et al. |
| 9,290,476 | B2 | 3/2016 | Leonard et al. |
| 9,375,418 | B2 | 6/2016 | Schmidt et al. |
| 9,428,452 | B2 | 8/2016 | Birault et al. |
| 9,434,719 | B2 | 9/2016 | Caferre et al. |
| 9,434,761 | B2 | 9/2016 | McMinn et al. |
| 9,532,992 | B2 | 1/2017 | Kuntz et al. |
| 9,540,373 | B2 | 1/2017 | Vintonyak et al. |
| 2006/0223846 | A1 | 10/2006 | Dyatkin et al. |
| 2009/0247560 | A1 | 10/2009 | Ando et al. |
| 2013/0172327 | A1 | 7/2013 | Grundl et al. |
| 2014/0213554 | A1 | 7/2014 | Wu et al. |
| 2016/0001608 | A1 | 1/2016 | Abdallah et al. |
| 2016/0060266 | A1 | 3/2016 | Kumar et al. |
| 2016/0075727 | A1 | 3/2016 | Burger et al. |
| 2016/0102094 | A1 | 4/2016 | Breslin et al. |
| 2017/0008891 | A1 | 1/2017 | Tao et al. |

FOREIGN PATENT DOCUMENTS

| | | | |
|---|---|---|---|
| WO | 2002002556 | A2 | 1/2002 |
| WO | 02069901 | A2 | 9/2002 |
| WO | 2003080046 | A1 | 10/2003 |
| WO | 2004110988 | A1 | 12/2004 |
| WO | 2005042533 | A2 | 5/2005 |
| WO | 2009047829 | A1 | 4/2009 |
| WO | 2009074829 | A1 | 6/2009 |
| WO | 2010128324 | A1 | 11/2010 |
| WO | 2010142985 | A1 | 12/2010 |
| WO | 2012119941 | A1 | 9/2012 |
| WO | 2013041497 | A1 | 3/2013 |
| WO | 2014056942 | A1 | 4/2014 |
| WO | 2014140075 | A1 | 9/2014 |
| WO | 16038120 | A1 | 3/2016 |
| WO | 16040083 | A1 | 3/2016 |

OTHER PUBLICATIONS

International Search Report for PCT/EP2014/054827 dated Apr. 28, 2014.

Berge et al., "Pharmaceutical Salts", J. Pharm. Sci., 1977, 66, pp. 1-19.

Dahl et al., "Human Recombinant Pro-dipeptidyl Peptidase I (Cathepsin C) Can Be Activated by Cathepsins L and S but Not byAutocatalytic Processing", 2000, Biochemistry 40, pp. 1671-1678.

Emsley et al, "Coot: model-building tools for molecular graphics", Acta Cryst. Section D Biological Crystallography, 2004, D60, pp. 2126-2132.

Furber et al., "Cathepsin C Inhibitors: Property Optimization and Identification of a Clinical Candidate", J. Med. Chem., 2014, 57, pp. 2357-2367.

Guay et al., "Therapeutic Utility and Medicinal Chemistry of Cathepsin C Inhibitors", Curr. Topics Med. Chem., 2010, 10: pp. 708-716.

Gutmann et al., "On the proteolytic enzymes of animal tissues", J. Biol. Chem, 1948, 174: pp. 851-858.

Kabsch et al., "XDS", Acta Crystallogr. D. Biol. Crystallography, 2010, 66, pp. 125-132.

Kominami et al., "The Primary Structure and Tissue Distribution of Cathepsin C" Biol. Chem. Hoppe Seyler, 1992, 373: pp. 367-373.

Laine et al., "Inhibitors of cathepsin C (dipeptidyl peptidase I)", Expert Opin. Ther. Patents, 2010, 20: pp. 497-506.

Dolenc et al., "Interaction of human cathespin C with chicken crystatin", FEBS Letters, 1996, 392, pp. 277-280.

Pham et al., "Dipeptidyl peptidase I is required for the processing and activation of granzymes A and B in vivo", Proc. Nat. Acad. Sci, 1999, 96: pp. 8627-8632.

Turk et al., "Structure of human dipeptidyl peptidase I (cathepsin C): exclusion domain added to an endopeptidase framework creates the machine for activation of granular serine proteases", The EMBO J., 2001, vol. 20 No. 23, pp. 6570-6582.

Wolters et al., "Dipeptidyl Peptidase I Is Essential for Activation of Mast Cell Chymases, but Not Tryptases, in Mice", 2001, J Biol. Chem. 276: pp. 18551-18556.

Wolters et al., "Regulated Expression, Processing, and Secretion of Dog Mast Cell Dipeptidyl Peptidase I", J. Biol. Chem., 1998, 273: pp. 15514-15520.

Abstract in English for WO 2009/047829, publication date Apr. 16, 2009.

Adkison, A.M. et al., "Dipeptidyl peptidase I activates neutrophil-derived serine proteases and regulates the development of acute experimental arthritis." The Journal of Clinical Investigation, 2002, vol. 109, No. 3, pp. 363-371.

Akk, A.M. et al., "Dipeptidyl Peptidase I-Dependent Neutrophil Recruitment Modulates the Inflammatory Response to Sendai Virus Infection." The Journal of Immunology, 2008, vol. 180, pp. 3535-3542.

Bondebjerg, J. et al., "Dipeptidyl nitriles as human dipeptidyl peptidase I inhibitors." Bioorganic & Medicinal Chemistry Letters, 2006, vol. 16, No. 13, pp. 3614-3617.

Farberman, M.M. et al., "Airway proteins involved in bacterial clearance susceptible to cathepsin G proteolysis." European Respiratory Journal, 2010, vol. 35, No. 2, pp. 410-417.

Guay, D. et al., "Design and synthesis of dipeptidyl nitriles as potent, selective, and reversible inhibitors of cathespin C." Bioorganic & Medicinal Chemistry Letters, 2009, vol. 19, No. 18, pp. 5392-5396.

Guyot, N. et al., "Deficiency in All Three Neutrophil Serine Proteases Protects Mice Against Cigarette Smoke-Induced Emphysema." American Journal of Respiratory and Critical Care Medicine, 2010, vol. 181, p. A5128.

Henriksen, P.A. et al., "Human neutrophil elastase: Mediator and therapeutic target in atherosclerosis." The International Journal of Biochemistry & Cell Biology, 2008, vol. 40, pp. 1095-1100.

Herias, M. et al., "Abstract 5871: Leukocyte Cathepsin C Deficiency Attenuates Atherosclerosis in LDL Receptor Deficient Mice." Circulation, 2009, vol. 120, p. 1166.

Hu, Y. et al., "Dipeptidyl Peptidase I Regulates the Development of Collagen-Induced Arthritis." Arthritis & Rheumatism, 2005, vol. 52, No. 8, pp. 2553-2558.

Joosten, L.A. et al., "Inflammatory Arthritis in Caspase 1 Gene-Deficient Mice." Arthritis & Rheumatism, 2009, vol. 60, No. 12, pp. 3651-3662.

Koga, H. et al., "Inhibition of neutrophil elastase attenuates airway hyperresponsiveness and inflammation in a mouse model of secondary allergen challenge: neutrophil elastase inhibition attenuates allergic airway responses." Respiratory Research, 2013, vol. 14, No. 8, pp. 1-13.

Kotlowski, R. et al., "Population-Based Case-Control Study of Alpha 1-Antitrypsin and SLC11A1 in Crohn's Disease and Ulcerative Colitis." Inflammatory Bowel Disease, 2008, vol. 14, No. 8, pp. 1112-1117.

Laprise, C. et al., "Functional classes of bronchial mucosa genes that are differentially expressed in asthma." BMC Genomics, 2004, vol. 5, No. 21, pp. 1-10.

Liu, H. et al., "Neutrophil elastase and elastase-rich cystic fibrosis sputum degranulate human eosinophils in vitro." American Physiological Scoiety, 1999, vol. 276, pp. L28-L34.

Milner, J.M. et al., "Emerging Roles of Serine Proteinases in Tissue Turnover in Arthritis." Arthritis & Rheumatism, 2008, vol. 58, No. 12, pp. 3644-3656.

Morohoshi, Y. et al., "Inhibition of neutrophil elastase prevents the development of murine dextran sulfate sodium-induced colitis." Journal of Gastroenterology, 2006, vol. 41, pp. 318-324.

Motta, Jean-Paul et al., "Modifying the Protease, Antiprotease Pattern by Elafin Overexpression Protects Mice From Colitis." Gastroenterology, 2011, vol. 140, pp. 1272-1282.

Schmid, M. et al., "Attenuated induction of epithelial and leukocyte serine antiproteases elafin and secretory leukocyte protease inhibitor in Crohn's disease." Journal of Leukocyte Biology, 2007, vol. 81, pp. 907-915.

Sedor, J. et al., "Cathepsin-G Interferes with Clearance of Pseudomonas aeruginosa from Mouse Lungs." Pediatric Research, 2007, vol. 61, No. 1, pp. 26-31.

(56) References Cited

OTHER PUBLICATIONS

Shapiro, S.D. et al., "Neutrophil Elastase Contributes to Cigarette Smoke-Induced Emphysema in Mice." American Journal of Pathology, 2003, vol. 163, No. 6, pp. 2329-2335.
Wright, J.L. et al., "Synthetic Serine Elastase Inhibitor Reduces Cigarette Smoke-Induced Emphysema in Guinea Pigs." Ameican Journal of Respiratory and Critical Care Medicine, 2002, vol. 166, pp. 954-960.
Yuyama, N. et al., "Analysis of Novel Disease-Related Genes in Bronchial Asthma." Cytokine, 2002, vol. 19, No. 6, pp. 287-296.

* cited by examiner

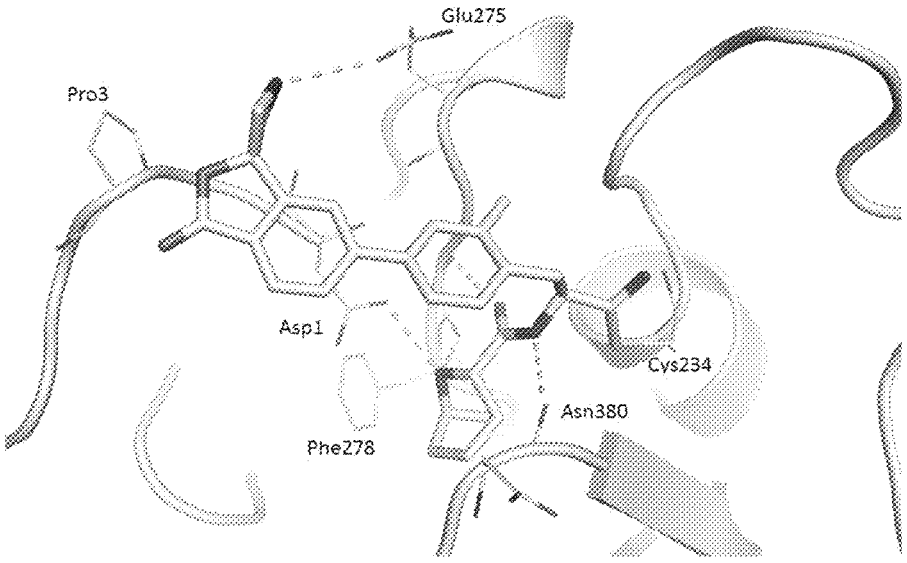
(A)
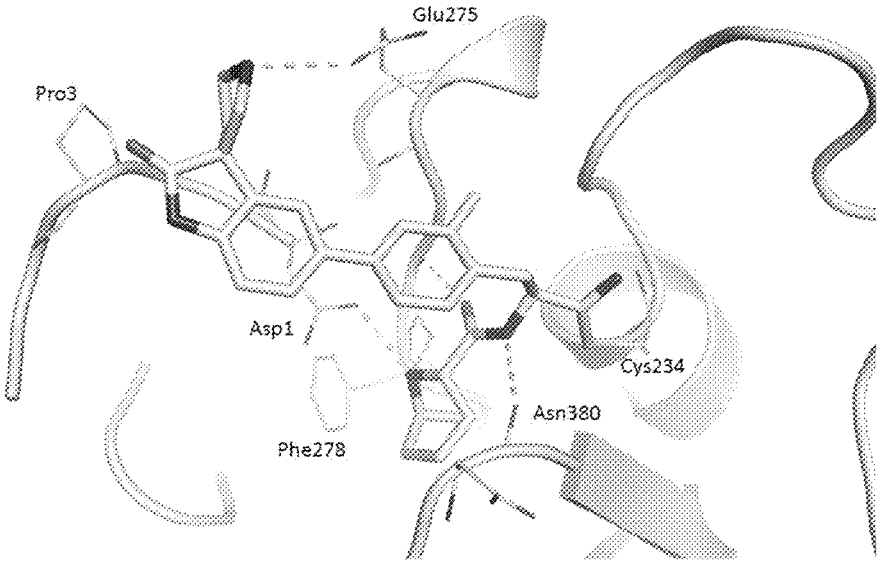
(B)

SUBSTITUTED SPIROCYCLES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application claims the benefit of EP Application No. 14184613.9, filed Sep. 12, 2014, the entire content of which is incorporated herein by reference in its entirety as though fully set forth herein.

FIELD OF INVENTION

This invention relates to a compound of formula I

I

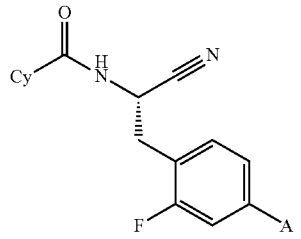

wherein A and Cy have one of the meanings as indicated in the specification and their use as inhibitors of Cathepsin C, pharmaceutical compositions containing the same and methods of using the same as agents for treatment and/or prevention of diseases connected with dipeptidyl peptidase I activity, e.g. respiratory diseases.

BACKGROUND INFORMATION

WO2004110988 discloses peptidyl nitrile inhibitors as dipeptidyl-peptidase I (DPPI) inhibitors for the treatment of a series of diseases.

WO2009074829 and WO2010142985 also disclose peptidyl nitrile inhibitors as dipeptidyl-peptidase I (DPPI) inhibitors for the treatment asthma, COPD or allergic rhinitis.

WO2013041497 discloses substituted N-[1-cyano-2-(phenyl)ethyl]-2-azabicyclo[2.2.1]heptane-3-carboxamides as dipeptidyl-peptidase I (DPPI) inhibitors for the treatment of e.g. respiratory diseases.

BRIEF SUMMARY OF THE INVENTION

Dipeptidyl-aminopeptidase I (DPPI or Cathepsin C; EC3.4.141), is a lysosomal cysteine protease capable of removing dipeptides from the amino terminus of protein substrates. DPPI was first discovered by Gutman and Fruton in 1948 (J. Biol. Chem 174: 851-858, 1948). The cDNA of the human enzyme has been described in 1995 (Paris et al.; FEBS Lett 369: 326-330, 1995). The DPPI protein is processed into a mature proteolytically active enzyme consisting of a heavy chain, a light chain, and a propeptide that remains associated with the active enzyme (Wolters et al.; J. Biol. Chem. 273: 15514-15520, 1998). Whereas the other cysteine Cathepsins (e.g. B, H, K, L and S) are monomers, DPPI is a 200-kD tetramer with 4 identical subunits, each composed of the 3 different polypeptide chains DPPI is constitutively expressed in many tissues with highest levels in lung, kidney, liver and spleen (Kominami et al.; Biol. Chem. Hoppe Seyler 373: 367-373, 1992). Consistent with its role in the activation of serine proteases from hematopoetic cells, DPPI is also relatively highly expressed in neutrophils, cytotoxic lymphocytes, natural killer cells, alveolar macrophages and mast cells. Recent data from DPPI deficient mice suggest that, besides being an important enzyme in lysosomal protein degradation, DPPI also functions as the key enzyme in the activation of granule serine proteases in cytotoxic T lymphocytes and natural killer cells (granzymes A and B; Pham et al.; Proc. Nat. Acad. Sci 96: 8627-8632, 1999), mast cells (chymase and tryptase; Wolter et al.; J Biol. Chem. 276: 18551-18556, 2001), and neutrophils (Cathepsin G, elastase and proteinase 3; Adkison et al.; J Clin. Invest. 109: 363.371, 2002). Once activated, these proteases are capable of degrading various extracellular matrix components, which can lead to tissue damage and chronic inflammation.

Thus, inhibitors of Cathepsin C could potentially be useful therapeutics for the treatment of neutrophil-dominated inflammatory diseases such as chronic obstructive pulmonary disease (COPD), pulmonary emphysema, asthma, multiple sclerosis, and cystic fibrosis (Guay et al.; Curr. Topics Med. Chem. 10: 708-716, 2010; Laine and Busch-Petersen; Expert Opin. Ther. Patents 20: 497-506, 2010). Rheumatoid arthritis is also another chronic inflammatory disease where DPPI appears to play a role. Neutrophils are recruited to the site of joint inflammation and release Cathepsin G, elastase and proteinase 3, proteases which are believed to be responsible for cartilage destruction associated with rheumatoid arthritis. Indeed, DPPI deficient mice were protected against acute arthritis induced by passive transfer of monoclonal antibodies against type II collagen (Adkison et al.; J Clin. Invest. 109: 363.371, 2002).

In light of the role DPPI plays in activating certain pro-inflammatory serine proteases, the problem of the present invention is to prepare compounds that inhibit its activity, which thereby inhibit downstream serine protease activity.

It has been surprisingly found that the spirocyclic compounds of the present invention possess potent Cathepsin C (DPPI) activity, preferably exhibiting an inhibition of DPPI $IC_{50}$ [μM]<0.0050, particularly preferred <0.0030, Moreover the compounds of the present invention exhibit the following capacities, which are favourable for their pharmacological efficacy:

high cellular activity, e g inhibition of neutrophil elastase processing in U937 cell line, preferably exhibiting an IC50 [μM]<0.5, particularly preferred <0.003.

high selectivity against other Cathepsins, e.g. Cathepsin K, and in general desirable pharmacokinetic properties, e.g. metabolic stability, preferably exhibiting an in vitro stability in human liver microsome incubations of t½ [min]>110, particularly preferred ≥120.

It has also been surprisingly found that compounds of the present invention show high inhibition of neutrophil elastase activity in the BALF (bronchoalveolar lavage fluid) cell lysate in a target engagement mouse model.

Moreover it has been surprisingly found that the spirocyclic compounds of the present invention form an additional salt-bridge to the Glu275 of the Cathepsin C which leads to the high enzymatic and cellular activity of this compound class. This additional interaction of the spirocyclic amine (e.g. spiro-azetidine in Example 11 and spiro-pyrrolidine in Example 16) has been verified by co-crystallization experiments of Cathepsin C protein with Examples 11 and 16. In both cases the basic nitrogen atom forms a salt-bridge to Glu275.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

FIGS. 1 (A) and (B) show the structures of Cathepsin C ligand complexes in Example 11 (FIG. 1 (A)) and in Example 16 (FIG. 1(B)). The protein is shown in ribbon representation, with selected residues shown as sticks. Ligands are shown as stick representation, hydrogen bonds as dotted lines.

DETAILED DESCRIPTION OF THE INVENTION

It has surprisingly been found that the problem mentioned above is solved by compounds of formula I of the present invention.

The present invention therefore relates to a compound of formula I or a pharmaceutically acceptable salt thereof,

I

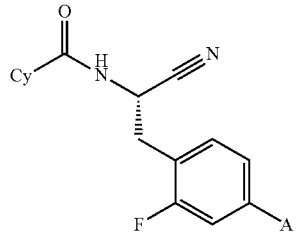

wherein

Cy is

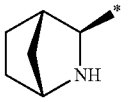

or

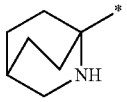

;

A is

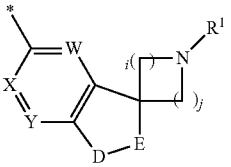

wherein

W is selected from the group consisting of CH and N;

X is selected from the group consisting of CH and N;

Y is selected from the group consisting of CH and N;

with the proviso that a maximum of one of W, X and Y can be N;

D-E is selected from the group consisting of $N(R^2)$—C(O), $CH_2CH_2$, C(O)—O and $CH_2$—O;

$R^2$ is selected from the group consisting of H and $C_{1-3}$-alkyl;

$R^1$ is selected from the group consisting of H, $C_{1-3}$-alkyl, $CH_3OCH_2CH_2$—, oxetanyl, tetrahydrofuranyl, 4-tetrahydropyranyl and 3-tetrahydropyranyl;

i is 1, 2 or 3;

j is 1, 2 or 3;

with the proviso that the sum of i+j is 2, 3 or 4.

Preferred Embodiments

Particularly preferred are the above compounds of formula I, or a pharmaceutically acceptable salt thereof, wherein Cy is

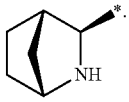

Preferred are the above compounds of formula I, or a pharmaceutically acceptable salt thereof, wherein Cy is

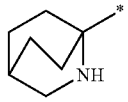

Preferred are the above compounds of formula I, or a pharmaceutically acceptable salt thereof, wherein $R^1$ is selected from the group consisting of H, $CH_3$— and oxetanyl;

Preferred are the above compounds of formula I, or a pharmaceutically acceptable salt thereof, wherein $R^2$ is selected from the group consisting of H and $CH_3$;

Preferred are the above compounds of formula I, or a pharmaceutically acceptable salt thereof, wherein $R^2$ is H.

Preferred are the above compounds of formula I, or a pharmaceutically acceptable salt thereof, wherein $R^2$ is $CH_3$;

Preferred are the above compounds of formula I, or a pharmaceutically acceptable salt thereof, wherein D-E is $CH_2$—O Preferred are the above compounds of formula I, or a pharmaceutically acceptable salt thereof, wherein $R^1$ is selected from the group consisting of H, $CH_3$ and oxetanyl;

$R^2$ is $CH_3$,

W is selected from the group consisting of CH and N;

X is selected from the group consisting of CH and N;

Y is selected from the group consisting of CH;

with the proviso that a maximum of one of W, X and Y can be N;

D-E is selected from the group consisting of $N(R^2)$—C(O), $CH_2CH_2$, C(O)—O and $CH_2$—O;

i is 1 or 2;

j is 1 or 2;

with the proviso that the sum of i+j is 2, 3 or 4.

Preferred are the above compounds of formula I, or a pharmaceutically acceptable salt thereof, wherein A is selected from the group consisting of formulas A1 to A14:

A1

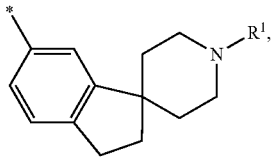

A2

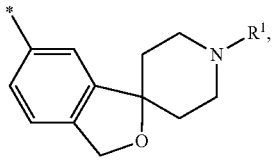

A3

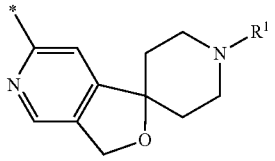

A4

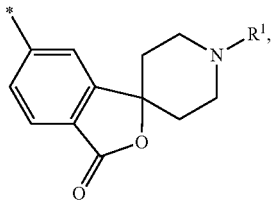

A5

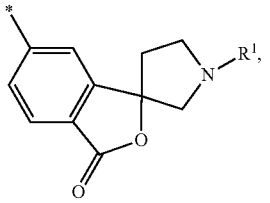

A6

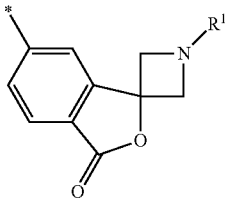

A7

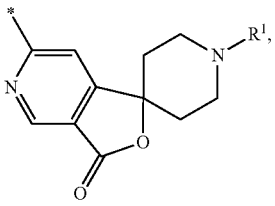

-continued

A8

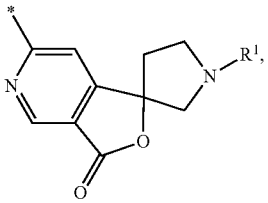

A9

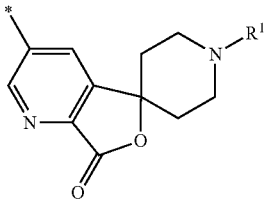

A10

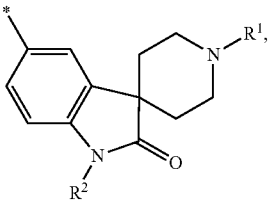

A11

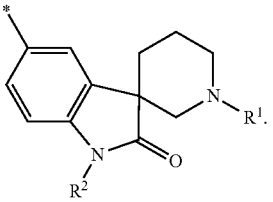

A12

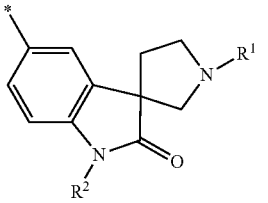

A13

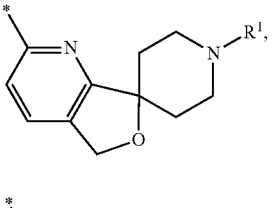

A14

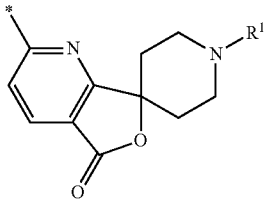

Preferred are the above compounds of formula I, or a pharmaceutically acceptable salt thereof, wherein A is selected from the group consisting of A2, A3, A4, A5, A6, A7, A10, A13, and A14.

A2

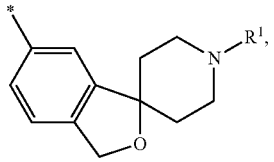

A3

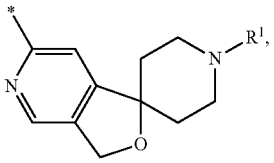

A4

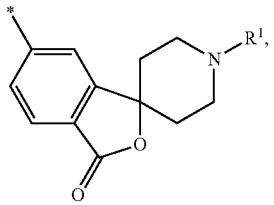

A5

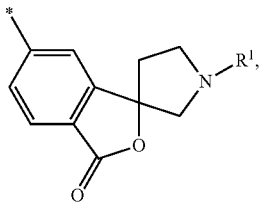

A6

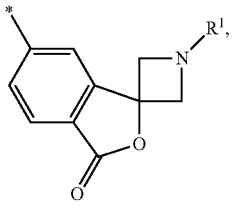

A7

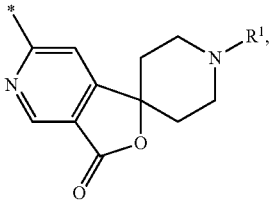

A10

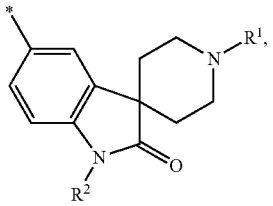

A13

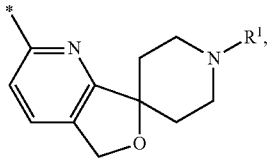

-continued

A14

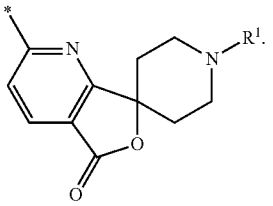

Preferred are the above compounds of formula I, or a pharmaceutically acceptable salt thereof, wherein A is selected from the group consisting of A2 and A13

A2

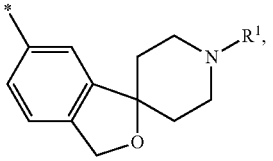

A13

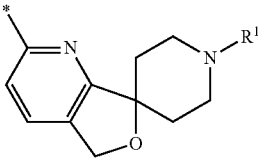

Preferred are the above compounds of formula I, or a pharmaceutically acceptable salt thereof, wherein A is a group of formulas A2.1.

A2.1

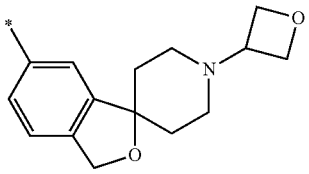

Preferred are the above compounds of formula I, or a pharmaceutically acceptable salt thereof, wherein A is a group of formula A13.1

A13.1

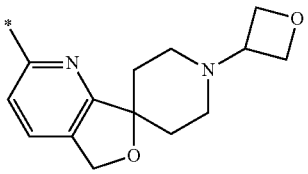

Preferred are the above compounds of formula I, selected from the group consisting of examples 1, 5, 8, 10, 12, 13, 14, 19, 22, 23, 24, 25 and 27.

Ex. 1
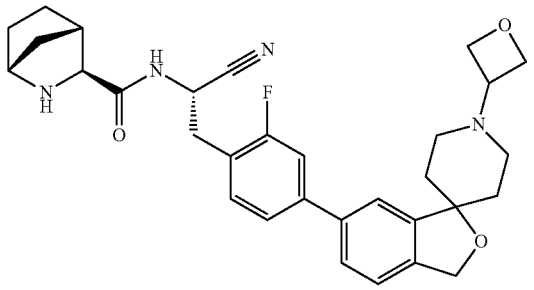
Ex. 5
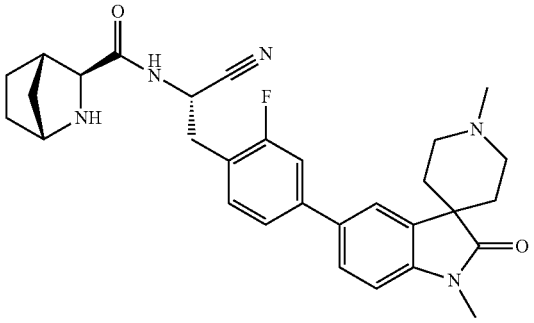
Ex. 8
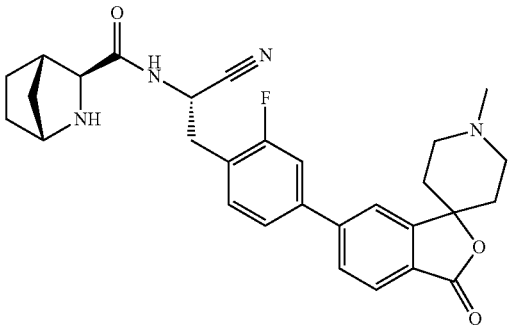
Ex. 10
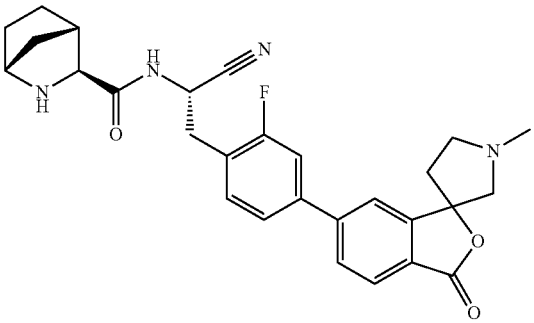
-continued
Ex.12
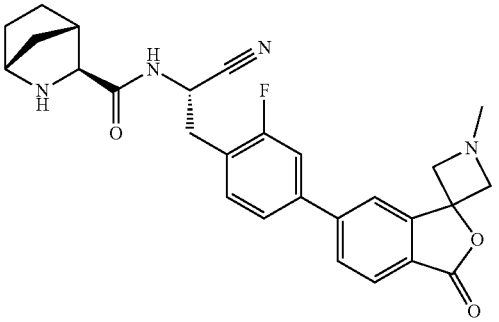
Ex. 13
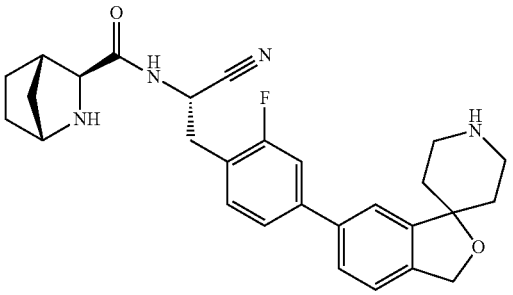
Ex. 14
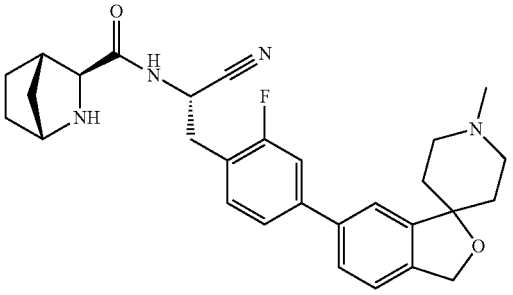
Ex. 19
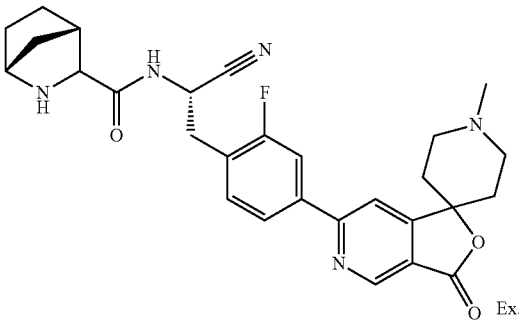
Ex. 22
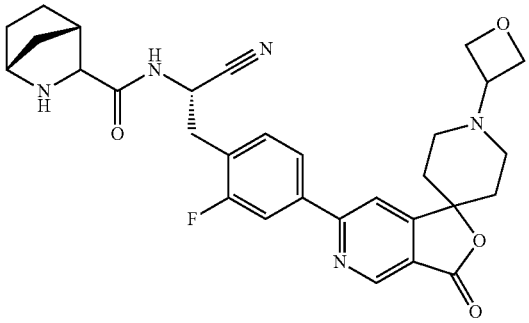

-continued

Ex. 23

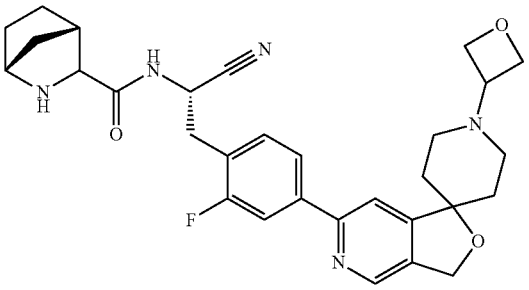

Ex. 24

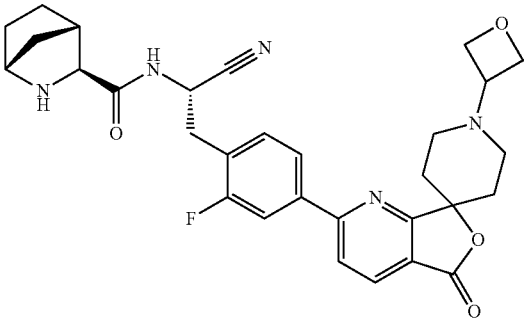

Ex. 25

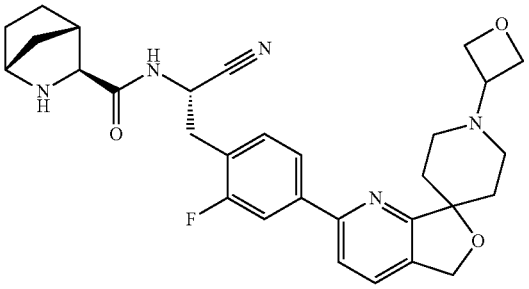

Ex. 27

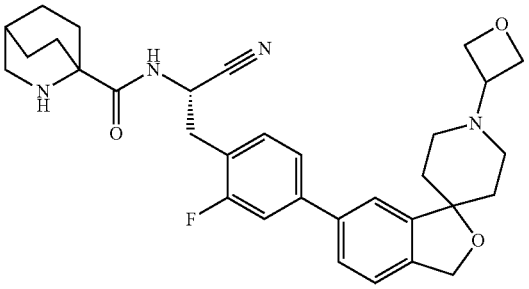

Preferred are the above compounds of formula I, or a pharmaceutically acceptable salt thereof, wherein $R^1$ is selected from the group consisting of H and $CH_3$.

Particularly preferred are the above compounds of formula I, or a pharmaceutically acceptable salt thereof, wherein $R^1$ is oxetanyl.

Preferred are the above compounds of formula I, or a pharmaceutically acceptable salt thereof, wherein $R^1$ is selected from the group consisting of H, $CH_3$ and oxetanyl;

$R^2$ is selected from the group consisting of H and $CH_3$—.

Preferred are the above compounds of formula I, or a pharmaceutically acceptable salt thereof, wherein $R^1$ is selected from the group consisting of H and $CH_3$;

$R^2$ is selected from the group consisting of H and $CH_3$.

Preferred are the above compounds of formula I, or a pharmaceutically acceptable salt thereof, wherein D-E is selected from the group consisting of $CH_2$—O, C(O)—O and N($R^2$)—C(O).

Particularly preferred are the above compounds of formula I, or a pharmaceutically acceptable salt thereof, wherein D-E is selected from the group consisting of $CH_2$—O and C(O)—O.

Preferred are the above compounds of formula I, or a pharmaceutically acceptable salt thereof, wherein $R^1$ is selected from the group consisting of H, $CH_3$ and oxetanyl;

$R^2$ is selected from the group consisting of H and $CH_3$.

D-E is selected from the group consisting of $CH_2$—O, C(O)—O and N($R_2$)—C(O).

Particularly preferred are the above compounds of formula I, or a pharmaceutically acceptable salt thereof, wherein $R^1$ is selected from the group consisting of H, $CH_3$, oxetanyl;

D-E is selected from the group consisting of $CH_2$—O and C(O)—O.

Particularly preferred are the above compounds of formula I, or a pharmaceutically acceptable salt thereof, wherein $R^1$ is selected from the group consisting of oxetanyl;

D-E is selected from the group consisting of $CH_2$—O and C(O)—O.

Particularly preferred are the above compounds of formula I, or a pharmaceutically acceptable salt thereof, wherein W is CH;

X is CH;

Y is CH.

Preferred are the above compounds of formula I, or a pharmaceutically acceptable salt thereof, wherein W is CH;

X is N;

Y is CH.

Preferred are the above compounds of formula I, or a pharmaceutically acceptable salt thereof, wherein W is N;

X is CH;

Y is CH.

Preferred are the above compounds of formula I, or a pharmaceutically acceptable salt thereof, wherein W is CH;

X is CH;

Y is N.

Preferred are the above compounds of formula I, or a pharmaceutically acceptable salt thereof, wherein $R^1$ is selected from the group consisting of H, $CH_3$— and oxetanyl;

$R^2$ is selected from the group consisting of H and $CH_3$—;

D-E is selected from the group consisting of $CH_2$—O, C(O)—O and N($R_2$)—C(O);

W is CH;

X is CH;

Y is CH.

Particularly preferred are the above compounds of formula I, or a pharmaceutically acceptable salt thereof, wherein $R^1$ is selected from the group consisting of H, $CH_3$— and oxetanyl;

D-E is selected from the group consisting of $CH_2$—O and C(O)—O;
W is CH;
X is CH;
Y is CH.

Preferred are the above compounds of formula I, or a pharmaceutically acceptable salt thereof, wherein
$R^1$ is selected from the group consisting of H, $CH_3$— and oxetanyl;
$R^2$ is selected from the group consisting of H and $CH_3$—;
D-E is selected from the group consisting of $CH_2$—O, C(O)—O and N($R_2$)—C(O);
W is N;
X is CH;
Y is CH.

Particularly preferred are the above compounds of formula I, or a pharmaceutically acceptable salt thereof, wherein
$R^1$ is selected from the group consisting of H, $CH_3$— and oxetanyl;
D-E is selected from the group consisting of $CH_2$—O and C(O)—O;
W is N;
X is CH;
Y is CH.

Preferred are the above compounds of formula I, or a pharmaceutically acceptable salt thereof, wherein
$R^1$ is selected from the group consisting of H, $CH_3$— and oxetanyl;
$R^2$ is selected from the group consisting of H and $CH_3$—;
D-E is selected from the group consisting of $CH_2$—O, C(O)—O and N($R_2$)—C(O);
W is CH;
X is N;
Y is CH.

Particularly preferred are the above compounds of formula I, or a pharmaceutically acceptable salt thereof, wherein
$R^1$ is selected from the group consisting of H, $CH_3$— and oxetanyl;
D-E is selected from the group consisting of $CH_2$—O and C(O)—O;
W is CH;
X is N;
Y is CH.

Preferred are the above compounds of formula I, or a pharmaceutically acceptable salt thereof, wherein
$R^1$ is selected from the group consisting of H, $CH_3$— and oxetanyl;
$R^2$ is selected from the group consisting of H and $CH_3$—;
D-E is selected from the group consisting of $CH_2$—O, C(O)—O and N($R_2$)—C(O);
W is CH;
X is CH;
Y is N.

Particularly preferred are the above compounds of formula I, or a pharmaceutically acceptable salt thereof, wherein
$R^1$ is selected from the group consisting of H, $CH_3$— and oxetanyl;
D-E is selected from the group consisting of $CH_2$—O and C(O)—O;
W is CH;
X is CH;
Y is N.

Particularly preferred are the above compounds of formula I, or a pharmaceutically acceptable salt thereof, wherein A is selected from the group consisting of A2, A3, A4, A5, A6, A7, A8, A9, A10, A11, A12, A13 and A14.

Particularly preferred are the above compounds of formula I, or a pharmaceutically acceptable salt thereof, wherein A is selected from the group consisting of A1, A2, A3, A4, A6, A7, A9, A10, A13 and A14.

Particularly preferred are the above compounds of formula I, or a pharmaceutically acceptable salt thereof, wherein A is selected from A4, A5, A6, A7 A8, A9 and A14.

Particularly preferred are the above compounds of formula I, or a pharmaceutically acceptable salt thereof, wherein A is selected from the group consisting of A10, A11 and A12.

Particularly preferred are the above compounds of formula I, or a pharmaceutically acceptable salt thereof, wherein A is selected from the group consisting of A2, A3, A9, A13 and A14.

Particularly preferred are the above compounds of formula I, or a pharmaceutically acceptable salt thereof, wherein A is selected from the group consisting of A2, A3 and A13.

Particularly preferred are the above compounds of formula I, or a pharmaceutically acceptable salt thereof, wherein A is A2.

Particularly preferred are the above compounds of formula I, or a pharmaceutically acceptable salt thereof, wherein A is A13.

Preferred are the above compounds of formula I, or a pharmaceutically acceptable salt thereof, wherein i is 2 and j is 1.

Preferred are the above compounds of formula I, or a pharmaceutically acceptable salt thereof, wherein i is 1 and j is 1.

Particularly preferred are the above compounds of formula I, or a pharmaceutically acceptable salt thereof, wherein i is 2 and j is 2.

Preferred are the compounds of formula I, wherein the compounds are selected from the group consisting of examples 1, 3, 4, 5, 6, 7, 8, 10, 12, 13, 14, 16, 17, 18, 19, 20, 22, 23, 24, 25, 26 and 27.

Any and each of the definitions of $R^1$, $R^2$, Cy, A, D, E, W, X, Y, i and j may be combined with each other.

A further embodiment of the current invention is a compound of formula I or a pharmaceutically acceptable salt thereof for use as a medicament.

A further embodiment of the current invention is a compound of formula I or a pharmaceutically acceptable salt thereof for use as a medicament for the treatment of asthma and allergic diseases, gastrointestinal inflammatory diseases, glomerulonephritis, eosinophilic diseases, chronic obstructive pulmonary disease, infection by pathogenic microbes, rheumatoid arthritis, neutrophilic diseases, cystic fibrosis (CF), non-cystic fibrosis, idiopathic pulmonary fibrosis, bronchiectasis, ANCA-associated vasculitis, lung cancer, emphysema, chronic bronchitis, acute lung injury (ALI), acute respiratory distress syndrome (ARDS), pulmonary hypertension, pulmonary arterial hypertension (PAH) and Alpha-1-antitrypsin deficiency (AATD), obesity and related inflammation, insulin resistance, diabetes, fatty liver and liver steatosis.

Preferred is a compound of formula I or a pharmaceutically acceptable salt thereof for use as a medicament for the treatment of asthma and allergic diseases, gastrointestinal inflammatory diseases, eosinophilic diseases, chronic obstructive pulmonary disease, emphysema, infection by pathogenic microbes, rheumatoid arthritis and atherosclerosis. Particularly preferred is a compound of formula I or a pharmaceutically acceptable salt thereof for use as a medicament for the treatment of chronic obstructive pulmonary disease and emphysema.

A further embodiment of the current invention is a pharmaceutical composition, characterised in that it contains one or more compounds of formula or a pharmaceutically active salt thereof.

A further embodiment of the current invention is a method of treatment or prevention of diseases in which DPPI activity inhibitors have a therapeutic benefit, which method comprises administration of a therapeutically or preventively effective amount of a compounds of formula 1 to a patient in need thereof.

A further embodiment of the current invention is a pharmaceutical composition comprising additionally to a compound of formula I, a pharmaceutically active compound selected from the group consisting of betamimetics, anticholinergics, corticosteroids, PDE4 inhibitors, LTD4 antagonists, EGFR inhibitors, CRTH2 inhibitors, 5 LO inhibitors, Histamine receptor antagonists, CCR9 antagonists and SYK inhibitors, NE inhibitors, MMP9 inhibitors and MMP12 inhibitors, but also combinations of two or three active substances.

USED TERMS AND DEFINITIONS

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms.

In general in single groups like HO, $H_2N$, S(O), $S(O)_2$, NC (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-4}$-alkyl-" means an aryl group which is bound to a $C_{1-4}$-alkyl-group, the latter of which is bound to the core or to the group to which the substituent is attached. Alternatively, "*" indicates within a chemical entity, the point of attachment.

In case a compound of the present invention is depicted in form of a chemical name and as a formula in case of any discrepancy the formula shall prevail. An asterisk is may be used in sub-formulas to indicate the bond which is connected to the core molecule as defined.

Many of the followings terms may be used repeatedly in the definition of a formula or group and in each case have one of the meanings given above, independently of one another.

The term "substituted" as used herein, means that any one or more hydrogens on the designated atom is replaced with a selection from the indicated group, provided that the designated atom's normal valence is not exceeded and that the substitution results in a stable compound.

The expressions "prevention", "prophylaxis", "prophylactic treatment" or "preventive treatment" used herein should be understood synonymous and in the sense that the risk to develop a condition mentioned hereinbefore is reduced, especially in a patient having elevated risk for said conditions or a corresponding anamnesis, e.g. elevated risk of developing metabolic disorder such as diabetes or obesity or another disorder mentioned herein. Thus the expression "prevention of a disease" as used herein means the management and care of an individual at risk of developing the disease prior to the clinical onset of the disease. The purpose of prevention is to combat the development of the disease, condition or disorder and includes the administration of the active compounds to prevent or delay the onset of the symptoms or complications and to prevent or delay the development of related diseases, conditions or disorders. Success of said preventive treatment is reflected statistically by reduced incidence of said condition within a patient population at risk for this condition in comparison to an equivalent patient population without preventive treatment.

The expression "treatment" or "therapy" means therapeutic treatment of patients having already developed one or more of said conditions in manifest, acute or chronic form, including symptomatic treatment in order to relieve symptoms of the specific indication or causal treatment in order to reverse or partially reverse the condition or to delay the progression of the indication as far as this may be possible, depending on the condition and the severity thereof. Thus the expression "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

The term halogen generally denotes fluorine, chlorine, bromine and iodine.

The term "$C_{1-n}$-alkyl", wherein n is an integer selected from 2, 3, 4, 5 or 6, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "oxetanyl" denotes a 4-membered cyclic, saturated ring containing an oxygen atom in the 3-position with respect to the attachment point.

Preparation

General Synthetic Methods

The invention also provides processes for making a compound of Formula I.

Optimal reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC) or LC-MS, if desired, and intermediates and products may be purified by chromatography on silica gel, HPLC and/or by recrystallization. The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

A compound of Formula I may be made by the method outlined in Scheme 1, 2, 3 or 4:

Scheme 1

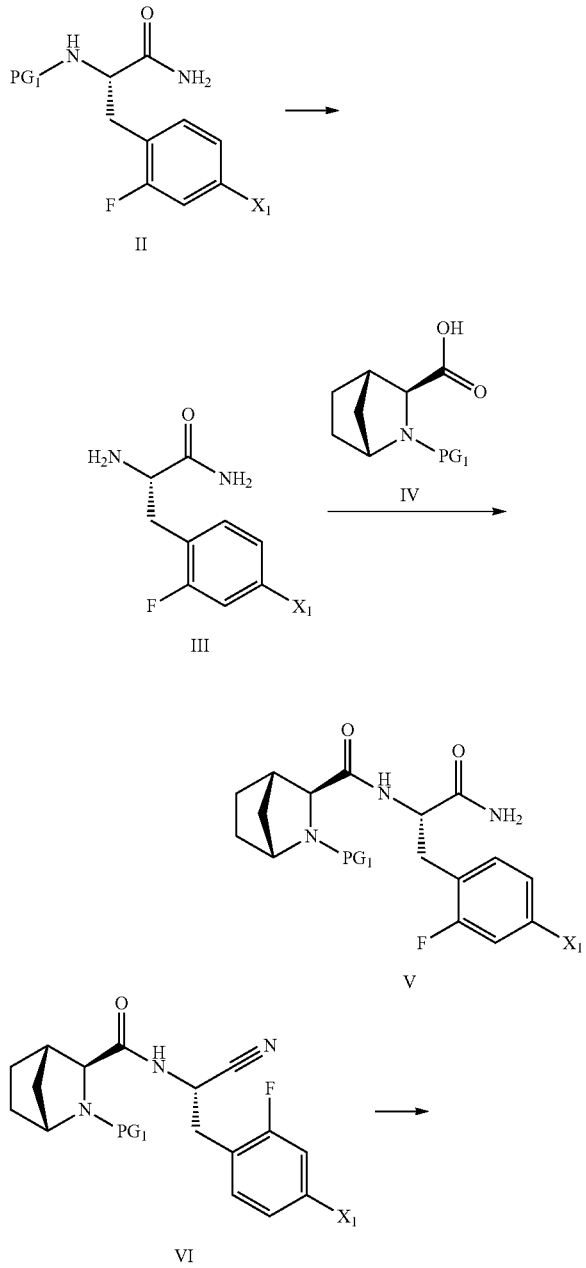

-continued

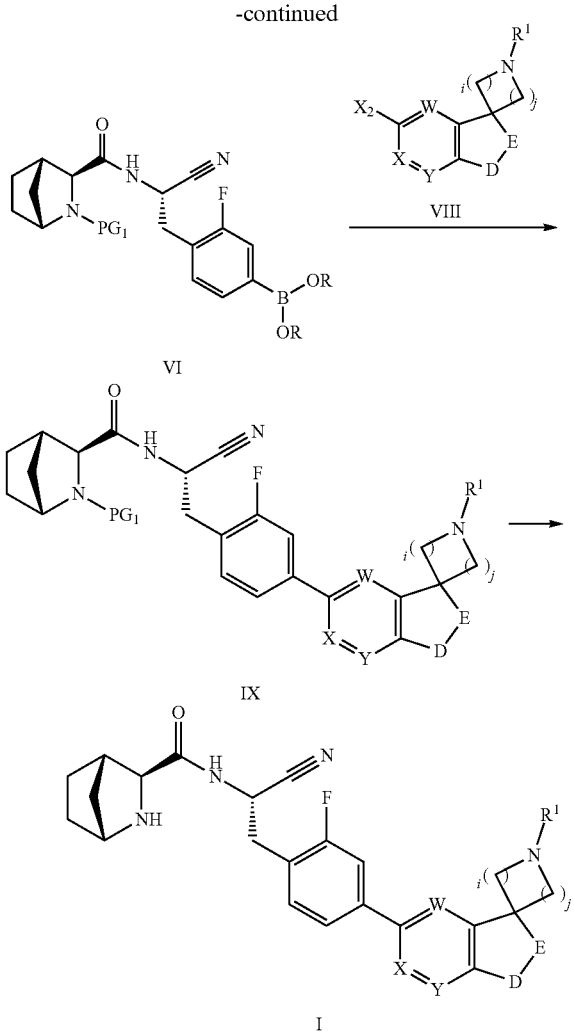

$X_1$ = I, Br
$X_2$ = Cl, Br

As illustrated in Scheme 1 the protection and deprotection of functional groups is described in 'Protective Groups in Organic Synthesis', T. W. Greene and P. G. M. Wuts, Wiley-Interscience. For example, for the deprotection of tert-butoxycarbonyl group, an acid such as formic acid, trifluoroacetic acid, p-toluenesulfonic acid or HCl may be used in a suitable solvent such as water, DCM or dioxane to provide a compound of Formula III.

Reacting an acid of Formula IV, wherein $PG_1$ represents a protecting group (e.g. tert-butoxycarbonyl) using standard literature procedures for the formation of an amide, for example in the presence of a base such as N,N-diisopropylethylamine (DIPEA) and an activating agent such as HATU or TBTU, with an amine of Formula III in a suitable solvent, provides a compound of Formula V. Standard peptide coupling reactions known in the art (see for example M. Bodanszky, 1984, The Practice of Peptide Synthesis, Springer-Verlag) may be employed in these syntheses.

Dehydration of an amide such as in a compound of Formula V to the corresponding nitrile of Formula VI may be carried out by use of a dehydration agent such as (methoxycarbonylsulfamoyl)triethyl ammonium hydroxide, in a suitable solvent such as dichloromethane (DCM).

Compounds of Formula VI ($X_1$=I, Br) can be converted into the corresponding boronic acid derivatives VII, wherein R can be H or lower alkyl independently and the residues R can form a ring. For example, VI can be reacted with bis(neopentyl glycolato)diboron in the presence of a suitable catalyst such as [1,1'-bis(diphenylphosphino)ferrocene]dichloropalladium(II), and a suitable base such as potassium acetate or sodium, potassium or cesium carbonate or phosphate, in a suitable solvent such as dioxan, dimethylformamide (DMF), or dichloromethane (DCM) to yield the boronic acid derivatives VII.

These can be reacted in a (transition) metal catalyzed reaction of a compound of Formula VIII ($X_2$=Cl, Br). Coupling of these halogenides VIII provide a compound of Formula IX. For example, reaction of these halogenides with a boronic acid or the corresponding boronic acid ester VII, in a suitable solvent such as dioxane, in the presence of a suitable catalyst such as 1,1'-bis(di-tert-butylphosphino)ferrocene palladium dichloride and a suitable base such as sodium, potassium or cesium carbonate, provides a compound of Formula IX.

The protection and deprotection of functional groups is described in 'Protective Groups in Organic Synthesis', T. W. Greene and P. G. M. Wuts, Wiley-Interscience. For example, for the deprotection of tert-butoxycarbonyl group, an acid such as p-toluenesulfonic acid monohydrate may be used in a suitable solvent such as acetonitrile to provide a compound of Formula I.

Scheme 2

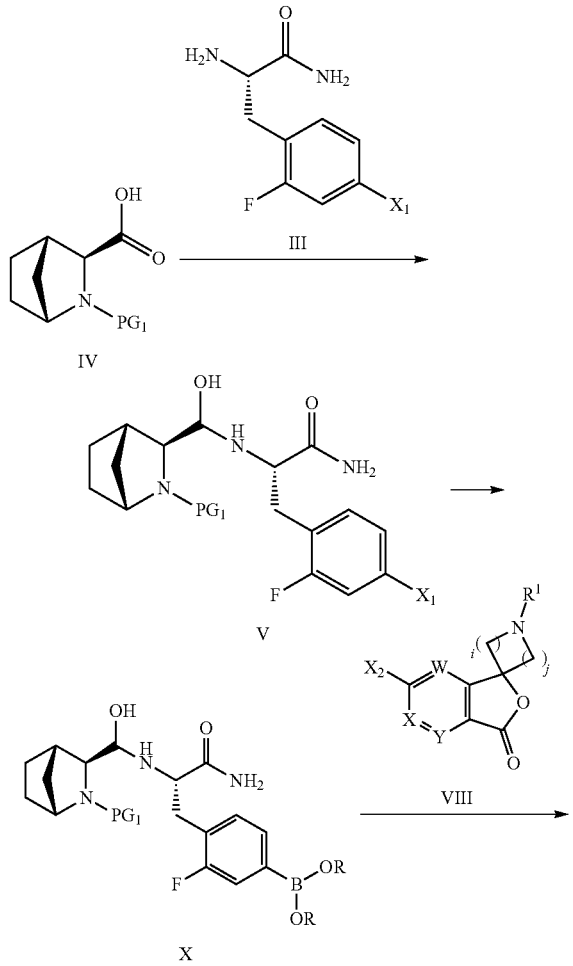

-continued

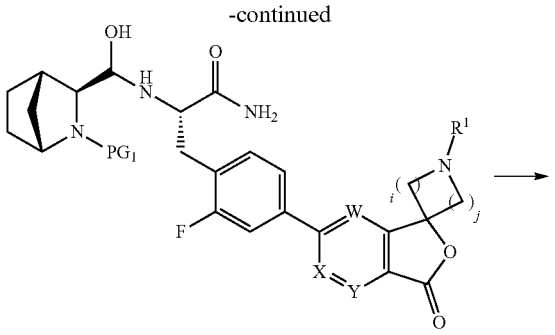

XI

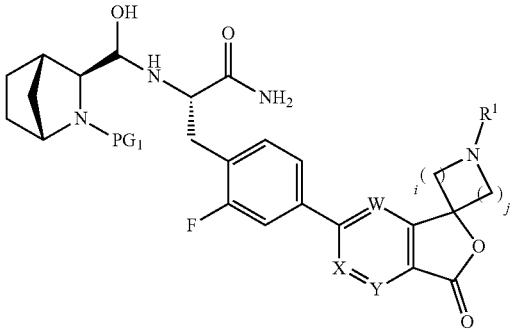

XII

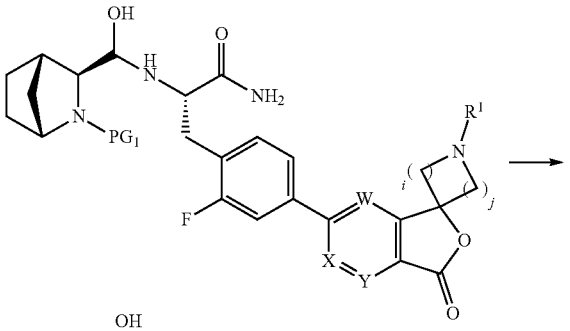

XIII

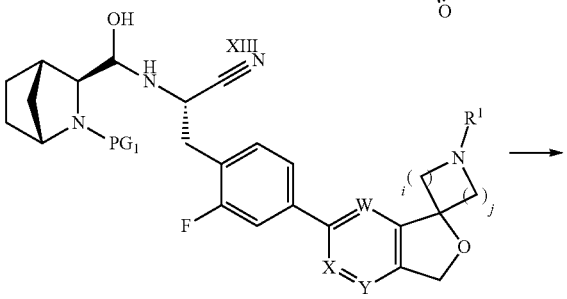

XIV

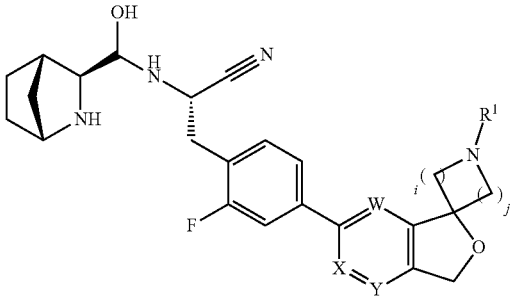

I $X_1$ = Br, I
$X_2$ = Cl, Br

As illustrated in Scheme 2 reacting an acid of Formula IV, wherein $PG_1$ represents a protecting group (e.g. tert-butoxycarbonyl) using standard literature procedures for the formation of an amide, for example in the presence of a base such as N,N-diisopropylethylamine (DIPEA) and an activating agent such as HATU or TBTU, with an amine of Formula III in a suitable solvent, provides a compound of Formula V. Standard peptide coupling reactions known in the art (see for example M. Bodanszky, 1984, The Practice of Peptide Synthesis, Springer-Verlag) may be employed in these syntheses.

Compounds of Formula V can be converted into the corresponding boronic acid derivatives X analogous to the reaction procedure described in Scheme 1.

These can be reacted in a (transition) metal catalyzed reaction of a compound of Formula VIII ($X_2$=Cl, Br) to yield a compound of the Formula XI analogous to the reaction procedure described in Scheme 1.

Compound of Formula XI can be converted into the compound of Formula XII using a reducing agent such as lithium or sodium borohydride in a suitable solvent such as tetrahydrofurane.

Compound of Formula XII can be converted into the compound of Formula XIII using reagents such as p-toluenesulfonic anhydride or methansulfonyl chloride in the presence of base such as triethylamine or N,N-diisopropylethylamine (DIPEA) in a suitable solvent such as tetrahydrofurane.

Dehydration of an amide such as in a compound of Formula XIII to the corresponding nitrile of Formula XIV may be carried out by use of a dehydration agent such as (methoxycarbonylsulfamoyl)triethyl ammonium hydroxide, in a suitable solvent such as dichloromethane (DCM).

The protection and deprotection of functional groups is described in 'Protective Groups in Organic Synthesis', T. W. Greene and P. G. M. Wuts, Wiley-Interscience. For example, for the deprotection of tert-butoxycarbonyl group, an acid such as p-toluenesulfonic acid monohydrate may be used in a suitable solvent such as acetonitrile to provide a compound of Formula I.

Scheme 3

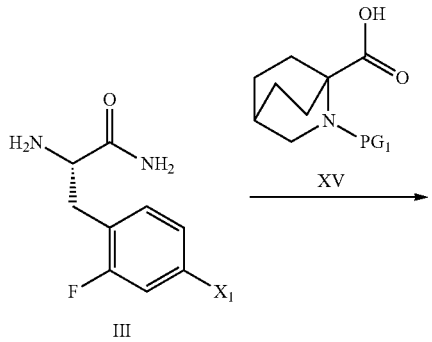

III

-continued

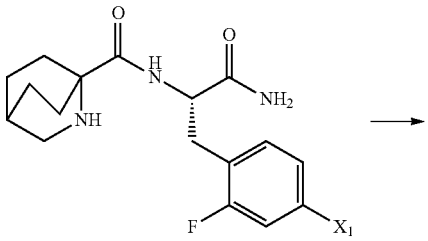

XVI

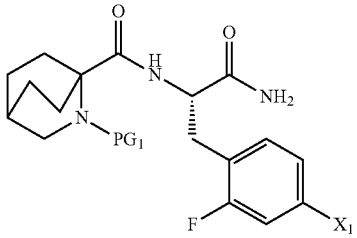

XVII

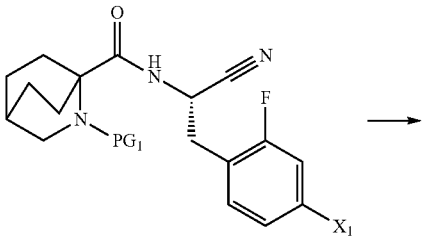

XVIII

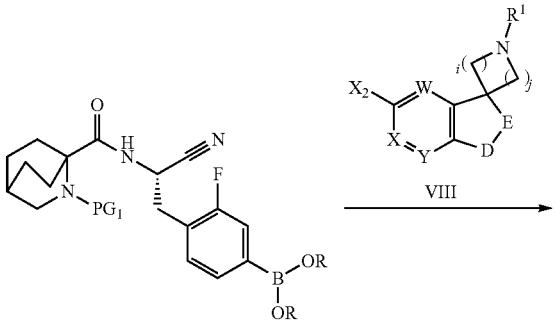

XIX

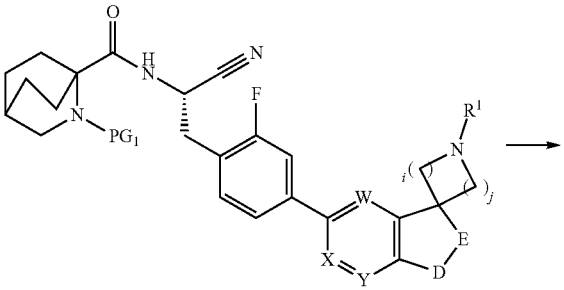

XX

-continued

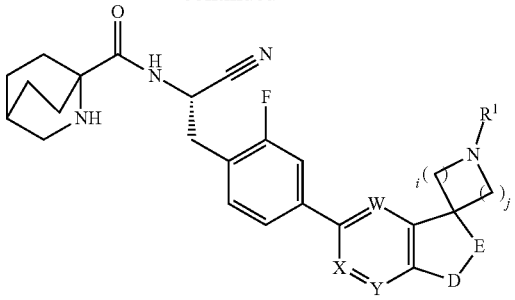

I $X_1$ = I, Br
$X_2$ = Cl, Br

As illustrated in Scheme 3 reacting an acid of Formula XV, wherein $PG_1$ represents a protecting group (e.g. tert-butoxycarbonyl) using standard literature procedures for the formation of an amide, for example in the presence of a base such as N-methylmorpholine and an activating agent such as 1-propanephosphonic acid cyclic anhydride (PPA) with an amine of Formula III in a suitable solvent, provides a compound of Formula XVI. Standard peptide coupling reactions known in the art (see for example M. Bodanszky, 1984, The Practice of Peptide Synthesis, Springer-Verlag) may be employed in these syntheses.

The protection and deprotection of functional groups is described in 'Protective Groups in Organic Synthesis', T. W. Greene and P. G. M. Wuts, Wiley-Interscience. For example, for the protection of an amine of Formula XVI, di-tert-butyl dicarbonate may be used in a suitable solvent such as dichloromethane to provide a compound of Formula XVII.

Dehydration of an amide such as in a compound of Formula XVII to the corresponding nitrile of Formula XVIII may be carried out by use of a dehydration agent such as (methoxycarbonylsulfamoyl)triethyl ammonium hydroxide, in a suitable solvent such as dichloromethane (DCM).

Compounds of Formula XVIII ($X_1$=I, Br) can be converted into the corresponding boronic acid derivatives XIX, wherein R can be H or lower alkyl independently and the residues R can form a ring. For example, XVIII can be reacted with bis(pinacolato)diboron in the presence of a suitable catalyst such as [1,1'-bis(diphenylphosphino)ferrocene]dichloropalladium(II), and a suitable base such as potassium acetate or sodium, potassium or cesium carbonate or phosphate, in a suitable solvent such as dioxan, dimethylformamide (DMF), or dichloromethane (DCM) to yield the boronic acid derivatives XIX.

These can be reacted in a (transition) metal catalyzed reaction of a compound of Formula VIII ($X_2$=Cl, Br). Coupling of these halogenides VIII provide a compound of Formula XX. For example, reaction of these halogenides with a boronic acid or the corresponding boronic acid ester XIX, in a suitable solvent such as dioxane, in the presence of a suitable catalyst such as 1,1'-bis(di-tert-butylphosphino) ferrocene palladium dichloride and a suitable base such as sodium, potassium or cesium carbonate, provides a compound of Formula XX.

The protection and deprotection of functional groups is described in 'Protective Groups in Organic Synthesis', T. W. Greene and P. G. M. Wuts, Wiley-Interscience. For example, for the deprotection of tert-butoxycarbonyl group, an acid such as p-toluenesulfonic acid monohydrate may be used in a suitable solvent such as acetonitrile to provide a compound of Formula I.

Scheme 4

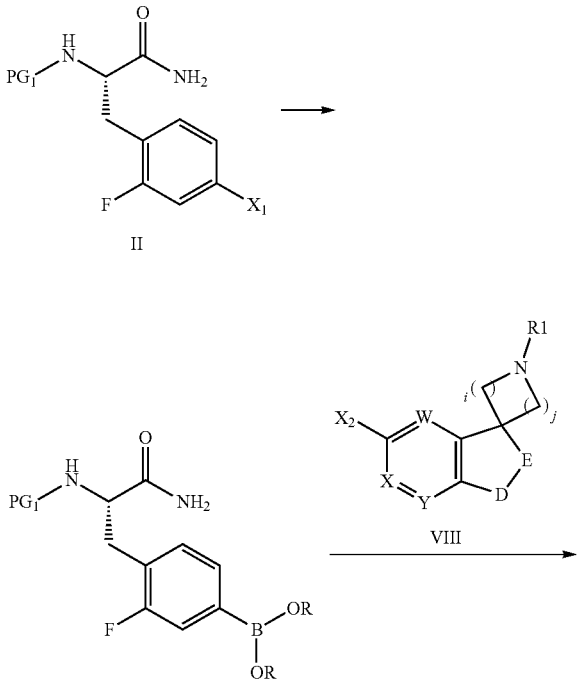

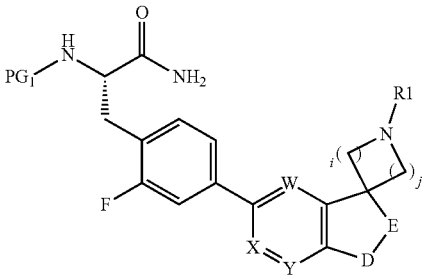

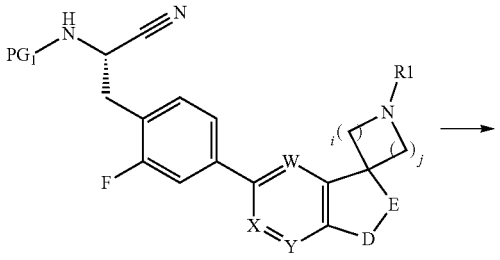

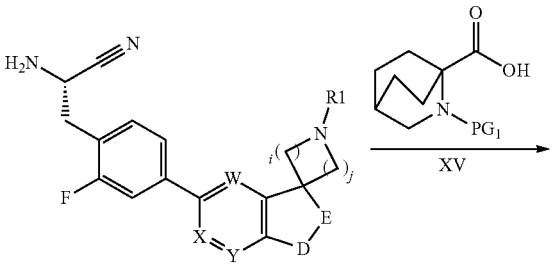

-continued

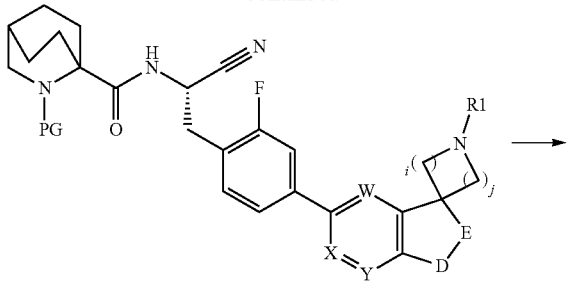

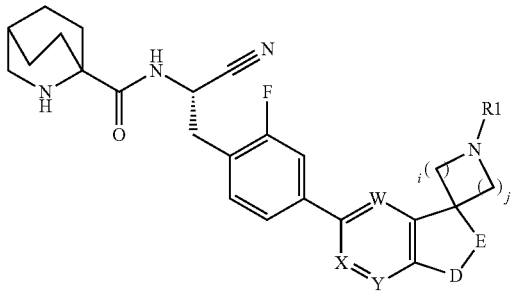

$X_1$ = I, Br
$X_2$ = Cl, Br

As illustrated in Scheme 4 compound of Formula II can be converted into the corresponding boronic acid derivatives XXI, wherein R can be H or lower alkyl independently and the residues R can form a ring. For example, II can be reacted with bis(neopentyl glycolato)diboron in the presence of a suitable catalyst such as [1,1'-bis(diphenylphosphino) ferrocene]dichloropalladium(II), and a suitable base such as potassium acetate or sodium, potassium or cesium carbonate or phosphate, in a suitable solvent such as dioxan, dimethylformamide (DMF), or dichloromethane (DCM) to yield the boronic acid derivatives XXI.

These can be reacted in a (transition) metal catalyzed reaction of a compound of Formula VIII analogous to the reaction procedure described in Scheme 1 to yield a compound of Formula XXII.

Dehydration of an amide such as a compound of Formula XXII to the corresponding nitrile of Formula XXIII may be carried out by use of a dehydration agent such as (methoxycarbonylsulfamoyl)triethyl ammonium hydroxide, in a suitable solvent such as dichloromethane (DCM).

The protection and deprotection of functional groups is described in 'Protective Groups in Organic Synthesis', T. W. Greene and P. G. M. Wuts, Wiley-Interscience. For example, for the deprotection of tert-butoxycarbonyl, an acid such as p-toluenesulfonic acid monohydrate may be used in a suitable solvent such as acetonitrile to provide a compound of Formula XXIV.

Reacting an acid of Formula XV, wherein PG1 represents a protecting group (e.g. tert-butoxycarbonyl) using standard literature procedures for the formation of an amide, for example in the presence of a base such as N-methylmorpholine and an activating agent such as 1-propanephosphonic acid cyclic anhydride (PPA), with an amine of Formula XXIV in a suitable solvent, provides a compound of Formula XXV. Standard peptide coupling reactions known in the art (see for example M. Bodanszky, 1984, The Practice of Peptide Synthesis, Springer-Verlag) may be employed in these syntheses.

The protection and deprotection of functional groups is described in 'Protective Groups in Organic Synthesis', T. W. Greene and P. G. M. Wuts, Wiley-Interscience. For example, for the deprotection of tert-butoxycarbonyl, an acid such as p-toluenesulfonic acid monohydrate may be used in a suitable solvent such as acetonitrile to provide a compound of Formula I.

Further modifications of compounds of Formula I by methods known in the art and illustrated in the Examples below, may be used to prepare additional compounds of the invention.

SYNTHETIC EXAMPLES

The following are representative compounds of the invention which can be made by the general synthetic schemes, the examples, and known methods in the art. Starting materials and intermediates were either commercially available and purchased from catalogues of ABCR, ACROS, ABLOCK PHARMATECH, ACTIVATE, ALDRICH, APOLLO SCIENTIFIC, ARK PHARM INC, ATLANTIC SCIENTIFIC TECHNOLOGY, BETAPHARM, BEFARM, CHEMBRIDGE CORPORATION, CNH-TECH, ENAMINE LTD, GOLDENBRIDGE PHARMA INC, GVK BIO, MERCACHEM, MOLBRIDGE, WUXI APPTEC, ZERENEX or were synthesized according to literature or as described below in "Synthesis of starting materials/educts"

Liquid chromatography-mass spectroscopy (LCMS) retention time and observed m/z data for the compounds below are obtained by one of the following methods:

LC-MS Method V001_007

| Device-Description | Waters Alliance with DAD and MSD | | | |
|---|---|---|---|---|
| Column | Waters XBridge C18 | | | |
| Column Dimension | 4.6 × 30 mm | | | |
| Particle Size | 3.5 μm | | | |
| Gradient/Solvent Time [min] | % Sol [$H_2O$, 0.1% TFA] | % Sol [Methanol] | Flow [ml/min] | Temp [° C.] |
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

LC-MS Method V003_003

| Device-Description | Waters Alliance with DAD and MSD | | | |
|---|---|---|---|---|
| Column | Waters XBridge C18 | | | |
| Column Dimension | 4.6 × 30 mm | | | |
| Particle Size | 3.5 μm | | | |
| Gradient/Solvent Time [min] | % Sol [$H_2O$, 0.1% $NH_3$] | % Sol [Methanol] | Flow [ml/min] | Temp [° C.] |
| 0.0 | 95 | 5 | 4 | 60 |
| 0.2 | 95 | 5 | 4 | 60 |
| 1.5 | 0 | 100 | 4 | 60 |
| 1.75 | 0 | 100 | 4 | 60 |

LC-MS Method V011_S01

| Device-Description | Waters Alliance with DAD and MSD | | | |
|---|---|---|---|---|
| Column | Waters XBridge C18 | | | |
| Column Dimension | 4.6 × 30 mm | | | |
| Particle Size | 3.5 μm | | | |
| Gradient/Solvent time [min] | % Sol [$H_2O$, 0.1% $NH_3$] | % Sol [Acetonitrile] | Flow [ml/min] | Temp [° C.] |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

LC-MS Method V012_S01

| Device-Description | Waters Alliance with DAD and MSD | | | |
|---|---|---|---|---|
| Column | Waters XBridge C18 | | | |
| Column Dimension | 4.6 × 30 mm | | | |
| Particle Size | 3.5 μm | | | |
| Gradient/Solvent time [min] | % Sol [$H_2O$, 0.1% TFA] | % Sol [Acetonitrile] | Flow [ml/min] | Temp [° C.] |
| 0.0 | 97 | 3 | 5 | 60 |
| 0.2 | 97 | 3 | 5 | 60 |
| 1.6 | 0 | 100 | 5 | 60 |
| 1.7 | 0 | 100 | 5 | 60 |

LC-MS Method X001_004

| Device-Description | Waters Acquity with DAD and MSD | | | |
|---|---|---|---|---|
| Column | Waters XBridge C18 | | | |
| Column Dimension | 2.1 × 20 mm | | | |
| Particle Size | 2.5 μm | | | |
| Gradient/Solvent Time [min] | % Sol [$H_2O$, 0.10% TFA] | % Sol [Methanol] | Flow [ml/min] | Temp [° C.] |
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

LC-MS Method X011_S03

| Device-Description | Waters Acquity with DAD and MSD | | | |
|---|---|---|---|---|
| Column | Waters Xbridge BEH C18 | | | |
| Column Dimension | 2.1 × 30 mm | | | |
| Particle Size | 1.7 μm | | | |
| Solvent Gradient time [min] | % Sol [H2O, 0.1% NH3] | % Sol [Acetonitrile] | Flow [ml/min] | Temp [° C.] |
| 0.00 | 95 | 5 | 1.3 | 60 |
| 0.02 | 95 | 5 | 1.3 | 60 |
| 1.00 | 0 | 100 | 1.3 | 60 |
| 1.10 | 0 | 100 | 1.3 | 60 |

LC-MS Method X012_S02

| Device-Description | Waters Acquity with DAD and MSD | | | |
|---|---|---|---|---|
| Column | Waters XBridge BEH C18 | | | |
| Column Dimension | 2.1 × 30 mm | | | |
| Particle Size | 1.7 μm | | | |
| Solvent Gradient time [min] | % Sol [H2O, 0.1% TFA] | % Sol [Acetonitrile] | Flow [ml/min] | Temp [° C.] |
| 0.0 | 99 | 1 | 1.3 | 60 |
| 0.02 | 99 | 1 | 1.3 | 60 |
| 1.00 | 0 | 100 | 1.3 | 60 |
| 1.10 | 0 | 100 | 1.3 | 60 |

LC-MS Method Z011_S03

| Device-Description | Agilent 1200 with DAD and MSD | | | |
|---|---|---|---|---|
| Column | Waters XBridge C18 | | | |
| Column Dimension | 3 × 30 mm | | | |
| Particle Size | 2.5 μm | | | |
| Gradient/Solvent Time [min] | % Sol [$H_2O$, 0.1% NH3] | % Sol [Acetonitrile] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z012_S04

| Device-Description | Agilent 1200 with DAD and MSD | | | |
|---|---|---|---|---|
| Column | Waters XBridge C18 | | | |
| Column Dimension | 3 × 30 mm | | | |
| Particle Size | 2.5 μm | | | |
| Gradient/Solvent Time [min] | % Sol [$H_2O$, 0.1% NH3] | % Sol [Acetonitrile] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z018_S04

| Device-Description | Agilent 1200 with DAD and MSD | | | |
|---|---|---|---|---|
| Column | Waters Sunfire C18 | | | |
| Column Dimension | 3 × 30 mm | | | |
| Particle Size | 2.5 μm | | | |
| Solvent Gradient time [min] | % Sol [$H_2O$, 0.1% TFA] | % Sol [Acetonitrile] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z020_S01

| Device-Description | Agilent 1200 with DAD and MSD | | | |
|---|---|---|---|---|
| Column | Waters Sunfire C18 | | | |
| Column Dimension | 3 × 30 mm | | | |
| Particle Size | 2.5 μm | | | |
| Solvent Gradient time [min] | % Sol [$H_2O$, 0.1% FA] | % Sol [Acetonitrile] | Flow [ml/min] | Temp [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

LC-MS Method Z021_S01

| Device-Description | Agilent 1200 with DAD and MSD | | | |
|---|---|---|---|---|
| Column | XBridge C18 | | | |
| Column Dimension | 3 × 30 mm | | | |
| Particle Size | 2.5 μm | | | |
| Solvent Gradient time [min] | % Sol [$H_2O$, 0.1% FA] | % Sol [Acetonitrile] | Flow [ml/min] | Temp [° C.] |
| 0.00 | 97 | 3 | 2.2 | 60 |
| 0.20 | 97 | 3 | 2.2 | 60 |

-continued

| Device-Description | Agilent 1200 with DAD and MSD | | | |
|---|---|---|---|---|
| Column | XBridge C18 | | | |
| Column Dimension | 3 × 30 mm | | | |
| Particle Size | 2.5 μm | | | |
| Solvent Gradient time [min] | % Sol [$H_2O$, 0.1% FA] | % Sol [Acetonitrile] | Flow [ml/min] | Temp [° C.] |
| 1.20 | 0 | 100 | 2.2 | 60 |
| 1.25 | 0 | 100 | 3 | 60 |
| 1.40 | 0 | 100 | 3 | 60 |

Synthesis Methods

Method A

Synthesis of (1S,2S,4R)—N-[(1S)-1-cyano-2-[2-fluoro-4-[1'-(oxetan-3-yl)spiro[1H-isobenzofuran-3,4'-piperidine]-5-yl]phenyl]ethyl]-3-azabicyclo[2.2.1]heptane-2-carboxamide

Example 1

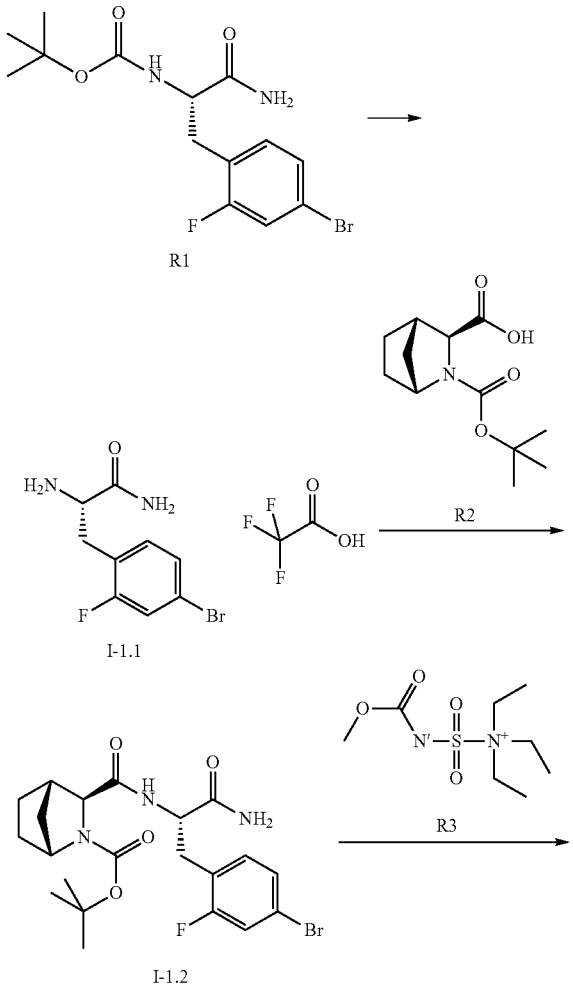

-continued

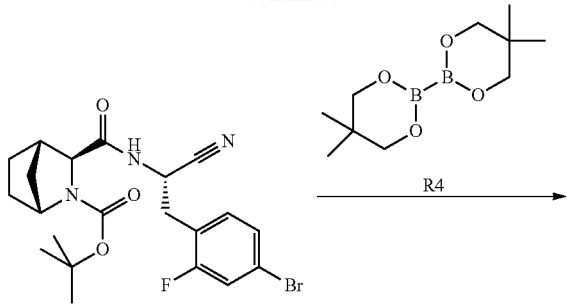

I-1.3

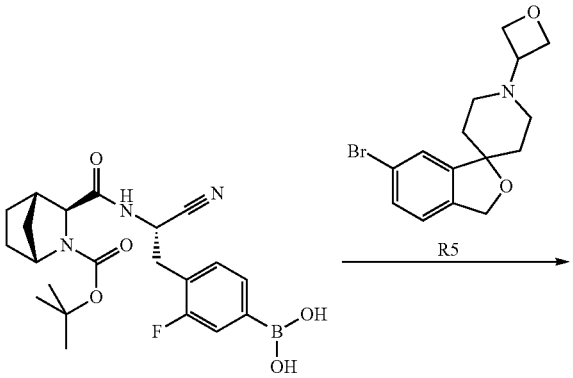

I-1.4

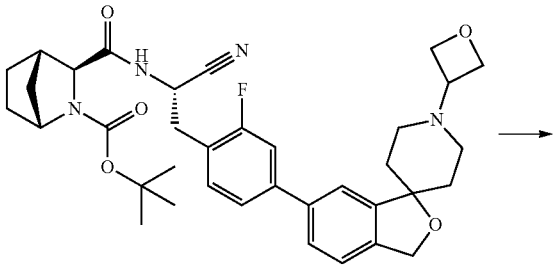

I-1.5

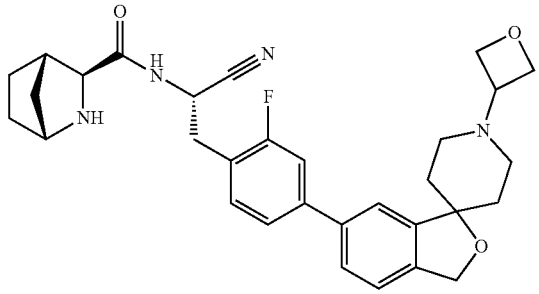

Example 1

Step 1: Synthesis of Intermediate I-1.1

To R1 (20.00 g, 55.37 mmol) in dichloromethane (50 mL) is added trifluoroacetic acid (17.09 mL, 221.48 mmol) and the reaction mixture is stirred overnight at r.t. The reaction mixture is concentrated, the residue is dissolved in dichloromethane (15 mL) and diisopropyl ether (140 mL). The precipitate is filtered off, washed with diisopropyl ether and dried to provide I-1.1 as TFA salt.

Yield 99%, m/z 261 [M+H]+, rt 0.50 min, LC-MS Method Z018_S04.

Step 2: Synthesis of Intermediate I-1.2

To R2 (13.86 g, 55.72 mmol) in DMF (65 mL) is added DIPEA (9.02 mL, 50.67 mmol) and cooled down to 5° C. TBTU (17.89 g, 55.72 mmol) is added and the reaction mixture is stirred for 15 minutes. Afterwards I-1.1 (TFA salt) (19.0 g, 50.65 mmol), DMF (65 mL) and DIPEA (13.52 mL, 75.98 mmol) are added and the reaction mixture is stirred overnight at r.t. The reaction mixture is diluted with ethyl acetate and extracted with water. The aqueous layer is extracted with ethyl acetate. The combined organic layers are washed with water, 1 mol/L aqueous hydrochloric acid, water, aqueous sodium hydrogen carbonate solution (5%) and again with water. The organic layer is dried over $MgSO_4$, filtered and concentrated in vacuo. The crude residue is purified by flash chromatography (eluent: dichloromethane/methanol 95:5).

Yield 82%, m/z 484 [M+H]+, rt 0.91 min, LC-MS Method Z018_S04.

Step 3: Synthesis of Intermediate I-1.3

To I-1.2 (20.0 g, 41.29 mmol) in dichloromethane (200 mL) is added R3 (19.68 g, 82.58 mmol) and the reaction mixture is stirred overnight at r.t. The reaction mixture is concentrated in vacuo, the residue is dissolved in ethyl acetate and extracted with water, 1 mol/L aqueous acetic acid, and water. The organic layer is dried over $MgSO_4$, filtered and concentrated in vacuo. The residue is recrystallized from acetonitrile and filtered off.

Yield 71%, m/z 466 [M+H]+, rt 0.98 min, LC-MS Method Z018_S04.

Step 4: Synthesis of Intermediate I-1.4

To I-1.3 (1.5 g, 3.22 mmol) in dioxane (20 mL) R4 (799.22 mg, 3.54 mmol), potassium acetate (0.947 g, 9.65 mmol) and [1,1'-bis(diphenylphosphino)ferrocene]dichloropalladium(II), complex with dichloromethane (1:1) (52.54 mg, 0.064 mmol) are added. The reaction mixture is purged with nitrogen and heated to 70° C. for 1.5 h. The reaction mixture is diluted with dichloromethane and water. The organic layer is separated and concentrated in vacuo. The residue is purified by reversed phase HPLC.

Yield 94% m/z 332 [M+H-Boc]+, rt 0.96 min, LC-MS Method Z020_S01.

Step 5: Synthesis of Intermediate I-1.5

To I-1.4 (400.0 mg, 0.93 mmol) in acetonitrile (18 mL) is added R5 (301.0 mg, 0.93 mmol) and mixture is purged with argon. Sodium carbonate aqueous solution 2 mol/L (928 μL, 1.86 mmol) and 1,1'-bis(di-tert-butylphosphino)ferrocene palladium dichloride (60.5 mg, 0.09 mmol) are added, reaction mixture is purged again with argon and stirred at 80° C. in the microwave reactor for 45 minutes. The reaction mixture is diluted with saturated sodium hydrogen carbonate solution, and extracted with ethyl acetate several times. The organic layer is washed with brine, dried over $Na_2SO_4$, filtered and concentrated in vacuo. The crude residue is purified by silica gel column chromatography (DCM: MeOH=98:2 to 92:8) to afford I-1.5.

Yield 79% m/z 631 [M+H]+, rt 1.09 min, LC-MS Method Z011_S03.

Alternative Synthesis of Intermediate I-1.5

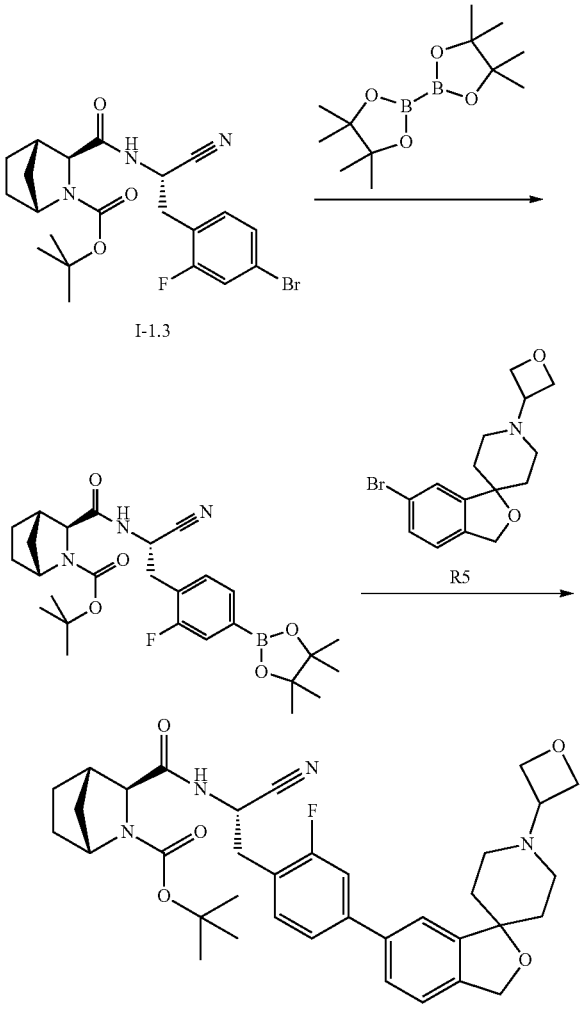

Synthesis of Intermediate I-1.4.1

To I-1.3 (20 g, 42.89 mmol) in dioxane (255 mL) bis (pinacolato)diboron (13.07 g, 51.46 mmol), potassium acetate (12.63 g, 128.66 mmol) and [1,1'-bis(diphenylphosphino)ferrocene]dichloropalladium(II), complex with dichloromethane (1:1) (1.75 g, 2.14 mmol) are added. The mixture is purged with nitrogen for 5 minutes, heated to 70° C. and stirred overnight at this temperature. The reaction mixture is diluted with dichloromethane and water. The organic layer is separated and concentrated in vacuo. The residue is purified by silica gel column chromatography (petroleum ether:EtOAc=92:8 to 34:66).

Yield 64% m/z 332 $[M+H-Boc-((CH_3)_2CH)_2]+$, rt 0.73 min, LC-MS Method Z011_S03.

Synthesis of Intermediate I-1.5

To I-1.4.1 (3.96 g, 7.71 mmol) in acetonitrile (60 mL) is added R5 (2.50 g, 7.71 mmol) and mixture is purged with argon. Sodium carbonate aqueous solution 2 mol/L (7.71 mL, 15.42 mmol) and 1,1'-bis(di-tert-butylphosphino)ferrocene palladium dichloride (502.6 mg, 0.77 mmol) are added, reaction mixture is purged again with argon and stirred at 80° C. for 90 minutes. The reaction mixture is diluted with saturated sodium hydrogen carbonate solution, and extracted with ethyl acetate several times. The organic layer is washed with brine, dried over $Na_2SO_4$, filtered and concentrated in vacuo. The crude residue is purified by silica gel column chromatography (DCM:MeOH=99:1 to 94:6) to afford I-1.5.

Yield 75% m/z 631 [M+H]+, rt 1.09 min, LC-MS Method Z011_S03.

The following intermediates as shown in Table 1 are synthesized in a similar fashion from the intermediate I-1.4 and appropriate educts:

TABLE 1

| Intermediate | Educt | Structure of Intermediate | m/z [M +H]+ | rt (min) | LC-MS method |
|---|---|---|---|---|---|
| I-1.5.1 | R6 | 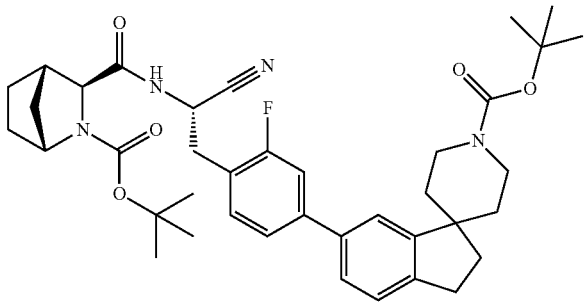 | 517 [M-Boc-t.but + H]+ | 1.29 | Z012_S04 |

TABLE 1-continued
| Intermediate | Educt | Structure of Intermediate | m/z [M +H]+ | rt (min) | LC-MS method |
|---|---|---|---|---|---|
| I-1.5.2 | R8 | 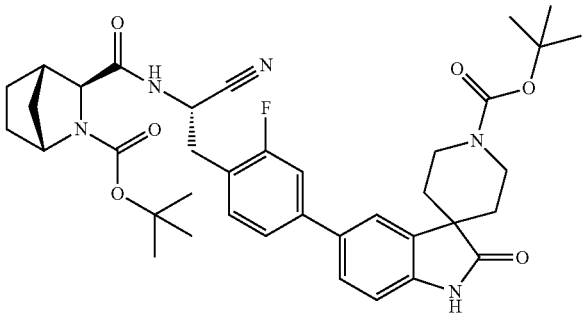 | 532 [M-Boc-t.but + H]+ | 1.14 | Z012_S04 |
| I-1.5.3 | R9 | 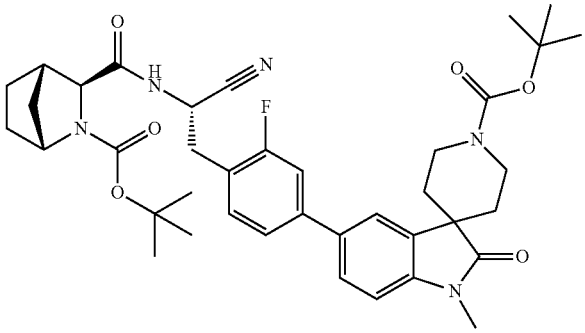 | 546 [M-Boc-t.but + H]+ | 1.19 | Z012_S04 |
| I-1.5.4 | R10 | 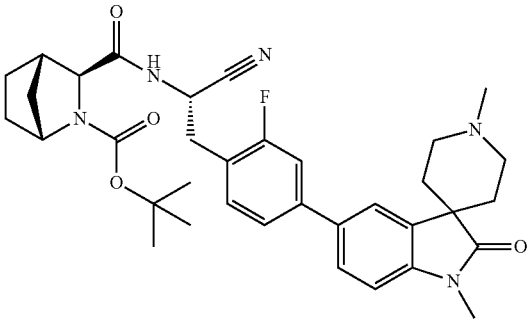 | 616 | 0.95 | Z012_S04 |
| I-1.5.5 | R10.1 | 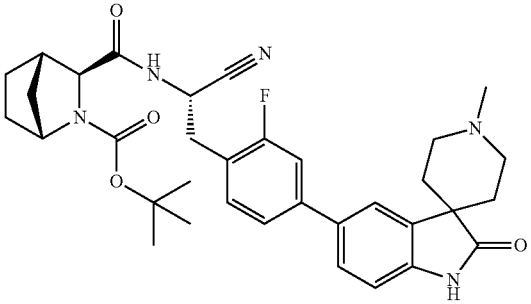 | 602 | 0.91 | Z012_S04 |

TABLE 1-continued
| Intermediate | Educt | Structure of Intermediate | m/z [M +H]+ | rt (min) | LC-MS method |
|---|---|---|---|---|---|
| I-1.5.6 | I-7.2 | 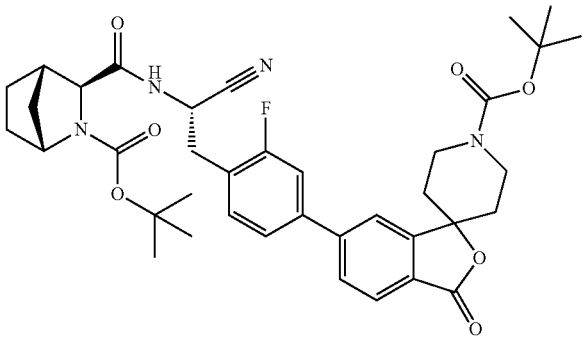 | 589 [M-Boc + H]+ | 1.19 | Z012_S04 |
| I-1.5.7 | R10.2 | 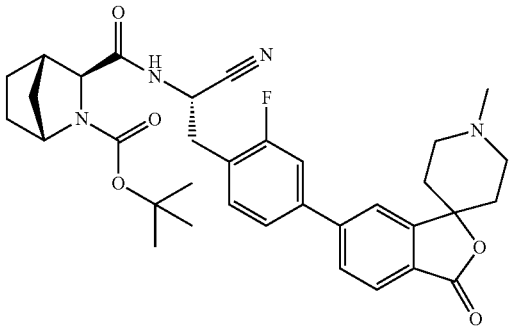 | 603 | 0.94 | Z012_S04 |
| I-1.5.8 | I-7.2.1 | 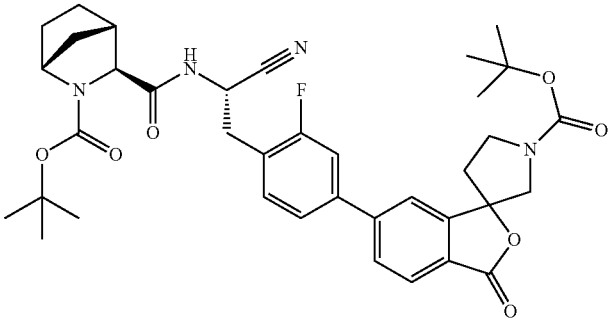 | 575 [M-Boc + H]+ | 1.15 | Z011_S03 |
| I-1.5.9 | R10.3 | 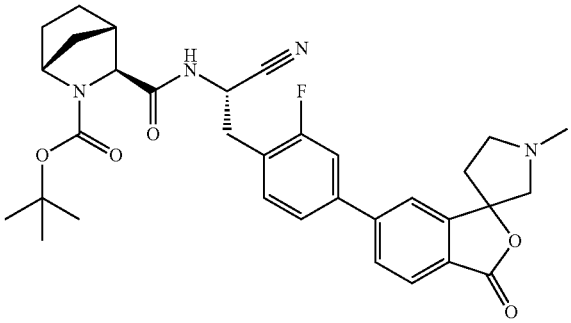 | 589 | 0.95 | Z012_S04 |

TABLE 1-continued
| Intermediate | Educt | Structure of Intermediate | m/z [M +H]+ | rt (min) | LC-MS method |
|---|---|---|---|---|---|
| I-1.5.10 | I-7.2.2 | 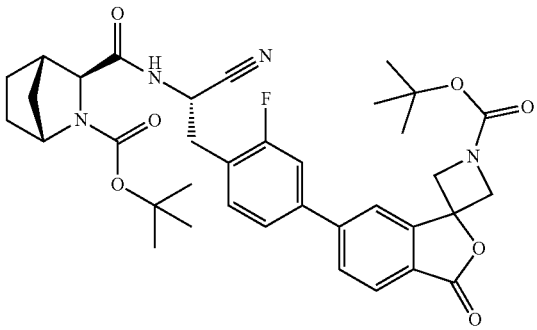 | 561 [M-Boc + H]+ | 1.17 | Z012_S04 |
| I-1.5.11 | R10.4 | 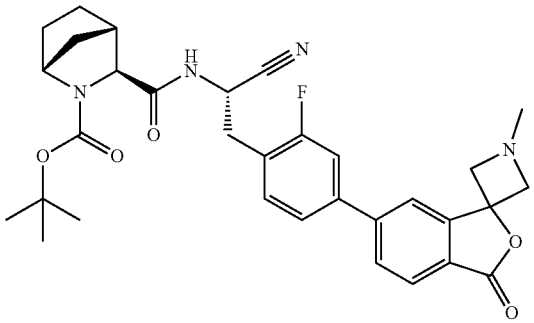 | 575 | 1.04 | Z012_S03 |
| I-1.5.12 | I-7.4 | 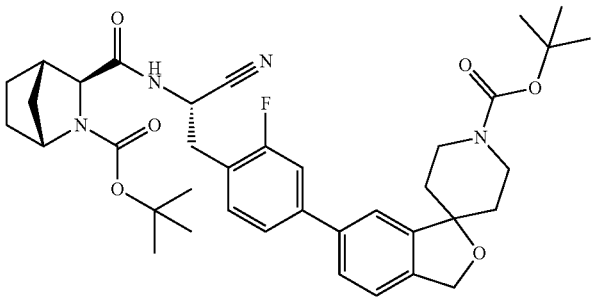 | 575 [M-Boc + H]+ | 1.24 | Z012_S03 |
| I-1.5.13 | R10.5 | 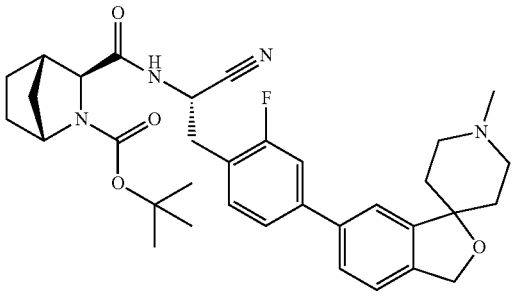 | 589 | 1.12 | Z012_S03 |
| I-1.5.14 | R7 | 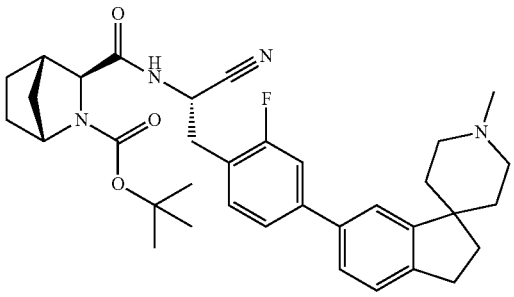 | 587 | 1.19 | Z012_S03 |

TABLE 1-continued
| Intermediate | Educt | Structure of Intermediate | m/z [M +H]+ | rt (min) | LC-MS method |
|---|---|---|---|---|---|
| I-1.5.15 | R12 | 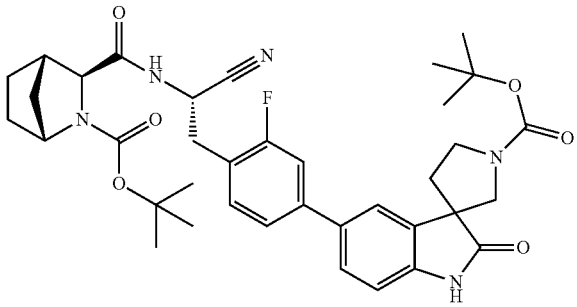 | 574 [M-Boc + H]+ | 1.10 | Z011_S03 |
| I-1.5.16 | R10.6 | 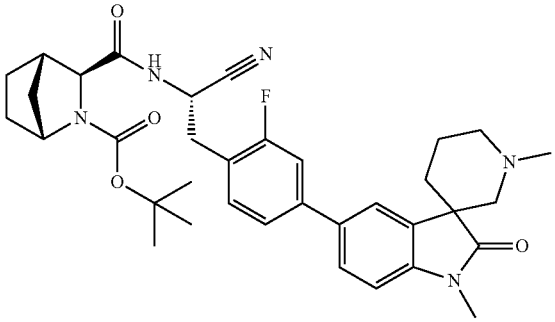 | 615 | 0.80 | Z020_S01 |
| I-1.5.17 | R14 | 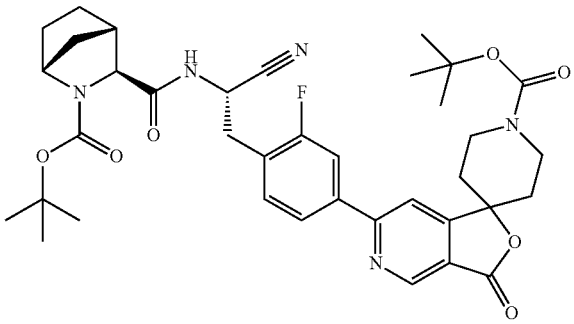 | 590 [M-Boc + H]+ | 1.16 | Z011_S03 |
| I-1.5.18 | R10.7 | 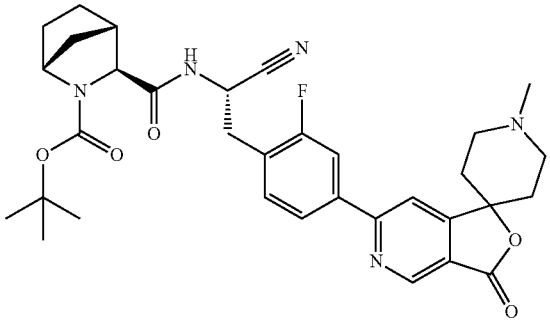 | 604 | 1.04 | Z011_S03 |

TABLE 1-continued
| Intermediate | Educt | Structure of Intermediate | m/z [M +H]+ | rt (min) | LC-MS method |
|---|---|---|---|---|---|
| I-1.5.19 | I-11.1.1 | 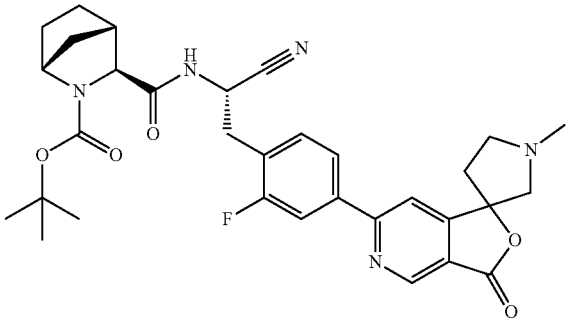 | 590 | 1.02 | Z011_S03 |
| I-1.5.20 | R15 | 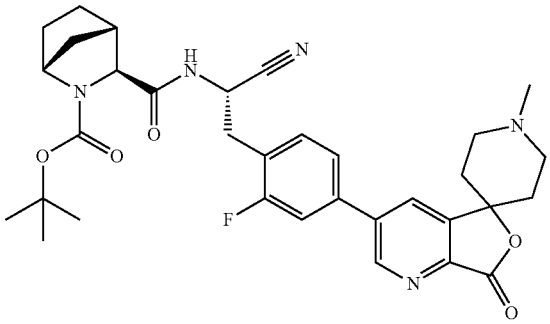 | 604 | 1.03 | Z011_S03 |
| I-1.5.21 | R16 | 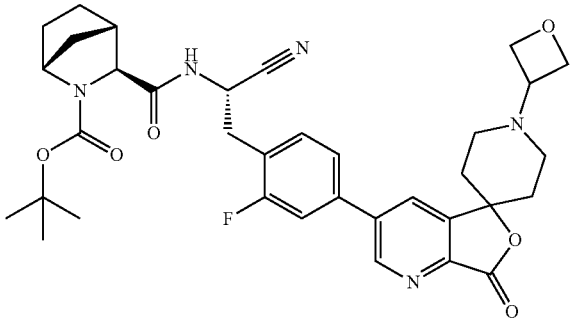 | 546 [M-Boc + H]+ | 1.00 | Z011_S03 |
| I-1.5.22 | R17 | 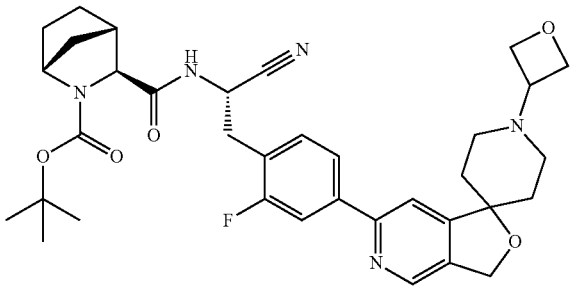 | 632 | 1.03 | Z011_S03 |

TABLE 1-continued

| Intermediate | Educt | Structure of Intermediate | m/z [M +H]+ | rt (min) | LC-MS method |
|---|---|---|---|---|---|
| I-1.5.23 | R18 | 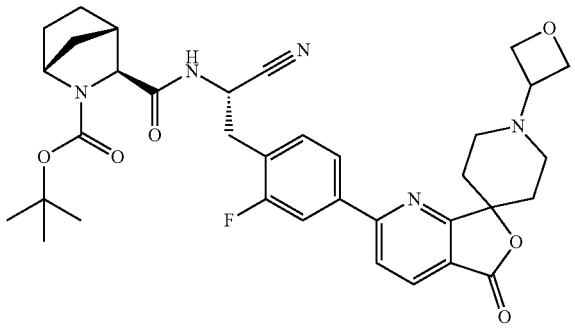 | 646 | 0.90 | Z011_S03 |
| I-1.5.24 | R19 | 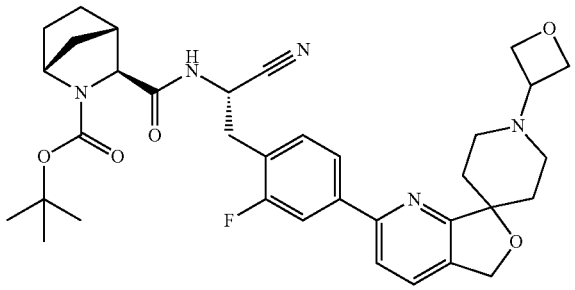 | 632 | 1.04 | Z011_S03 |

Step 6: Synthesis of Example 1

To I-1.5 (3.64 g, 5.78 mmol) in acetonitrile (60 mL) is added p-toluenesulfonic acid monohydrate (5.49 g, 28.88 mmol) and reaction mixture is stirred overnight at r.t. The reaction mixture is diluted with saturated sodium hydrogen carbonate solution, and extracted with ethyl acetate several times. The organic layer is washed with brine, dried over $MgSO_4$, filtered and concentrated in vacuo. The crude residue is purified by reversed phase HPLC.

Yield 84% m/z 531 [M+H]+, rt 1.00 min, LC-MS Method Z011_S03.

Synthesis of (1S,2S,4R)—N-[(1S)-1-cyano-2-[2-fluoro-4-[1'-(oxetan-3-yl)spiro[3H-furo[3,4-c]pyridine-1,4'-piperidine]-6-yl]phenyl]ethyl]-3-azabicyclo[2.2.1]heptane-2-carboxamide Example 23

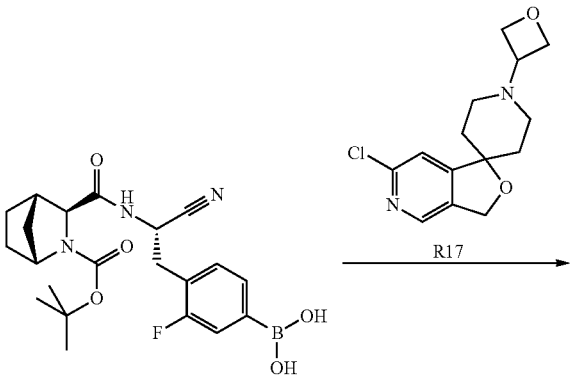

I-1.4

-continued

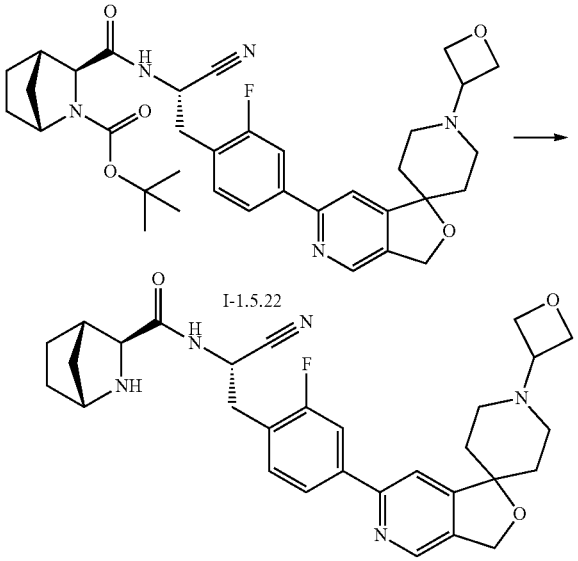

Example 23

Step 1: Synthesis of Intermediate I-1.5.22

To I-1.4 (92.2 mg, 0.17 mmol) in acetonitrile (3 mL) is added R17 (48.0 mg, 0.17 mmol) and mixture is purged with argon. Caesium carbonate aqueous solution 2 mol/L (171 μL, 0.34 mmol) and 1,1'-bis(di-tert-butylphosphino)ferrocene palladium dichloride (11.1 mg, 0.02 mmol) are added, reaction mixture is purged again with argon and stirred at 80° C. in the microwave reactor for 45 minutes. The reaction mixture is diluted with saturated sodium hydrogen carbonate solution, and extracted with ethyl acetate several times. The organic layer is washed with brine, dried over $MgSO_4$, filtered and concentrated in vacuo. The crude residue is purified by reversed phase HPLC to afford I-1.5.22.

Yield 52% m/z 632 [M+H]+, rt 1.04 min, LC-MS Method Z011_S03.

Step 2: Synthesis of Example 23

To I-1.5.22 (56.0 mg, 0.09 mmol) in acetonitrile (2 mL) is added p-toluenesulfonic acid monohydrate (84.3 mg, 0.44 mmol) and reaction mixture is stirred overnight at r.t. The reaction mixture is basicified with TEA, filtered through membrane filter and purified by reversed phase HPLC.

Yield 83% m/z 532 [M+H]+, rt 0.96 min, LC-MS Method Z011_S03.

Synthesis of (1S,2S,4R)—N-[(1S)-1-cyano-2-[2-fluoro-4-[1'-(oxetan-3-yl)spiro[5H-furo[3,4-b]pyridine-7,4'-piperidine]-2-yl]phenyl]ethyl]-3-azabicyclo[2.2.1]heptane-2-carboxamide Example 25

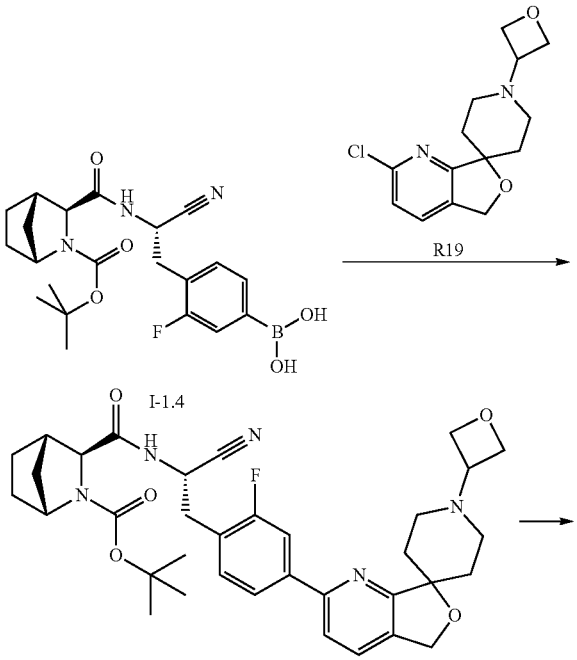

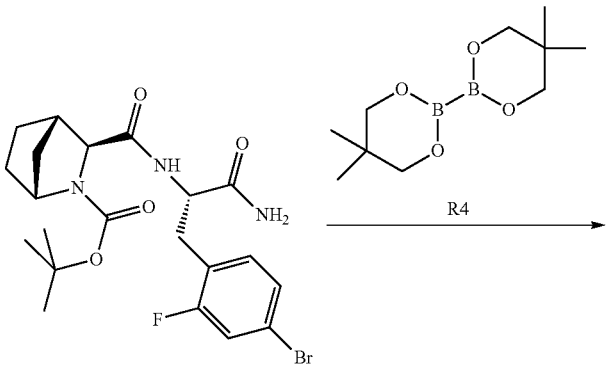

-continued

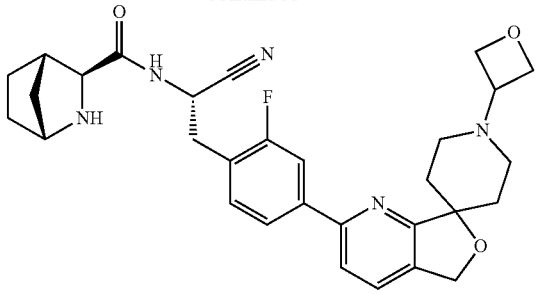

Example 25

Step 1: Synthesis of Intermediate I-1.5.24

To I-1.4 (2.304 g, 5.34 mmol) in acetonitrile (50 mL) is added R19 (1.50 g, 5.34 mmol) and mixture is purged with argon. Sodium carbonate aqueous solution 2 mol/L (5.343 mL, 10.69 mmol) and 1,1'-bis(di-tert-butylphosphino)ferrocene palladium dichloride (348.2 mg, 0.53 mmol) are added, reaction mixture is purged again with argon and stirred at 70° C. in the microwave reactor for 45 minutes. Additional amount of I-1.4 (150 mg, 0.35 mmol) is added and the reaction mixture is stirred at 70° C. for 25 minutes. The reaction mixture is diluted with saturated sodium hydrogen carbonate solution, and extracted with ethyl acetate several times. The organic layer is washed with brine, dried over $MgSO_4$, filtered and concentrated in vacuo. The crude residue is purified by silica gel column chromatography (DCM:MeOH=99:1 to 9:1) to afford I-1.5.24.

Yield 55% m/z 632 [M+H]+, rt 1.05 min, LC-MS Method Z011_S03.

Step 2: Synthesis of Example 25

To I-1.5.24 (1.85 g, 2.93 mmol) in acetonitrile (50 mL) is added p-toluenesulfonic acid monohydrate (2.78 g, 14.64 mmol) and reaction mixture is stirred overnight at r.t. The reaction mixture is diluted with saturated sodium hydrogen carbonate solution, and extracted with ethyl acetate several times. The organic layer is washed with brine, dried over $MgSO_4$, filtered and concentrated in vacuo. The crude residue is purified by reversed phase HPLC.

Yield 88% m/z 532 [M+H]+, rt 0.97 min, LC-MS Method Z011_S03.

Method B

Synthesis of (1S,2S,4R)—N-[(1S)-1-cyano-2-[2-fluoro-4-(1'-methylspiro[3H-furo[3,4-c]pyridine-1,4'-piperidine]-6-yl)phenyl]ethyl]-3-azabicyclo[2.2.1]heptane-2-carboxamide Example 26

-continued
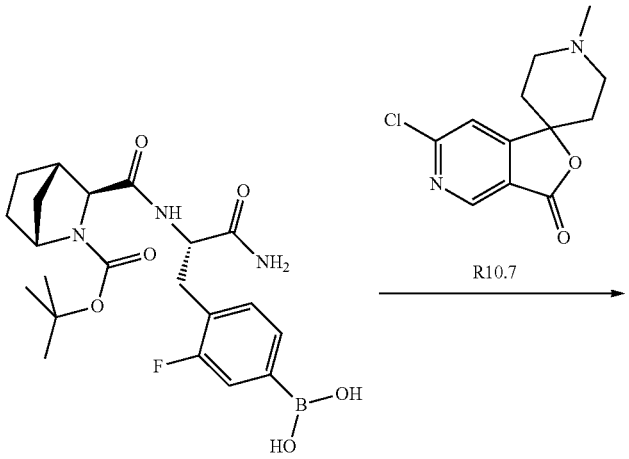
I-2.1
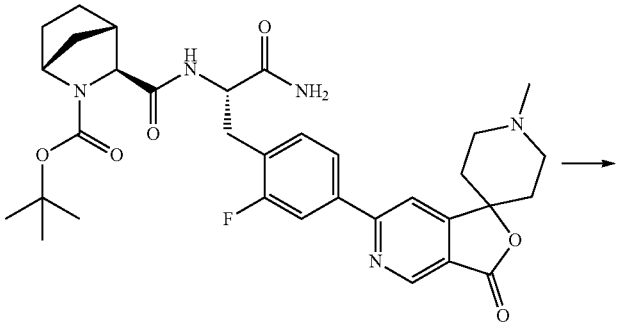
I-2.2
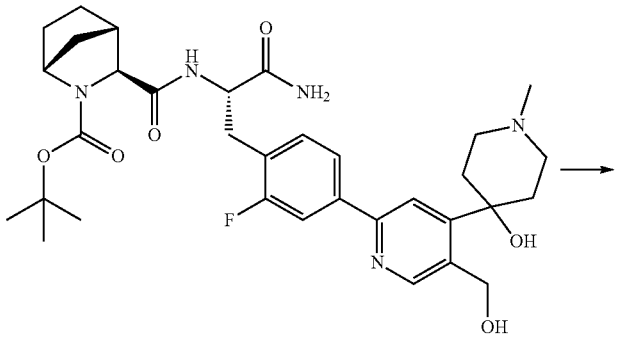
I-2.3
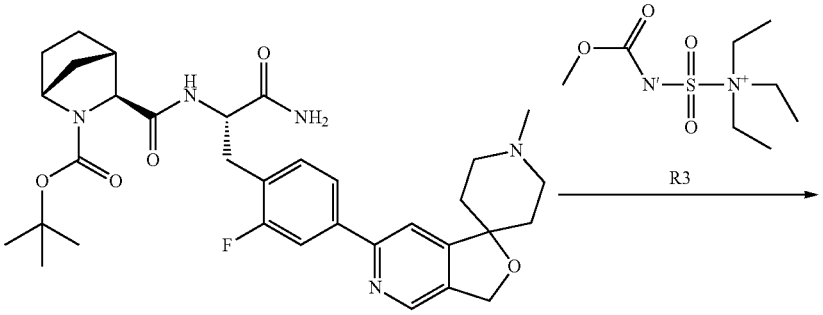
I-2.4

-continued

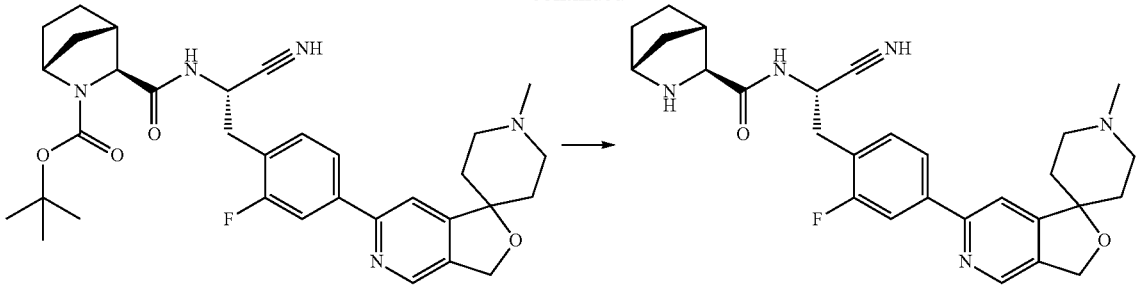

I-2.5 Example 26

Step 1: Synthesis of Intermediate I-2.1

To I-1.2 (1.0 g, 2.07 mmol) in dioxane (10 mL) R4 (512.99 mg, 2.27 mmol), potassium acetate (607.92 mg, 9.65 mmol) and [1,1'-bis(diphenylphosphino)ferrocene]dichloropalladium(II), complex with dichloromethane (1:1) (33.72 mg, 0.041 mmol) are added. The reaction mixture is purged with nitrogen and heated to 70° C. overnight. Again R4 (100 mg, 0.44 mmol) and [1,1'-bis(diphenylphosphino) ferrocene]dichloropalladium(II), complex with dichloromethane (1:1) (10 mg, 0.01 mmol) are added and the reaction mixture is stirred at 70° C. for 2 hours. The reaction mixture is diluted with saturated sodium hydrogen carbonate solution and extracted with ethyl acetate. The organic layer is washed with brine, dried over $MgSO_4$, filtered and concentrated in vacuo. The residue is purified by reversed phase HPLC.

Yield 50% m/z 450 [M+H]+.

Step 2: Synthesis of Intermediate I-2.2

To I-2.1 (204.46 mg, 0.46 mmol) in acetonitrile (4 mL) is added R10.7 (115 mg, 0.46 mmol) and mixture is purged with argon. Caesium carbonate solution 2 mol/L (455.09 μL, 0.91 mmol) and 1,1'-bis(di-tert-butylphosphino)ferrocene palladium dichloride (29.66 mg, 0.046 mmol) are added, reaction mixture is purged again with argon and stirred at 80° C. in the microwave reactor for 45 minutes. The reaction mixture is diluted with water, and extracted with ethyl acetate. The organic layer is washed with brine, dried over $MgSO_4$, filtered and concentrated in vacuo. The residue is purified by reversed phase HPLC.

Yield 75%.

Step 3: Synthesis of Intermediate I-2.3

To I-2.2 (212 mg, 0.34 mmol) in THF (5 mL) is added lithium borohydride (2 mol/L, 0.26 mL, 0.51 mmol) and reaction mixture is stirred for 3 hours at r.t. The reaction mixture is quenched with methanol, diluted with water and ethyl acetate. The organic layer is washed with sodium hydrogen carbonate solution and brine, dried over $Na_2SO_4$, filtered and concentrated in vacuo.

Yield 91%.

Step 4: Synthesis of Intermediate I-2.4

To I-2.3 (194 mg, 0.31 mmol) in THF (5 mL) are added TEA (0.22 mL, 1.55 mmol) and p-toluenesulfonic anhydride (121.43 mg, 0.37 mmol) at 0° C. The reaction mixture is allowed to come to r.t. and stirred overnight. The reaction mixture is quenched with water and concentrated in vacuo. The residue is diluted with sodium hydrogen carbonate solution and extracted with ethyl acetate. The organic layer is washed with brine, dried over $Na_2SO_4$, filtered and concentrated in vacuo. The residue is purified by reversed phase HPLC.

Yield 34% m/z 608 [M+H]+.

Step 5: Synthesis of Intermediate I-2.5

To I-2.4 (65 mg, 0.11 mmol) in dichloromethane (2.5 mL) is added R3 (63.72 mg, 0.27 mmol) and reaction mixture is stirred overnight at r.t. The reaction mixture is diluted with ethyl acetate and extracted with water. The organic layer is washed with brine, dried over $MgSO_4$, filtered and concentrated in vacuo.

Yield >95%.

Step 6: Synthesis of Example 26

To I-2.5 (68 mg, 0.10 mmol) in acetonitrile (2 mL) is added p-toluenesulfonic acid monohydrate (98.70 mg, 0.52 mmol) and reaction mixture is stirred for 1 h at r.t. The reaction mixture is basified with TEA and purified by reversed phase HPLC.

Yield 28% m/z 490 [M+H]+, rt 0.96 min, LC-MS Method Z011_S03.

Method C

Synthesis of N-[(1S)-1-cyano-2-[2-fluoro-4-[1'-(oxetan-3-yl)spiro[1H-isobenzofuran-3,4'-piperidine]-5-yl]phenyl]ethyl]-3-azabicyclo[2.2.2]octane-4-carboxamide Example 27

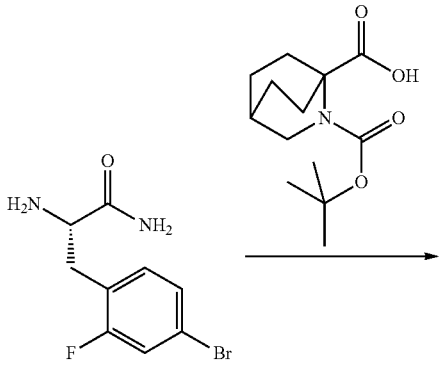

I-1.1

-continued

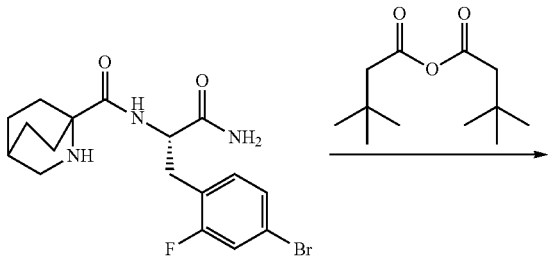

I-3.1

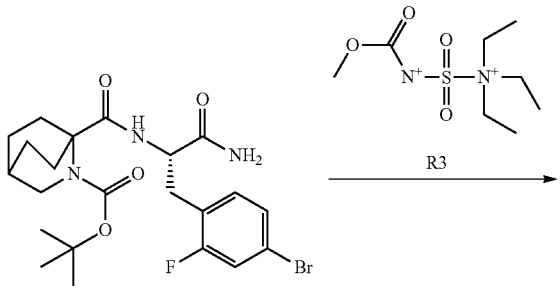

I-3.2

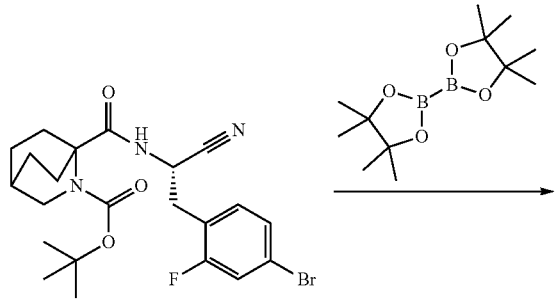

I-3.3

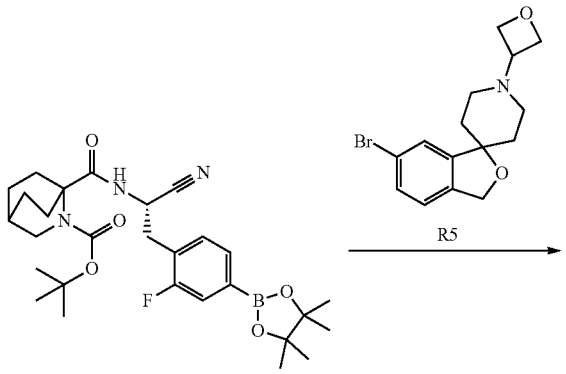

I-3.4

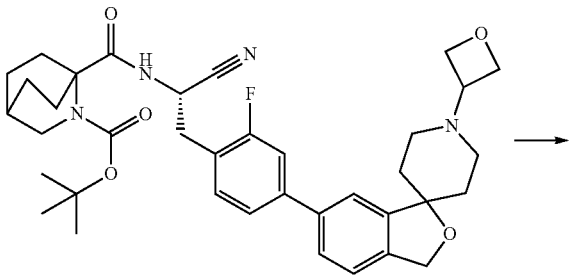

I-3.5

-continued

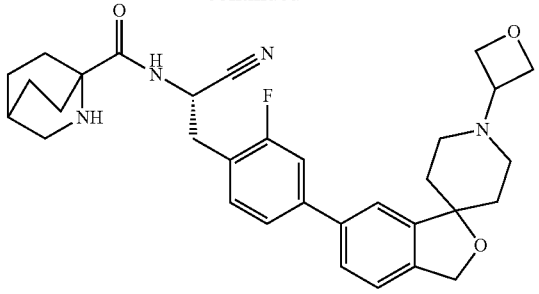

Example 27

Step 1: Synthesis of Intermediate I-3.1

To a cooled to 0° C. solution of I-1.1 (5.80 g, 22.2 mmol), 3-tert-butoxycarbonyl-3-azabicyclo[2.2.2]octane-4-carboxylic acid, prepared according to Radchenko et al. J. Org. Chem. 2009, 5541-5544 (5.67 g, 22.2 mmol) and N-methylmorpholine (12.2 mL, 111.0 mmol) in dry dichloromethane (67 mL) is added PPA (13.08 mL (50% in ethyl acetate), 22.2 mmol). The reaction mixture is allowed to reach r.t. and stirred overnight. The reaction mixture is diluted with saturated sodium hydrogen carbonate solution and extracted with dichloromethane several times. The organic layer is washed with brine, dried over $MgSO_4$, filtered and concentrated in vacuo to provide I-3.1, which was used in the next step without further purification.

Yield 73%, m/z 398/400 [M+H]+, rt 0.87 min, LC-MS Method Z011_S03.

Step 2: Synthesis of Intermediate I-3.2

To a cooled to 0° C. solution of I-3.1 (8.625 g, 21.66 mmol) in 300 mL of dry dichloromethane is added dropwise a solution of di-tert-butyl dicarbonate (6.26 g, 28.70 mmol) in 20 ml of dry dichloromethane. The reaction mixture is stirred for 2 h at 0° C., allowed to reach r.t., and stirred for 2 days. The reaction mixture is concentrated in vacuo to provide I-3.2 which was used in the next step without further purification.

Yield 98%, m/z 398/400 [M+H−Boc]+, rt 1.04 min, LC-MS Method Z011_S03.

Step 3: Synthesis of Intermediate I-3.3

To a suspension of I-3.2 (5.52 g, 11.07 mmol) in dry dichloromethane (70 mL) is added R3 (3.96 g, 16.60 mmol) in four portions and the reaction mixture is stirred overnight at r.t. Additional amount of R3 (791.0 mg, 3.32 mmol) is added and the reaction mixture is stirred for 6 h at r.t. Reaction mixture is diluted with dichloromethane, washed with 10% aqueous solution of tartaric acid, saturated sodium hydrogen carbonate solution, brine, dried over $MgSO_4$, filtered and concentrated in vacuo. Obtained residue is purified by silica gel column chromatography (petroleum ether:EtOAc=94:6 to 69:31) to provide I-3.3.

Yield 77% m/z 380/382 [M+H−Boc], rt 1.10 min, LC-MS Method Z011_S03.

Step 4: Synthesis of Intermediate I-3.4

To I-3.3 (3.61 g, 7.52 mmol) in dioxane (45 mL) bis (pinacolato)diboron (3.24 g, 12.78 mmol), potassium acetate (2.21 g, 22.55 mmol) and [1,1'-bis(diphenylphosphino)ferrocene]dichloropalladium(II), complex with dichloromethane (1:1) (61.4 mg, 0.08 mmol) are added. The mixture is purged with nitrogen for 5 minutes and heated at 70° C. for 3 h. The reaction mixture is diluted with water and extracted with dichloromethane. The organic layer is washed with brine, dried over $MgSO_4$, filtered and concentrated in vacuo. The residue is purified by silica gel column chromatography (petroleum ether:EtOAc=100:0 to 91:9) to provide I-3.4.

Yield 68% m/z 346 $[M+H-Boc-((CH_3)_2CH)_2]+$, rt 0.77 min, LC-MS Method Z011_S03.

Step 5: Synthesis of Intermediate I-3.5

To I-3.4 (1.14 g, 2.16 mmol) in acetonitrile (30 mL) is added R5 (0.70 g, 2.16 mmol) and mixture is purged with argon. Sodium carbonate aqueous solution 2 mol/L (2.16 mL, 4.32 mmol) and 1,1'-bis(di-tert-butylphosphino)ferrocene palladium dichloride (141.0 mg, 0.22 mmol) are added, reaction mixture is purged again with argon for 5 minutes and stirred at 80° C. for 70 minutes in the microwave reactor. The reaction mixture is diluted with saturated sodium hydrogen carbonate solution, and extracted with ethyl acetate several times. The organic layer is washed with brine, dried over $MgSO_4$, filtered and concentrated in vacuo. The crude residue is purified by silica gel column chromatography (DCM:MeOH=99:1 to 9:1) to afford I-3.5.

Yield 81% m/z 645 [M+H]+, rt 1.11 min, LC-MS Method Z011_S03.

Step 6: Synthesis of Example 27

To I-3.5 (923.0 mg, 1.43 mmol) in acetonitrile (40 mL) is added p-toluenesulfonic acid monohydrate (681.0 mg, 3.58 mmol) and reaction mixture is stirred for 3 days at r.t. The reaction mixture is neutralized with TEA and concentrated in vacuo. Water was added and the reaction mixture is extracted with ethyl acetate several times. The organic layer is washed with brine, dried over $MgSO_4$, filtered and concentrated in vacuo. The crude residue is purified by reversed phase HPLC.

Yield 61%, m/z 545 [M+H]+, rt 1.02 min, LC-MS Method Z011_S03.

Method D

Alternative Synthesis of N-[(1S)-1-cyano-2-[2-fluoro-4-[1'-(oxetan-3-yl)spiro[1H-isobenzofuran-3,4'-piperidine]-5-yl]phenyl]ethyl]-3-azabicyclo[2.2.2]octane-4-carboxamide Example 27

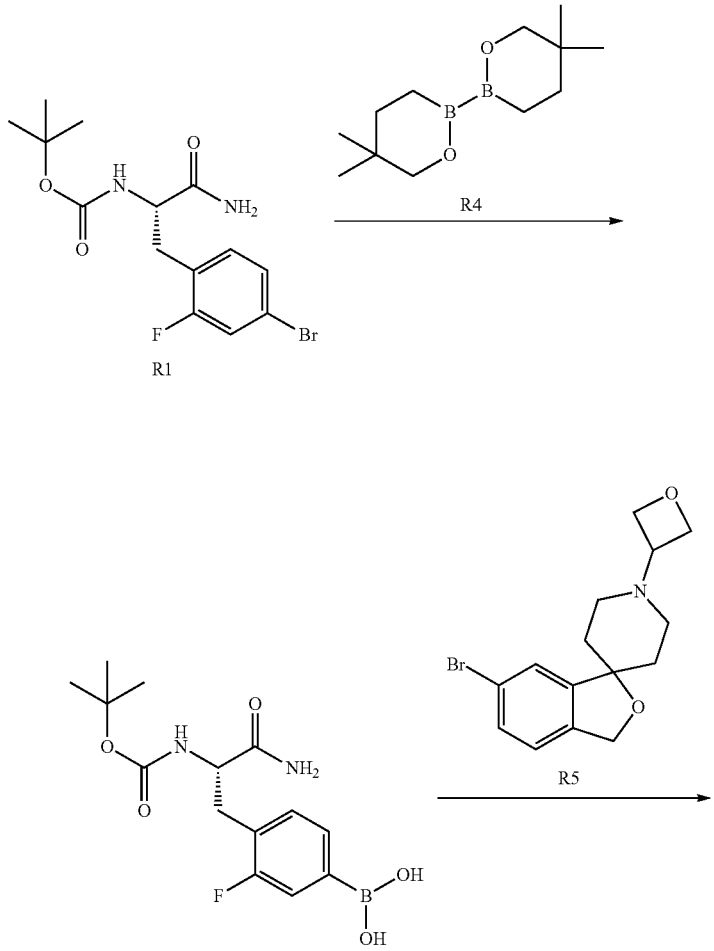

-continued

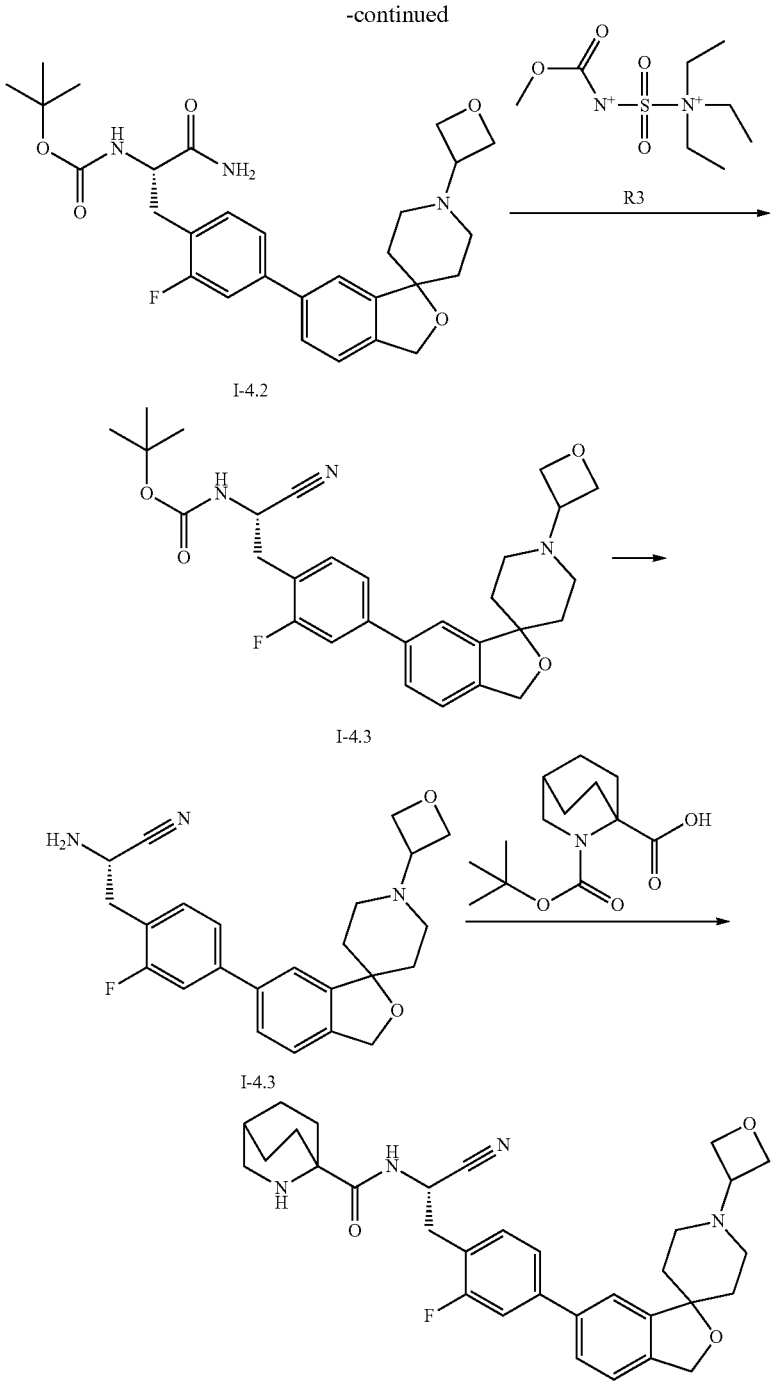

Example 27

Step 1: Synthesis of Intermediate I-4.1

To R1 (340 mg, 0.94 mmol) in dioxane (7 mL) R4 (288 mg, 1.28 mmol), potassium acetate (277 mg, 2.82 mmol) and [1,1'-bis(diphenylphosphino)ferrocene]dichloropalladium(II), complex with dichloromethane (1:1) (15.3 mg, 0.02 mmol) are added. The mixture is purged with nitrogen and heated to 70° C. for 2 h. The reaction mixture is diluted with saturated sodium hydrogen carbonate solution and extracted with ethyl acetate. The organic layer is washed with brine, dried over $MgSO_4$, filtered and concentrated in vacuo. The residue is purified by reversed phase HPLC to provide I-4.1.

Yield 90%, m/z 325 [M−H]−, rt 0.94 min, LC-MS Method Z020_S01.

Step 2: Synthesis of Intermediate I-4.2

To I-4.1 (228 mg, 0.70 mmol) in acetronitrile (10 mL) is added R5 (239 mg, 0.70 mmol) and mixture is purged with argon. Potassium carbonate aqueous solution 2 mol/L (700 μL, 1.4 mmol) and 1,1-bis(di-tert-butylphosphino)ferrocene palladium dichloride (46 mg, 0.07 mmol) are added, reaction mixture is purged again with argon and stirred at 80° C. for 45 minutes in the microwave reactor. The reaction mixture is diluted with saturated sodium hydrogen carbonate solution and extracted with ethyl acetate. The organic layer is washed with brine, dried over $MgSO_4$, filtered and concentrated in vacuo. The residue is purified by reversed phase HPLC to provide I-4.2.

Yield 80%, m/z 526 $[M+H]^+$, rt 0.83 min, LC-MS Method Z011_S03.

Step 3: Synthesis of Intermediate I-4.3

To I-4.2 (294 mg, 0.56 mmol) in dichloromethane (10 mL) is added R3 (333 mg, 1.4 mmol) and the reaction mixture is stirred for 40 minutes at r.t. DCM is removed in vacuo, obtained residue is partitioned between ethyl acetate and 10% aqueous solution of tartaric acid, phases are separated and aqueous phase is extracted with ethyl acetatete. The combined organic layer is washed with saturated sodium hydrogen carbonate solution, brine, dried over $MgSO_4$, filtered and concentrated in vacuo to provide I-4.3.

Yield 95%, m/z 508 $[M+H]^+$, rt 1.06 min, LC-MS Method Z011_S03.

Step 4: Synthesis of Intermediate I-4.4

To I-4.3 (320 mg, 0.63 mmol) in acetonitrile (8 mL) is added p-toluenesulfonic acid monohydrate (600 mg, 3.15 mmol) and reaction mixture is stirred overnight at r.t. The reaction mixture is diluted with saturated sodium hydrogen carbonate solution and extracted with ethyl acetate three times. The organic layer is washed with brine, dried over $MgSO_4$, filtered and concentrated in vacuo.

Yield 80%, m/z 408 [M+H]+, rt 0.90 min, LC-MS Method Z011_S03.

Step 5: Synthesis of Example 27

To I-4.4 (30 mg, 0.07 mmol) in DMF (1 mL) are added 3-tert-butoxycarbonyl-3-azabicyclo[2.2.2]octane-4-carboxylic acid, prepared according to Radchenko et al. J. Org. Chem. 2009, 5541-5544 (19 mg, 0.07 mmol), N-methylmorpholine (16 μL, 0.15 mmol) and PPA (43 μL, 50% in DMF) at r.t. The reaction mixture is stirred for 2.5 hours at r.t., diluted with saturated sodium hydrogen carbonate solution and extracted with ethyl acetate several times. The organic layer is washed with brine, dried over $MgSO_4$, filtered and concentrated in vacuo. The residue is purified by reversed phase HPLC to provide Example 27 (During the work up and/or purification deprotection of Boc group occurs). Yield 32%, m/z 545 [M+H]+, rt 1.02 min, LC-MS Method Z011_S03.

Synthesis of Starting Materials/Educts

Synthesis of tert-butyl N-[(1S)-2-amino-1-[(4-bromo-2-fluoro-phenyl)methyl]-2-oxo-ethyl]carbamate (R1)

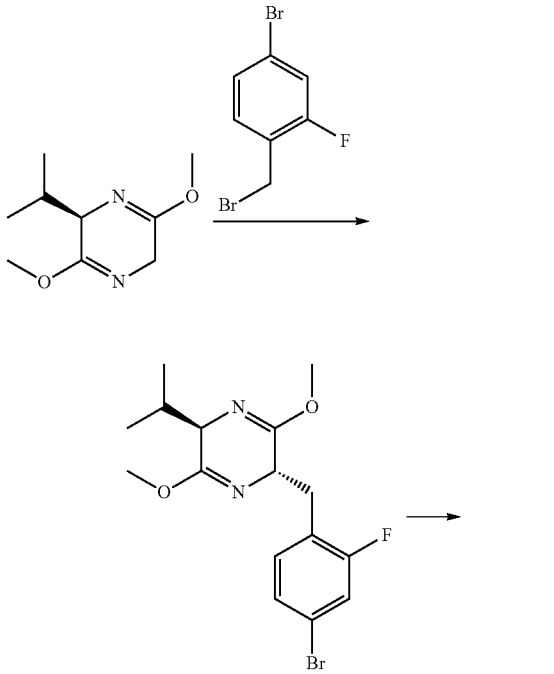

I-5.1

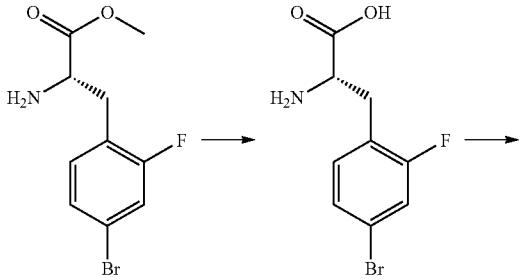

I-5.2 I-5.3

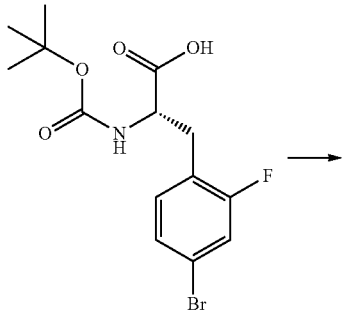

I-5.4

-continued

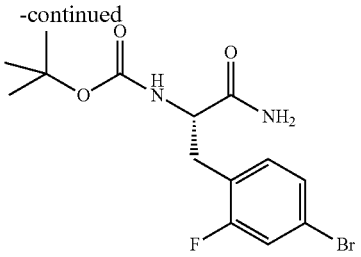

R1

Step 1: Synthesis of Intermediate I-5.1

(2R)-(−)-2,5-Dihydro-3,6-dimethoxy-2-isopropylpyrazine (212 g, 1151 mmol) in dry tetrahydrofuran (600 mL) is cooled to −78° C. Then n-butyllithium (2.5 M in hexanes, 552 mL, 1381 mmol) is added dropwise, keeping the temperature below −78° C. After 30 min 4-bromo-2-fluorobenzyl bromide (324 g, 1209 mmol) in dry tetrahydrofurane (120 mL) is added dropwise. The reaction mixture is stirred at −78° C. for 1 h. The mixture is quenched with saturated $NH_4Cl$ solution and extracted three times with ethyl acetate. The organic layer is washed with brine, dried over $Na_2SO_4$, filtered and evaporated in vacuo. The residue is purified by flash chromatography (heptane/ethyl acetate=80/20). Yield 60%.

Step 2: Synthesis of Intermediate I-5.2

To I-5.1 (104 g, 265 mmol) in acetonitrile (600 mL) aq. 0.2 M HCl (2788 mL, 558 mmol) is added. The mixture is stirred at RT for 12 h. The mixture is extracted with diethyl ether and the pH of the aqueous layer is adjusted to ~8 with saturated $NaHCO_3$ solution. Then it is extracted three times with ethyl acetate. The organic layer is washed with brine, dried over $Na_2SO_4$, filtered and concentrated. Yield 80%.

Step 3: Synthesis of Intermediate I-5.3

I-5.2 (62.4 g, 211 mmol) is stirred in aqueous 3 M HCl (3 mol/L, 1000 mL) at 60° C. for 16 h. The mixture is cooled down and the pH is adjusted to ~7 with aqueous 6 M NaOH. Then the reaction mixture is filtered, washed three times with water and dried in a vacuum oven at 40° C. for 12 h. Yield 74%.

Step 4: Synthesis of Intermediate I-5.4

To I-5.3 (151 g, 546 mmol) in 1,4-dioxane (2.2 L) is added aqueous 2 M sodium carbonate (301 mL, 602 mmol) and di-tertbutyl dicarbonate (138 g, 632 mmol). The mixture is stirred for 4 h. Then water is added and the pH is adjusted to ~4-5 with citric acid. The mixture is extracted three times with ethyl acetate. The organic layer is washed with brine, dried over $Na_2SO_4$, filtered and concentrated. The residue is stirred in heptane for 15 min and the product is filtered off. Yield 87%.

Step 5: Synthesis of R1

To I-5.4 (181 g, 476 mmol) in dry DMF (1200 mL) N-methylmorpholine (72 g, 713 mmol) and TBTU (153 g, 476 mmol) are added and the reaction mixture is stirred for 30 min. Then the reaction mixture is cooled to 0° C. and aqueous 35% ammonium chloride solution (47 mL, 856 mmol) is added and the mixture is stirred at room temperature for 12 h. Water is added and the formed product is filtered off and washed three times with water. The product is dried in a vacuum oven at 40° C. for 72 h. Yield 64%.

Synthesis of (1S,2S,4R)-3-[(tert.-butoxy)carbonyl]-3-azabicyclo[2.2.1]heptane-2-carboxylate (R2)

The compound is commercially available or can be synthesized in analogy to Tararov et al, Tetrahedron Asymmetry 13 (2002), 25-28.

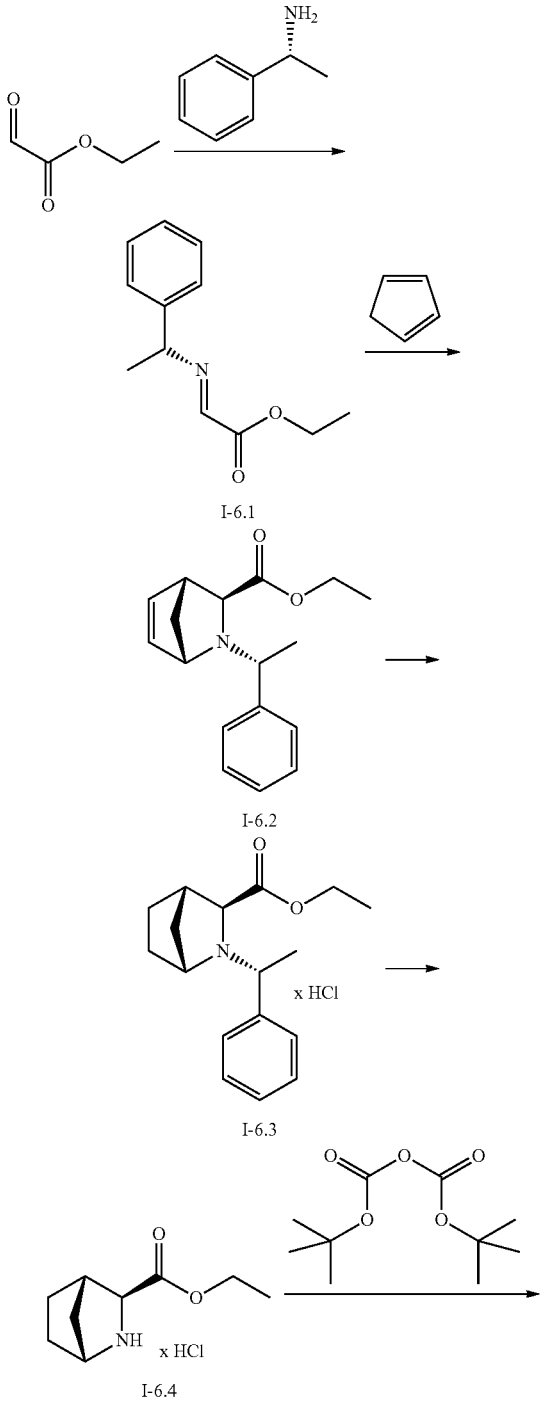

-continued

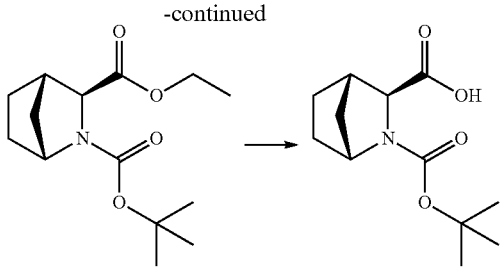

I-6.5 R2

Step 1: Synthesis of Intermediate I-6.1

A solution of ethyl oxoacetate (44.9 g, 0.44 mol), freshly distilled from a commercially available solution in toluene (at 50 mbar, 55° C.) in diethylether (300 ml) is cooled at −10° C., followed by dropwise addition of (R)-(+)-1-phenylethaneamine (53 g, 440 mmol), keeping the temperature below 0° C. After complete addition, $MgSO_4*H_2O$ (91 g, 660 mmol) is added, and the resulting mixture stirred at room temperature overnight. The mixture is filtered, the mother liquor concentrated in vacuo and the residue destilled under reduced pressure to yield I-6.1 (47 g, m/z 206 [M+H]+, rt 1.29 min, LC-MS Method V003_003). The product is used without further purification.

Step 2: Synthesis of Intermediate I-6.2

A solution of I-6.1 (47 g, 229 mmol) and 1,3-cyclopentadiene (30 g, 458 mmol) (freshly distilled from dicyclopentadiene) in DMF (150 ml) and 120 μl water is cooled to 0° C., before TFA (18 ml, 234 mmol) is added dropwise. The mixture is stirred overnight at room temperature, then added to a solution of 40 g $NaHCO_3$ in 1200 ml water and extracted with diethyl ether. The organic layer is separated, washed subsequently with aqueous $NaHCO_3$ and water, dried over $MgSO_4$, and concentrated in vacuo. The residue is purified by silica gel column chromatography (cyclohexane/ethyl acetate=9:1) to yield I-6.2 (Yield 52% m/z 272 [M+H]+, rt 0.42 min, LC-MS Method X001_004).

Step 3: Synthesis of Intermediate I-6.3

To a solution of I-6.2 (24.8 g, 91 mmol) in ethanol (250 ml), Raney-nickel is added (2.5 g) and reacted at 50 psi under a hydrogen atmosphere at room temperature. The catalyst is filtered off, the solution is concentrated in vacuo and the residue is purified by silica gel column chromatography (cyclohexane/ethyl acetate 9:1). After evaporation of the organic solvent, the obtained product is redissolved in diethyl ether and triturated with solution of HCl in dioxane, concentrated in vacuo, redissolved in 200 ml ethanol and concentrated in vacuo to yield I-6.3 (Yield 78% m/z 274 [M+H]+, rt 0.42 min, LC-MS Method X001_004).

Step 4: Synthesis of Intermediate I-6.4

To a solution of I-6.3 (22 g, 71 mmol) in ethanol (250 ml), 10% Pd/C is added (2.5 g) and reacted at 15 bar under a hydrogen atmosphere at room temperature. The catalyst is filtered off, the solution is concentrated in vacuo. The residue is washed with diisopropyl ether to yield I-6.4 (Yield 98% m/z 170 [M+H]+, rt 0.48 min, LC-MS Method V001_007).

Step 5: Synthesis of Intermediate I-6.5

To I-6.4 (14.3 g, 69.3 mmol) in a solution of triethylamin (24.6 ml, 175.3 mmol), THF (150 ml) and water (2 mL), di-tert-butyl dicarbonate (15.9 g, 73 mmol) is added and the resulting mixture is stirred for 40 hours at room temperature, then concentrated in vacuo. Ethyl acetate is added to the residue, subsequently extracted with water, 1N aqueous acetic acid and water, before the organic layer is dried over $MgSO_4$, filtered and concentrated in vacuo to yield I-6.5 (Yield 95% m/z 270 [M+H]+, rt 1.33 min, LC-MS Method V003_003).

Step 6: Synthesis of R2

A mixture of I-6.5 (16.9 g; 63 mmol) in acetone (152 ml), water (50 ml) and lithium hydroxide (3 g, 126 mmol) is stirred overnight at room temperature. Water (100 ml) is added, the volume reduced in vacuo before cooling to 0° C. followed by the addition of 1N aqueous HCl to acidify to a pH of 2-3, immediately followed by extraction with ethyl acetate. The organic layer is washed with water, dried ($MgSO_4$) and concentrated. To the residue, dichloromethane (100 ml) and cyclohexane (100 ml) are added, the volume reduced in vacuo by half and the mixture temperated at 15° C. The precipitate is filtered off, washed with cyclohexane to yield R2 (Yield 66%, m/z 242 [M+H]+).

Synthesis of 5-bromo-1'-(oxetan-3-yl)spiro[1H-isobenzofuran-3,4'-piperidine] (R5)

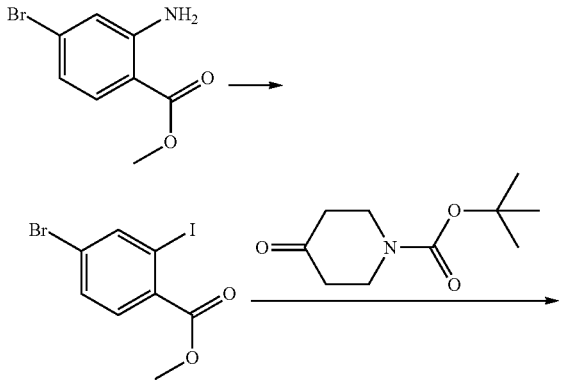

I-7.1

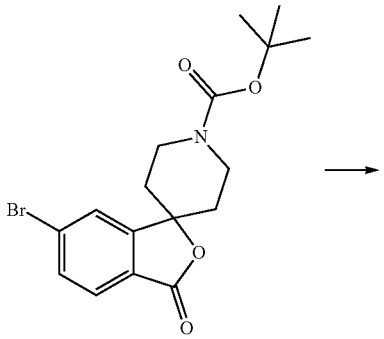

I-7.2

-continued

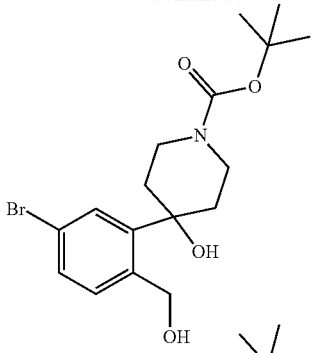

I-7.3

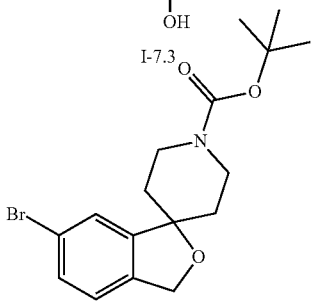

I-7.4

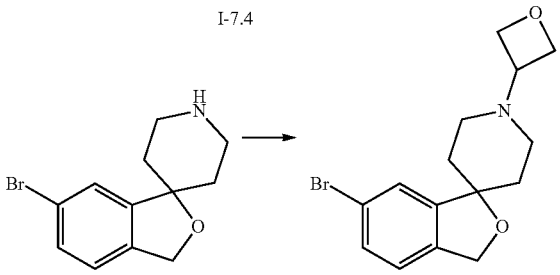

I-7.4 R5

Step 1: Synthesis of Intermediate I-7.1

Methyl 2-amino-4-brombenzoate (10 g, 43.47 mmol) is suspended in sulphuric acid 20% (200 mL) and obtained solution is cooled down to 0° C. Sodium nitrite (3.60 g, 52.16 mmol), dissolved in water (40 mL), is added dropwise between 0° C.-5° C. and the reaction mixture is stirred for further 40 minutes at this temperature. Afterwards a cooled solution (ca. 0° C.) of potassium iodide (14.43 g, 86.93 mmol) in water (40 mL) is added dropwise and the reaction mixture is stirred for 1 h at 5° C. The reaction mixture is poured onto ice-water and extracted with ethyl acetate. The organic layer is washed with water, 10% aq. sodium thiosulfate solution, brine, dried over $Na_2SO_4$ and concentrated in vacuo. Yield 94%.

Step 2: Synthesis of Intermediate I-7.2

I-7.1 (9.42 g, 27.63 mmol) and tert-butyl 4-oxopiperidine-1-carboxylate (6.24 g, 30.40 mmol) in dry THF (200 mL) is cooled down to −70° C. Isopropylmagnesium chloride-lithium chloride complex (1.3 mol/L in THF, 23.38 mL, 30.40 mmol) is added dropwise and reaction mixture is stirred for further 20 minutes at this temperature, is allowed to come to r.t. and stirred for 45 minutes. The reaction mixture is quenched with water and extracted with ethyl acetate. The organic layer is washed with brine, dried over $Na_2SO_4$ and concentrated in vacuo. The crude residue is purified by flash column chromatography (petroleum ether: EtOAc=95:5 to 40:60) to provide I-7.2.

Yield 74%, m/z 326,328 [M+H−tert-Bu]+, rt 1.09 min, LC-MS Method Z011_S03.

The following intermediates as shown in Table 2 are synthesized in a similar fashion from the appropriate intermediates:

TABLE 2

| Intermediate | Structure | m/z $[M + H]^+$ | rt (min) | LC-MS method |
|---|---|---|---|---|
| I-7.2.1 | 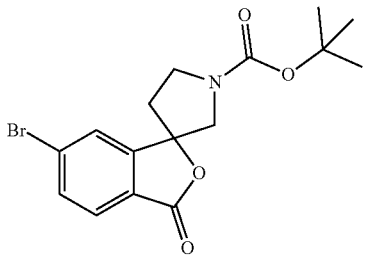 | 312; 314 [M-tert-But + H]+ | 1.06 | Z011_S03 |
| I-7.2.2 | 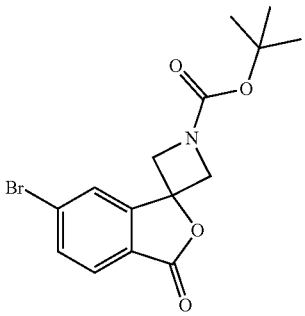 | 298; 300 [M-tert-But + H]+ | 1.07 | Z012_504 |

Alternative Synthesis of Intermediate I-7.1

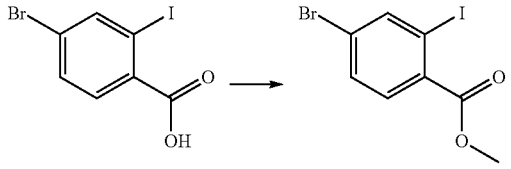

I-7.1

To 4-bromo-2-iodobenzoic acid (9.0 g, 27.53 mmol) in methanol (50 mL) is added concentrated sulphuric acid (10 mL) and the reaction mixture is stirred for 90 minutes at 80° C. The reaction mixture is poured onto ice water, sodium hydrogen carbonate is added until a pH value of 7 is reached and the reaction mixture is extracted with ethyl acetate. The organic layer is washed with brine, dried over $MgSO_4$, filtered and concentrated in vacuo. Yield 95%.

Step 3: Synthesis of Intermediate I-7.3

To I-7.2 (8.11 g, 21.22 mmol) in THF (100 mL) is added lithium borohydride (2 mol/L in THF, 21.22 mL, 42.44 mmol) and the reaction mixture is stirred overnight at r.t. HPLC-MS analysis indicated 20% conversion. Additional lithium borohydride (2 mol/L in THF, 27.0 mL, 54.0 mmol) is added dropwise and the reaction mixture is stirred for 6 days at r.t. The reaction mixture is carefully quenched with water while cooling to ca. 0° C. with an ice bath. Saturated sodium hydrogen carbonate solution is added to the reaction mixture, obtained precipitate is filtered off, and mother liquor is extracted with ethyl acetate several times. The organic layer is washed with brine, dried over $MgSO_4$, filtered and concentrated in vacuo.

Yield >95%, m/z 312/314 [M+H−tert-Butyl−$H_2O$]+, rt 1.01 min, LC-MS Method Z011_S03.

Step 4: Synthesis of Intermediate I-7.4

I-7.3 (605 mg, 1.57 mmol) is dissolved in dry THF (20 mL) and cooled down to 0° C., TEA (1.09 mL, 7.83 mmol) and p-toluenesulfonic anhydride (613.44 mg, 1.88 mmol) are added. The reaction mixture is allowed to come to r.t. and stirred overnight. The reaction mixture is diluted with water and saturated sodium hydrogen carbonate solution and extracted with ethyl acetate several times. The organic layer is washed with brine, dried over $Na_2SO_4$, filtered and concentrated in vacuo. The residue is purified by reversed phase HPLC.

Yield 72%, m/z 368; 370 [M+H]+

Step 5: Synthesis of Intermediate I-7.5

I-7.4 (240 mg, 1.57 mmol) is dissolved in dry DCM (2 mL) and TFA (500 μL, 6.53 mmol) is added. The reaction mixture is allowed for 70 minutes at r.t. The reaction mixture is concentrated in vacuo, the residue is redissolved in methanol, filtered through solid phase cartridge (Strato-Spheres™ PL-HCO3 MP Resin) and methanol is removed in vacuo.

Yield 97%, m/z 268; 270 [M+H]+, rt 0.93 min, LC-MS Method Z011_S03.

Alternative Synthesis of Intermediate I-7.5

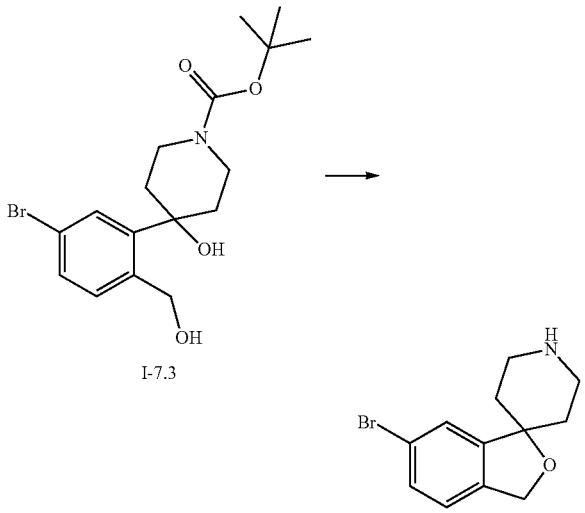

I-7.3

I-7.5

I-7.3 (8.39 g, 21.71 mmol) is dissolved in dry THF (25 mL), 5N aqueous HCl (25 mL) is added and the reaction mixture is stirred at 90° C. for 30 h. Reaction mixture is cooled to r.t., basicified with saturated sodium hydrogen carbonate solution and extracted with ethyl acetate several times. The organic layer is washed with brine, dried over $Na_2SO_4$, filtered and concentrated in vacuo.

Yield 76%, m/z 268; 270 [M+H]+, rt 0.93 min, LC-MS Method Z011_S03.

Step 6: Synthesis of R5

I-7.5 (5.0 g, 18.49 mmol) is dissolved in dry tetrahydrofurane (20 mL), 3-oxetanone (1.78 mL, 27.73 mmol) and acetic acid (1.06 mL, 18.49 mmol) are added and the reaction mixture is stirred for 25 minutes at r.t. Sodium triacetoxyborohydride (6.82 g, 30.57 mmol) is added and the reaction mixture is stirred for further 30 minutes at r.t. The reaction mixture is quenched with MeOH, diluted with saturated sodium hydrogen carbonate solution and extracted with ethyl acetate several times. The organic layer is washed with brine, dried over $MgSO_4$ and concentrated in vacuo to provide R5.

Yield 89%, m/z 324, 326 [M+H]+, rt 0.93 min, LC-MS Method Z011_S03.

Synthesis of 6-bromo-1'-methyl-spiro[indane-1,4'-piperidine] (R7)

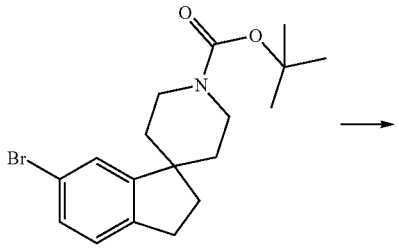

R6

-continued

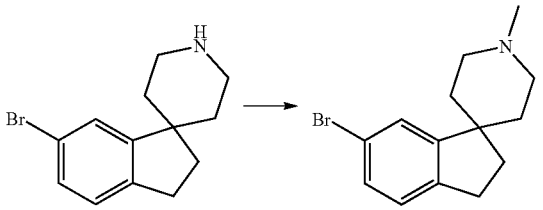

I-8.1 R7

Step 1: Synthesis of Intermediate I-8.1

To R6, purchased from WUXI APPTEC (200 mg, 0.55 mmol) in dichloromethane (3 mL) is added trifluoroacetic acid (0.25 mL) and reaction mixture is stirred overnight at r.t. The reaction mixture is concentrated in vacuo, the residue is redissolved in methanol, filtered through solid phase cartridge (StratoSpheres™ PL-HCO3 MP Resin) and methanol is removed in vacuo. Yield >95%.

Step 2: Synthesis of R7

To I-8.1 (152 mg, 0.57 mmol) in methanol (4 mL) are added formaldehyde (37% in water, 0.21 mL, 2.86 mmol) and acetic acid (0.05 mL, 0.86 mmol). The reaction mixture is stirred 2 h at r.t. Sodium triacetoxyborohydride (302.6 mg, 1.43 mmol) is added and the reaction mixture is stirred 80 minutes at r.t. The reaction mixture is concentrated, triturated with water and saturated sodium hydrogen carbonate solution and extracted with ethyl acetate. The organic layer is washed with saturated sodium hydrogen carbonate solution and brine. The precipitate is filtered off and the filtrate is dried over $Na_2SO_4$, filtered and concentrated in vacuo to yield R7.

Yield 89%.

Synthesis of 5-bromo-1,1'-dimethyl-spiro[indoline-3,4'-piperidine]-2-one (R10)

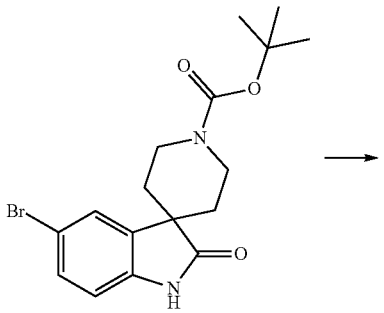

R8

-continued

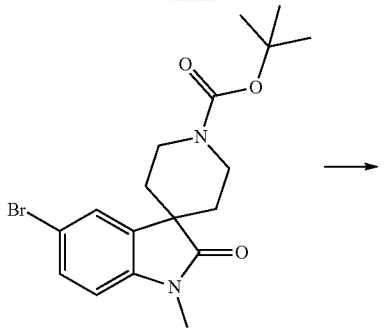

R9

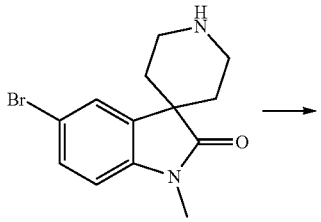

I-9.1

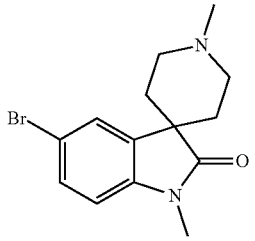

R10

Step 1: Synthesis of R9

To R8, purchased from ACTIVATE (200 mg, 0.53 mmol) in DMF (4 mL) is added sodium hydride (60% dispersion in mineral oil, 31.5 mg, 0.79 mmol) under cooling to 0° C. and reaction mixture is stirred for further 30 minutes at r.t. Methyl iodide (36 μL, 0.58 mmol) is added and the reaction mixture is stirred for 40 minutes at r.t. The reaction mixture is diluted with water and extracted with ethyl acetate. The organic layer is washed with water and brine, dried over $Na_2SO_4$, filtered and concentrated in vacuo to provide R9. Yield 98%.

Step 2: Synthesis of Intermediate I-9.1

To R9 (191 mg, 0.48 mmol) in dichloromethane (5 mL) is added trifluoroacetic acid (0.5 mL) and reaction mixture is stirred for 20 minutes at r.t. The reaction mixture is concentrated in vacuo, the residue is redissolved in methanol, filtered through solid phase cartridge (StratoSpheres™ PL-HCO3 MP Resin) and methanol is removed in vacuo. Yield >95%

The following intermediates as shown in Table 3 are synthesized in a similar fashion from the appropriate intermediates:

TABLE 3

| Intermediate | Structure | m/z [M + H]+ | rt (min) | LC-MS method |
|---|---|---|---|---|
| I-9.1.1 | 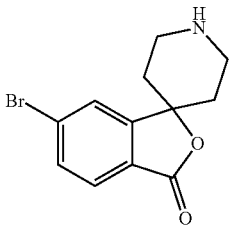 | 282; 284 | 0.69 | Z012_S04 |
| I-9.1.2 | 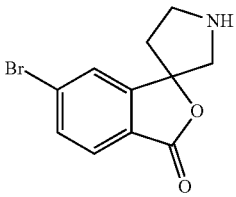 | 268; 270 | 0.57 | Z021_S01 |
| I-9.1.3 | 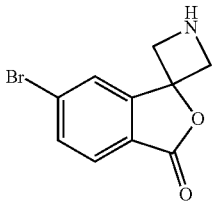 | 254; 256 | 0.62 | Z012_S04 |

Step 3: Synthesis of R10

To I-9.1 (152 mg, 0.52 mmol) in methanol (5 mL) are added formaldehyde (37% in water, 0.19 mL, 2.58 mmol) and acetic acid (0.044 mL, 0.77 mmol). The reaction mixture is stirred for 2 hours at r.t. Sodium triacetoxyborohydride (273.0 mg, 1.29 mmol) is added and the reaction mixture is stirred for 40 minutes at r.t. The reaction mixture is concentrated, diluted with water and saturated sodium hydrogen carbonate solution and extracted with ethyl acetate. The organic layer is washed with brine, dried over $Na_2SO_4$, filtered and concentrated in vacuo.

Yield >95%, 309; 311 [M+H]+, rt 0.75 min, LC-MS Method Z012_S04.

The following intermediates as shown in Table 4 are synthesized in a similar fashion from the appropriate intermediates:

TABLE 4

| Intermediate | Structure | m/z [M + H]+ | rt (min) | LC-MS method |
|---|---|---|---|---|
| R10.1 | 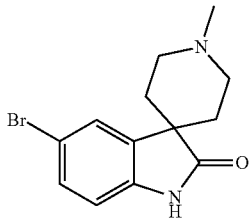 | 295; 297 | 0.69 | Z012_S04 |
| R10.2 | 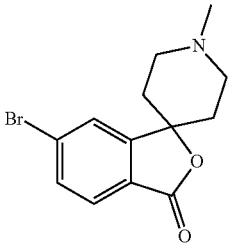 | 296; 298 | 0.70 | Z012_S04 |

TABLE 4-continued
| Intermediate | Structure | m/z [M + H]$^+$ | rt (min) | LC-MS method |
|---|---|---|---|---|
| R10.3 | 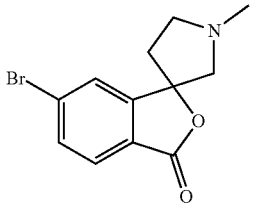 | 282; 284 | 0.68 | Z012_S04 |
| R10.4 | 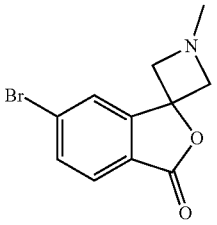 | 268; 270 | 0.62 | Z012_S04 |
| R10.5 | 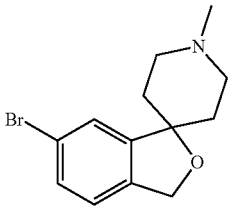 | 282; 284 | 0.77 | Z012_S04 |
| R10.6 | 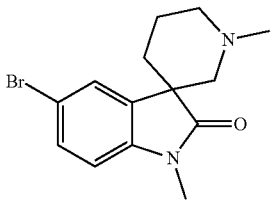 | 309; 311 | 0.59 | Z020_S01 |
| R10.7 | 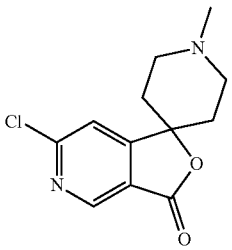 | 253 | 0.24 | Z021_S01 |

Synthesis of TFA salt of 5-bromospiro[indoline-3,4'-piperidine]-2-one (R11)

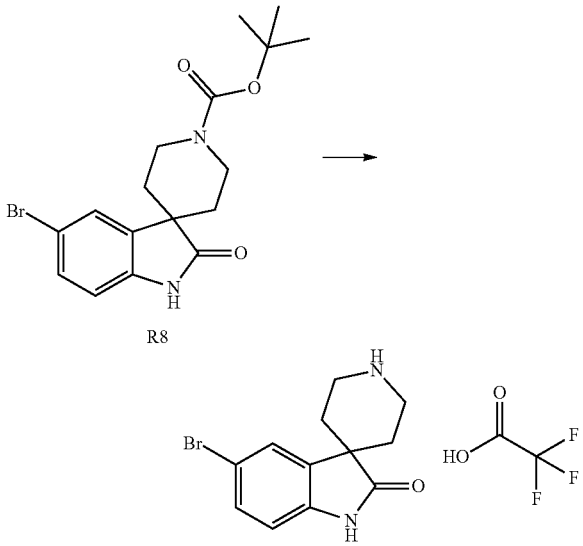

To R8, purchased from ACTIVATE (150 mg, 0.39 mmol) in dichloromethane (3 mL) is added trifluoroacetic acid (0.5 mL) and reaction mixture is stirred for 45 minutes at r.t. The reaction mixture is concentrated. Yield 100%.

Synthesis of tert-butyl 5-bromo-2-oxo-spiro[indoline-3,3'-pyrrolidine]-1'-carboxylate (R12)

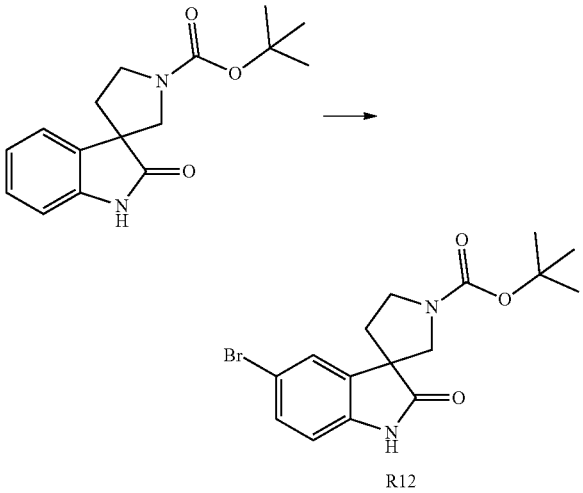

To tert-butyl 2-oxospiro[indoline-3,3'-pyrrolidine]-1'-carboxylate, purchased from Zerenex (50.0 mg, 0.17 mmol) in acetonitrile (1.5 mL) is added N-bromosuccinimide (30.5 mg, 0.17 mmol) and the reaction mixture is stirred for 5 h at r.t. The reaction mixture is diluted with water and saturated sodium hydrogen carbonate solution and extracted with ethyl acetate. The organic layer is washed with brine, dried and concentrated in vacuo. Yield 80%, m/z 367; 369 [M+H]+

Synthesis of 5-bromo-1-methyl-spiro[indoline-3,3'-piperidine]-2-one (R13)

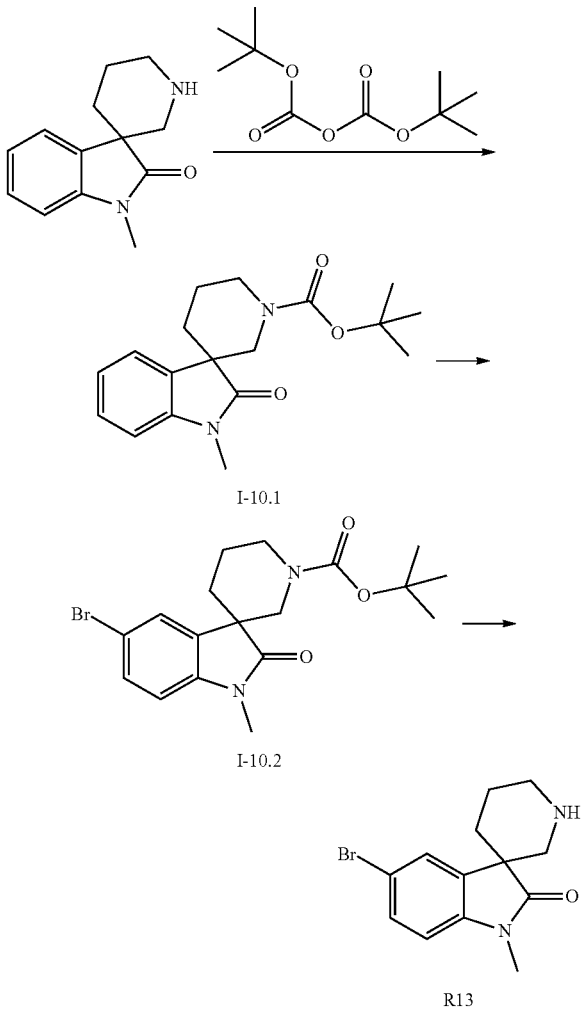

Step 1: Synthesis of Intermediate I-10.1

To 1-methylspiro[indole-3,3'-piperidine]-2(1H)-one, purchased from ChemBridge Corporation (1.0 g, 4.62 mmol) in dichloromethane (20 mL) are added TEA (0.64 mL, 4.62 mmol) and di-tert-butyl dicarbonate (958.6 mg, 4.39 mmol). The reaction mixture is stirred for 10 minutes at r.t., diluted with water and saturated sodium hydrogen carbonate solution and extracted with dichloromethane. The phases are separated and aqueous layer is extracted with DCM. The combined organic layers are dried over $MgSO_4$ and concentrated in vacuo.

Yield >95%, m/z 261 [M+H+tert-Butyl]+, rt 1.06 min, LC-MS Method Z020_S01.

Step 2: Synthesis of Intermediate I-10.2

To I-10.1 (1.54 g, 4.87 mmol) in acetonitrile (35 mL) is added N-bromosuccinimide (856.7 mg, 5 mmol) and the reaction mixture is stirred overnight at r.t. The reaction mixture is diluted with water and saturated sodium hydrogen carbonate solution and extracted with ethyl acetate. The organic layer is washed with saturated sodium hydrogen carbonate solution and brine, dried over $Na_2SO_4$, filtered and concentrated in vacuo.

Yield 93%, m/z 340 [M+H-tert-Butyl]+, rt 1.13 min, LC-MS Method Z020_S01.

Step 3: Synthesis of R13

To I-10.2 (200 mg, 0.51 mmol) in dichloromethane (10 mL) is added trifluoroacetic acid (5 mL) and the reaction mixture is stirred for 15 minutes at r.t. The reaction mixture is concentrated in vacuo and lyophilized. The residue is dissolved in dichloromethane and extracted with 1 mol/L aqueous sodium hydroxide and brine. The organic layer is dried and concentrated in vacuo.

Yield 88%, m/z 295; 297 [M+H]+, rt 0.59 min, LC-MS Method Z020_S01.

Synthesis of tert-butyl 6-chloro-3-oxo-spiro[furo[3,4-c]pyridine-1,4'-piperidine]-1'-carboxylate (R14)

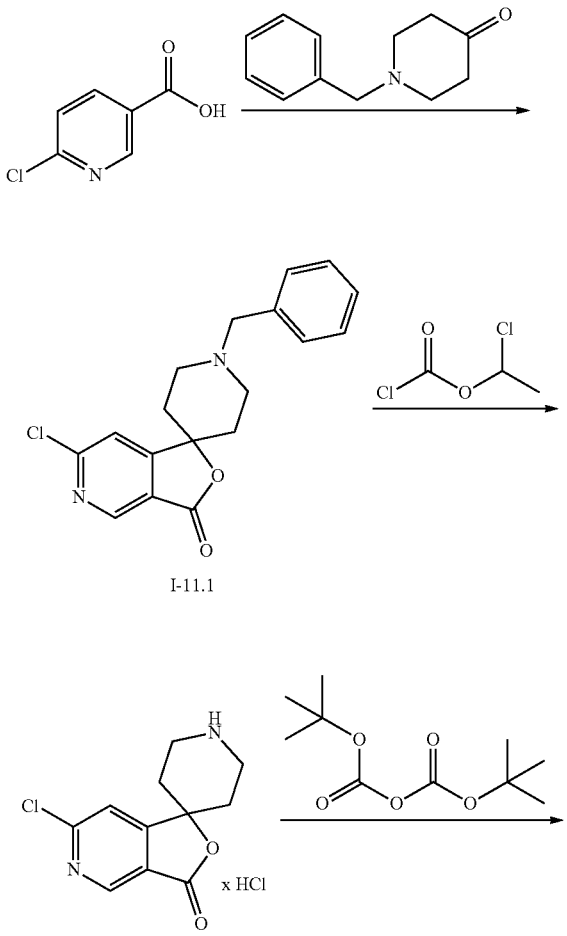

I-11.1

I-11.2

-continued

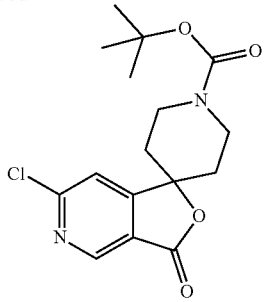

R14

Step 1: Synthesis of Intermediate I-11.1

The synthesis of the intermediate I-11.1 is described in EP2072519 A1, p. 36. At −78° C., a hexane solution (94 mL, 150.81 mmol) of 1.6 M n-butyllithium is added dropwise to a THF solution (110 mL) of 2,2,6,6-tetramethylpiperidine (16.14 g, 113.10 mmol) and obtained solution is stirred for 1 hour. Afterwards a THF solution (50 mL) of 6-chloronicotinic acid (6.0 g, 37.70 mmol) is added dropwise over 1 hour and the reaction mixture is stirred for 2 hours. A THF solution (50 mL) of 1-benzyl-4-piperidone (21.6 g, 113.10 mmol) is added dropwise at −78° C. After stirred for 2 hours, water (70 mL) is added, and the reaction mixture is warmed to room temperature.

The aqueous layer is separated, and the organic layer is extracted with aqueous 1 N sodium hydroxide solution (2×75 mL). The obtained aqueous layer is extracted with diethyl ether (100 mL), and the aqueous layer is acidified (pH-1) by adding concentrated hydrochloric acid.

After stirring for 1 hour, the precipitate is filtered off, washed with water, and dissolved in ethyl acetate.

The organic layer is washed with aqueous saturated sodium hydrogen carbonate solution, dried over $Na_2SO_4$ and concentrated in vacuo. The residue is washed with diethyl ether. Yield 66%, m/z 329 [M+H]+, rt 0.72 min, LC-MS Method Z012_S04.

The following intermediate as shown in Table 5 is synthesized in a similar fashion from the appropriate intermediate:

TABLE 5

| Intermediate | Structure | m/z [M + H]+ | rt (min) | LC-MS method |
|---|---|---|---|---|
| I-11.1.1 | 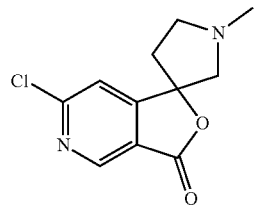 | 239 | 0.75 | Z011_S03 |

Step 2: Synthesis of Intermediate I-11.2

I-11.1 (2.0 g, 6.08 mmol) in dichloroethane (15 mL) is cooled down to 0° C. A solution of 1-chloroethyl chloroformate (1.98 mL, 18.25 mmol) in dichloroethane (5 mL) is added slowly and the reaction mixture is stirred for further 15 minutes at 0° C. Afterwards the reaction mixture is heated to reflux and stirred overnight. The reaction mixture is concentrated in vacuo. The residue is dissolved in methanol and heated to reflux for 30 minutes, during this time precipitate is formed. The reaction mixture is diluted with dichloromethane and the precipitate is filtered off to provide I-11.2 (hydrochloride). Yield 61%.

Step 3: Synthesis of R14

To I-11.2 (500 mg, 1.82 mmol) in dichloromethane (10 mL) are added TEA (0.51 mL, 3.64 mmol) and di-tert-butyl dicarbonate (396.6 mg, 1.82 mmol). The reaction mixture is stirred for 20 minutes at r.t., diluted with water and saturated sodium hydrogen carbonate solution and extracted with dichloromethane. The organic layer is dried and concentrated in vacuo. Yield 91%.

Synthesis of 3-chloro-1'-methyl-spiro[furo[3,4-b]pyridine-5,4'-piperidine]-7-one (R15)

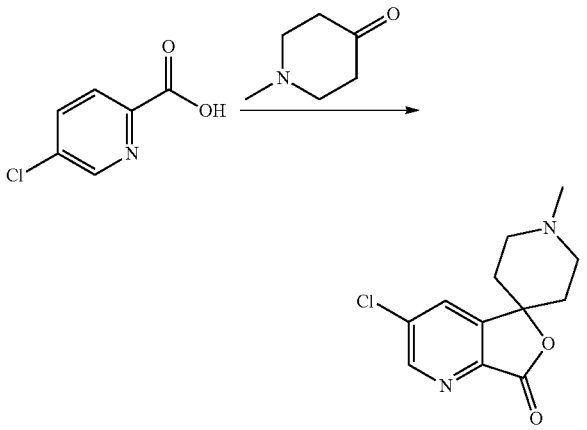

R15

At −78° C., a hexane solution (2.38 mL, 3.81 mmol) of 1.6 M n-butyllithium is added dropwise to a THF solution (5 mL) of 2,2,6,6-tetramethylpiperidine (0.76 mL, 4.43 mmol) and obtained solution is stirred for 1 hour at this temperature. Afterwards a THF solution (1 mL) of 5-chloro-2-pyridinecarboxylic acid (0.2 g, 1.27 mmol) is added dropwise over 5 minutes and reaction mixture is stirred for 45 minutes. A THF solution (1 mL) of 1-methyl-4-piperidone (0.44 mL, 3.81 mmol) is added dropwise at −78° C. After 1 hour, water (10 mL) is added, and reaction mixture is warmed to room temperature.

Ethyl acetate (15 mL) and aqueous saturated $NaHCO_3$ solution (15 mL) are added to the reaction mixture and the aqueous layer is separated. The organic layer is extracted with aqueous saturated $NaHCO_3$ solution (2×10 mL). The combined aqueous phase is acidified (pH~1) by adding concentrated hydrochloric acid.

After stirring for 1 hour reaction mixture is basified by adding aqueous saturated $NaHCO_3$ solution and extracted with ethyl acetate (4×25 mL). The organic layer is washed with brine, dried over $Na_2SO_4$ and concentrated in vacuo to provide R15. Yield 21%, m/z 253, 255 [M+H]+, rt 0.41 min, LC-MS Method Z012_S04.

Synthesis of 6-chloro-1'-(oxetan-3-yl)spiro[furo[3,4-c]pyridine-1,4'-piperidine]-3-one (R16)

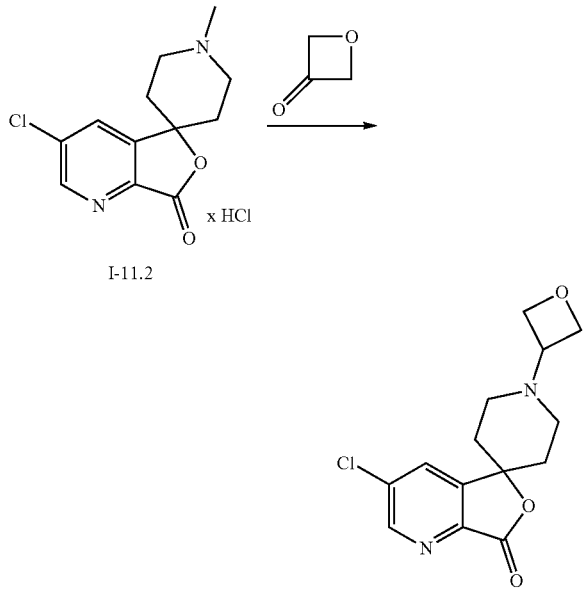

I-11.2

R16 a) Generation of Free Base:

I-11.2 (200 mg, 0.73 mmol) was partly dissolved in dried methanol, polymer-bound tetraalkyl-ammonium carbonate (Aldrich, 540293) is added and this mixture is stirred for 2 hours at r.t. Polymer-bound tetraalkyl-ammonium carbonate is filtered off and methanol is removed in vacuo to deliver free base of I-11.2.

b) Free base of I-11.2 is dissolved in the dry dichloromethane (3 mL)/dry tetrahydrofurane (1 mL) mixture, 3-oxetanone (0.23 mL, 3.64 mmol) and acetic acid (0.06 mL, 1.1 mmol) are added. The reaction mixture is stirred for 75 minutes at r.t., then sodium triacetoxyborohydride is added and the reaction mixture stirred for 15 minutes at r.t. The reaction mixture is diluted with saturated sodium hydrogen carbonate solution and extracted with ethyl acetate. The organic layer is washed with brine, dried over $Na_2SO_4$ and concentrated in vacuo. Yield 80%, m/z 295 [M+H]+, rt 0.75 min, LC-MS Method Z011_S03.

Synthesis of 6-chloro-1'-(oxetan-3-yl)spiro[3H-furo[3,4-c]pyridine-1,4'-piperidine] (R17)

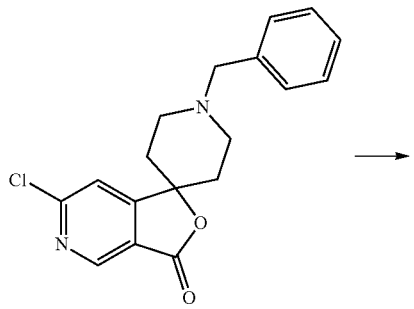

I-11.1

-continued

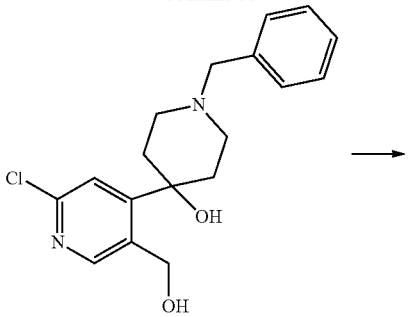

I-11.3

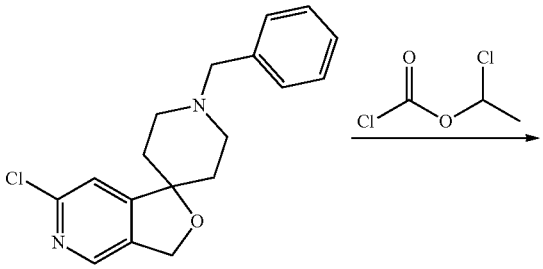

I-11.4

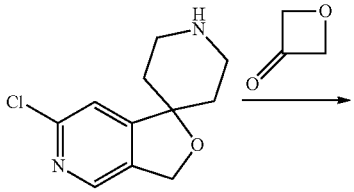

I-11.5

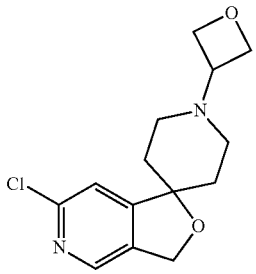

R17

Step 1: Synthesis of Intermediate I-11.3

To I-11.1 (1.00 g, 3.04 mmol) in methanol (15 mL) is added sodium borohydride (345 mg, 9.12 mmol) in small portions and the reaction mixture is stirred for 20 h at r.t. Additional sodium borohydride (750 mg, 19.82 mmol) is added in 3 portions (each 250 mg) over 5 h to the reaction mixture. The reaction mixture is quenched with water and diluted with ethyl acetate. The organic layer is separated and aqueous layer is extracted with ethyl acetate. Combined organic layer is washed with saturated sodium hydrogen carbonate solution, brine, dried over $Na_2SO_4$ and concentrated in vacuo. The residue is purified by reversed phase HPLC to provide I-11.3. Yield 40%, m/z 333 [M+H]+, rt 0.91 min, LC-MS Method Z011_S03.

Step 2: Synthesis of Intermediate I-11.4

To I-11.3 (378 mg, 1.14 mmol) in dry THF (5 mL) are added TEA (0.95 mL, 6.81 mmol) and methanesulfonyl chloride (0.26 mL, 3.5 mmol) at 0° C. The reaction mixture is allowed to come to r.t. and stirred for 1 h. The reaction mixture is diluted with saturated sodium hydrogen carbonate solution and extracted with ethyl acetate. The organic layer is washed with brine, dried over $Na_2SO_4$ and concentrated in vacuo to provide crude product which is used in the next step without further purification.

Yield 95%, m/z 315 [M+H]+, rt 1.06 min, LC-MS Method Z011_S03.

Step 3: Synthesis of Intermediate I-11.5

To a solution of I-11.4 (246 mg, 0.78 mmol) in dichloroethane (4 mL) is added 1-chloroethyl chloroformate (0.42 mL, 3.91 mmol) and the reaction mixture is heated to reflux and stirred for 3 hours. Dichloroethane was removed in vacuo, obtained residue is redissolved in methanol (3 mL) and obtained solution is refluxed for 30 min. Reaction mixture is cooled to r.t. and purified by reversed phase HPLC to provide I-11.5. Yield 72%, m/z 225 [M+H]+, rt 0.71 min, LC-MS Method Z011_S03.

Step 4: Synthesis of R17

I-11.5 (114 mg, 0.51 mmol) is dissolved in dry tetrahydrofurane (2 mL), 3-oxetanone (0.05 mL, 0.76 mmol) and acetic acid (0.044 mL, 0.76 mmol) are added and the reaction mixture is stirred for 1 hour at r.t. Sodium triacetoxyborohydride (269 mg, 1.27 mmol) is added and the reaction mixture is stirred for further 15 min at r.t. The reaction mixture is diluted with saturated sodium hydrogen carbonate solution and extracted with ethyl acetate. The organic layer is washed with brine, dried over $MgSO_4$ and concentrated in vacuo to provide R17. Yield 62%, m/z 281 [M+H]+, rt 0.76 min, LC-MS Method Z011_S03.

Synthesis of 2-chloro-1'-(oxetan-3-yl)spiro[furo[3,4-b]pyridine-7,4'-piperidine]-5-one (R18)

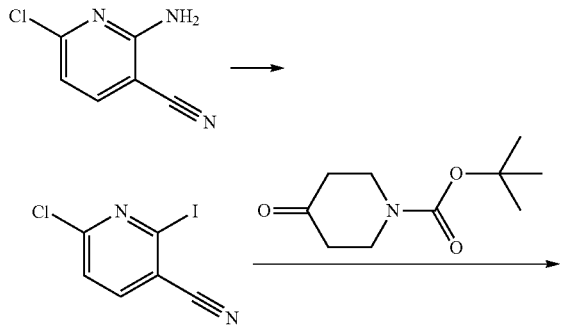

I-12.1

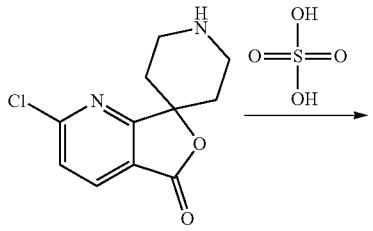

I-12.2

-continued

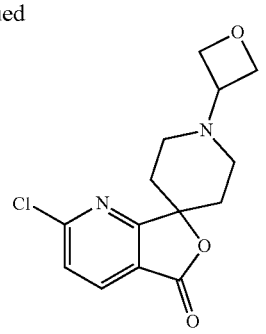

R18

Step 1: Synthesis of Intermediate I-12.1

2-Amino-6-chlorinonicotinonitrile, purchased from ABLOCK PHARMATECH (2.0 g, 13.02 mmol) is dissolved in dry tetrahydrofurane (40 mL), copper (I) iodide (3.72 g, 19.54 mmol), diiodomethane (8.39 mL, 104.2 mmol) and tert-butyl nitrite (6.20 mL, 52.1 mmol) are added. Reaction mixture is refluxed for 1.5 h, cooled to RT and all volatiles are removed in vacuo. Obtained residue is dissolved in ethyl acetate (100 mL) and washed with 10% aqueous sodium thiosulfate solution (25 mL), saturated sodium hydrogen carbonate solution (25 mL), dried over $MgSO_4$, filtered and concentrated in vacuo. The crude residue is purified by flash column chromatography to provide I-12.1 (eluent: petroleum ether/ethyl acetate).

Yield 74%, m/z 265 [M+H]+, rt 0.90 min, LC-MS Method Z012_S04.

Step 2: Synthesis of Intermediate I-12.2

I-12.1 (1.0 g, 3.78 mmol) and tert-butyl 4-oxopiperidine-1-carboxylate (753 mg, 3.78 mmol) are dissolved in dry THF (10 mL) and the reaction mixture is cooled down to −65° C. Isopropylmagnesium chloride-lithium chloride complex (1.3 mol/L in THF, 3.78 mL, 4.92 mmol) is added dropwise and the reaction mixture is stirred for further 10 min at this temperature. Afterwards the reaction mixture is allowed to reach r.t., stirred for 20 minutes and methanol (0.8 mL, 19.7 mmol) is added. The reaction mixture is cooled to 0° C. and 50% aqueous sulphuric acid solution (2.0 mL) is added dropwise. The reaction mixture is warmed to r.t. and stirred overnight. White precipitate formed is filtered off, washed with THF and dried in vacuum to provide crude I-12.2 (sulfate salt) as a white solid. Crude product was used in the next step without further purification.

Yield 94%, m/z 239 [M+H]+, rt 0.69 min, LC-MS Method Z011_S03.

Step 3: Synthesis of R18 a) Generation of Free Base:

I-12.2 (150 mg, 0.45 mmol) was dissolved in methanol (2 mL)/water (2 mL) mixture, polymer-bound tetraalkylammonium carbonate (Aldrich, 540293) is added and this mixture is stirred for 1 hour at r.t. Polymer-bound tetraalkylammonium carbonate is filtered off, methanol and water are removed in vacuo to deliver free base of I-12.2.

b) Obtained residue is redissolved in THF (2 mL)/water (0.1 mL) mixture, 3-oxetanone (0.04 mL, 0.67 mmol) and acetic acid (0.038 mL, 0.67 mmol) are added and the reaction mixture is stirred for 1 hour at r.t. Sodium triacetoxyborohydride is added and the reaction mixture is stirred overnight at r.t. The reaction mixture is diluted with saturated sodium hydrogen carbonate solution and extracted with ethyl acetate. The organic layer is washed with brine, dried over $MgSO_4$ and concentrated in vacuo. The crude residue is purified by flash column chromatography to provide R18 (eluent: DCM/MeOH).

Yield 18%, m/z 295 [M+H]+, rt 0.74 min, LC-MS Method Z011_S03.

Synthesis of 2-chloro-1'-(oxetan-3-yl)spiro[5H-furo[3,4-b]pyridine-7,4'-piperidine] (R19)

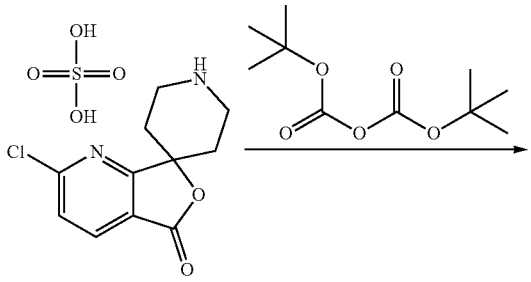

I-12.2

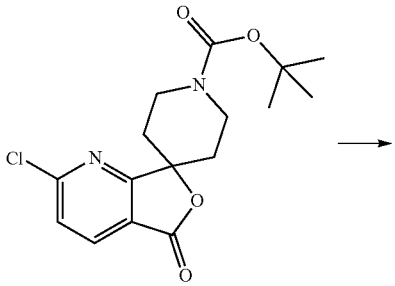

I-12.3

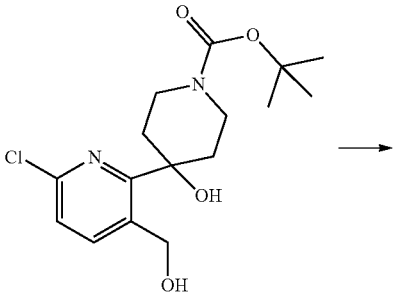

I-12.4

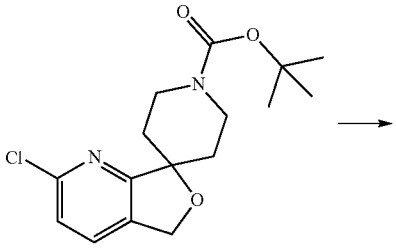

I-12.5

-continued

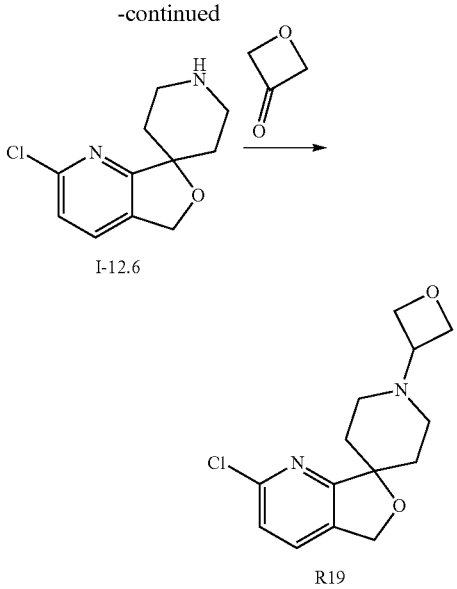

I-12.6

R19

Step 1: Synthesis of Intermediate I-12.3

To I-12.2 (3.25 g, 9.65 mmol) in dichloromethane (50 mL) is added TEA (4.04 mL, 28.95 mmol), the reaction mixture is stirred for 20 minutes at r.t., and di-tert-butyl dicarbonate (2.11 g, 9.65 mmol) is added. The reaction mixture is stirred for 90 minutes at r.t., diluted with saturated sodium hydrogen carbonate solution and extracted with ethyl acetate several times. The organic layer is washed with brine, dried over $MgSO_4$, concentrated in vacuo and obtained residue is purified by flash column chromatography (petroleum ether:EtOAc=95:5 to 60:40) to provide I-12.3.

Yield 49%, m/z 239 [M−Boc+H]+, rt 1.03 min, LC-MS Method Z011_S03.

Step 2: Synthesis of Intermediate I-12.4

To I-12.3 (10.0 g, 29.52 mmol) in ethanol (500 mL) is added sodium borohydride (2.23 g g, 59.03 mmol) and calcium chloride (6.55 g, 59.03 mmol) in two portions and the reaction mixture is stirred overnight at r.t. HPLC-MS indicated 85% conversion to the desired product. Additional amount of sodium borohydride (350 mg, 9.25 mmol) is added and the reaction mixture is stirred for 6 h at r.t. The reaction mixture is quenched with saturated sodium hydrogen carbonate solution, ethanol is removed in vacuo and obtained residue is triturated with ethyl acetate. Precipitate formed is filtered off and mother liquor is extracted with ethyl acetate several times. Combined organic layer is washed with brine, dried over $MgSO_4$, filtered and concentrated in vacuo. Obtained residue is triturated with acetonitrile, precipitate formed is filtered off, mother liquor is concentrated in vacuo and this procedure is repeated two more times. Precipitates are combined and dried in vacuo to provide I-12.4. Yield 54%, m/z 243 [M+H−Boc]+, rt 0.97 min, LC-MS Method Z011_S03.

Step 3: Synthesis of Intermediate I-12.5

To I-12.4 (6.77 g, 17.77 mmol) in dry THF (75 mL) are added TEA (14.84 mL, 106.64 mmol) and methanesulfonyl chloride (5.50 mL, 71.09 mmol) at 0° C. The reaction mixture is allowed to reach r.t. and stirred for 1 h. The reaction mixture is diluted with saturated sodium hydrogen carbonate solution and extracted with dichloromethane several times. The organic layer is washed with brine, dried over $MgSO_4$, concentrated in vacuo and obtained residue is purified by flash column chromatography (petroleum ether: EtOAc=95:5 to 72:28) to provide I-12.5.

Yield 65%, m/z 225 [M+H−Boc]+, rt 1.07 min, LC-MS Method Z011_S03.

Step 4: Synthesis of Intermediate I-12.6

To I-12.5 (4.13 g, 12.07 mmol) in dichloromethane (15 mL) is added trifluoroacetic acid (5 mL) and reaction mixture is stirred for 3 h at r.t. The reaction mixture is concentrated in vacuo, obtained residue is redissolved in methanol (50 mL), polymer-bound tetraalkyl-ammonium carbonate (Aldrich, 540293) is added and this mixture is stirred for 30 minutes at r.t. Polymer-bound tetraalkylammonium carbonate is filtered off and methanol is removed in vacuo to deliver I-12.6.

Yield 99%, m/z 225 [M+H]+, rt 0.74 min, LC-MS Method Z011_S03.

Step 5: Synthesis of R19

I-12.6 (3.62 g, 12.08 mmol) was dissolved in dry tetrahydrofurane (40 mL), 3-oxetanone (1.16 mL, 18.13 mmol) and acetic acid (691 μL, 12.08 mmol) are added and the reaction mixture is stirred for 20 minutes at r.t. Sodium triacetoxyborohydride (6.74 g, 30.21 mmol) is added and the reaction mixture is stirred for 25 min at r.t. The reaction mixture is quenched with methanol, diluted with saturated sodium hydrogen carbonate solution and extracted with ethyl acetate several times. The organic layer is washed with brine, dried over $MgSO_4$ and concentrated in vacuo. Obtained residue is triturated with acetonitrile/methanol mixture (9:1), precipitate formed is filtered off, mother liquor is concentrated in vacuo and this procedure is repeated two more times. Precipitates are combined and dried in vacuo to provide 2.47 g of R19. Mother liquor is concentrated in vacuo, obtained residue is redissolved in acetonitrile and purified by reversed phase HPLC to provide additional amount (0.32 g) of R19.

Yield 78%, m/z 281 [M+H]+, rt 0.78 min, LC-MS Method Z011_S03.

Examples (rt=retention time). Deprotection Methods: TSA (toluene sulfonic acid cf. Example 1). Stereochemistry at the carbon atom adjacent to the nitrile group is assigned: stereo bond means S-isomer.

TABLE 6
| # | Structure | Educt | Synth./ Deprot. Method | Yield [%] |
|---|---|---|---|---|
| 1 | 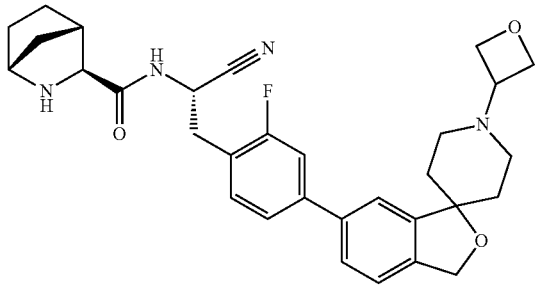 | I-1.5 | A/TSA | 84 |
| 2 | 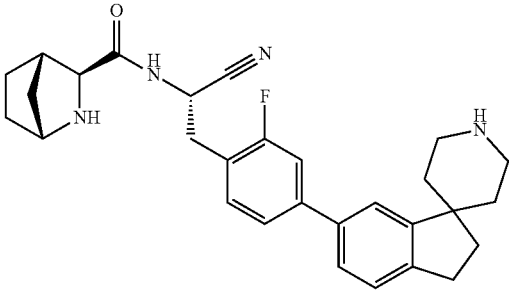 | I-1.5.1 | A/TSA | >95 |
| 3 | 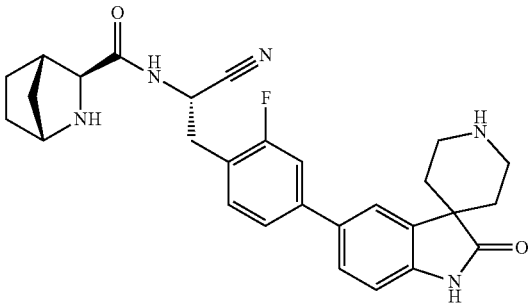 | I-1.5.2 | A/TSA | 35 |
| 4 | 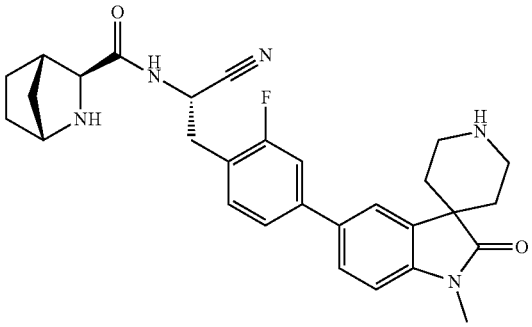 | I-1.5.3 | A/TSA | 48 |
| 5 | 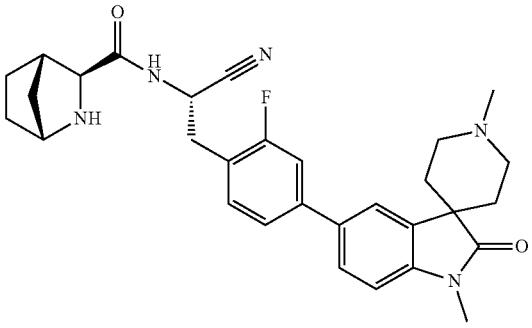 | I-1.5.4 | A/TSA | 48 |

TABLE 6-continued
| # | Structure | Educt | Synth./ Deprot. Method | Yield [%] |
|---|---|---|---|---|
| 6 | 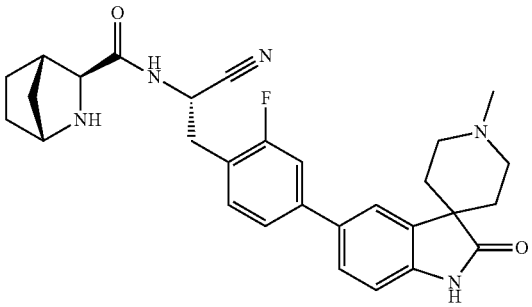 | I-1.5.5 | A/TSA | 7 |
| 7 | 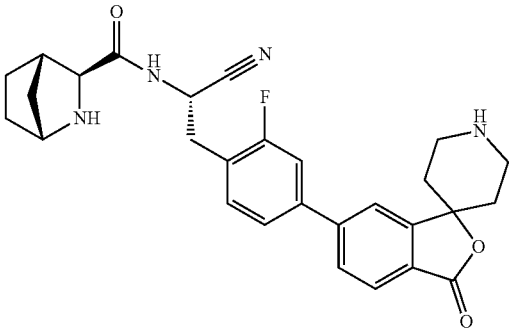 | I-1.5.6 | A/TSA | 43 |
| 8 | 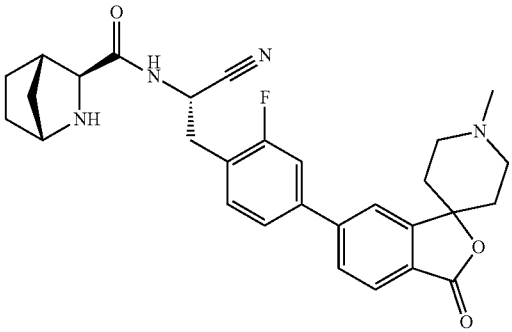 | I-1.5.7 | A/TSA | 41 |
| 9 | 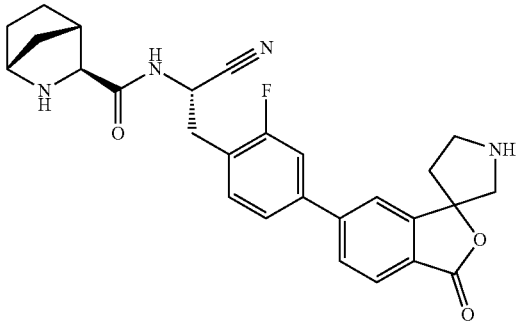 | I-1.5.8 | A/TSA | 90 |

TABLE 6-continued
| # | Structure | Educt | Synth./ Deprot. Method | Yield [%] |
|---|---|---|---|---|
| 10 | 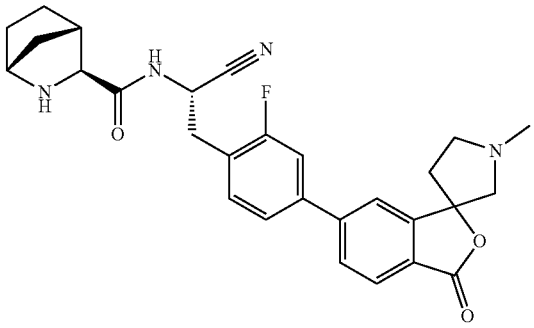 | I-1.5.9 | A/TSA | 16 |
| 11 | 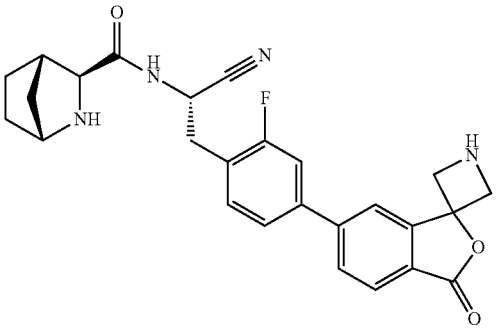 | I-1.5.10 | A/TSA | 20 |
| 12 | 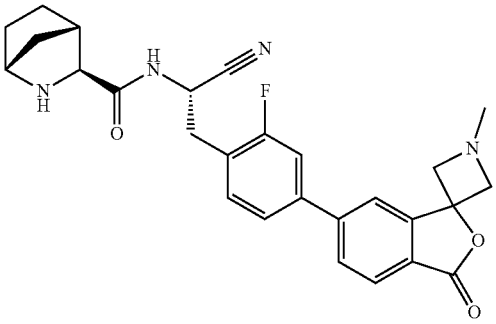 | I-1.5.11 | A/TSA | 54 |
| 13 | 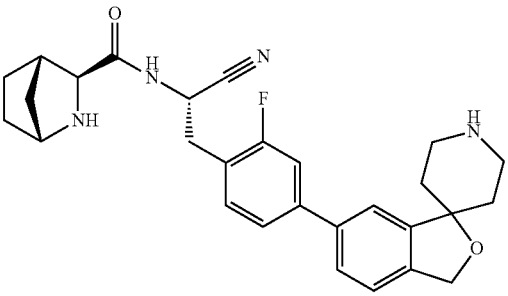 | I-1.5.12 | A/TSA | 9 |

TABLE 6-continued
| # | Structure | Educt | Synth./ Deprot. Method | Yield [%] |
|---|---|---|---|---|
| 14 | 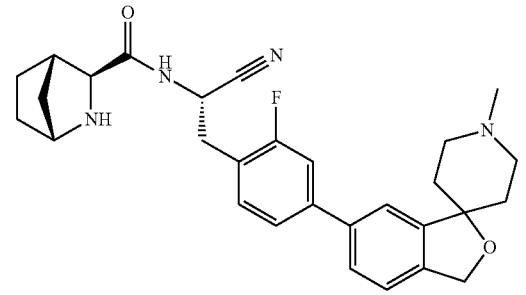 | I-1.5.13 | A/TSA | 43 |
| 15 | 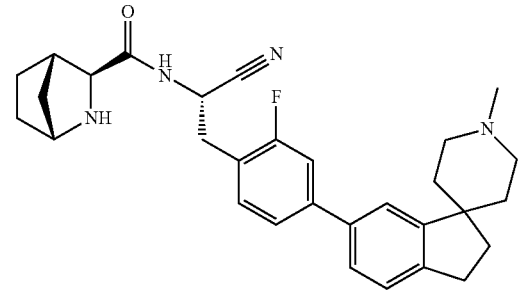 | I-1.5.14 | A/TSA | 49 |
| 16 | 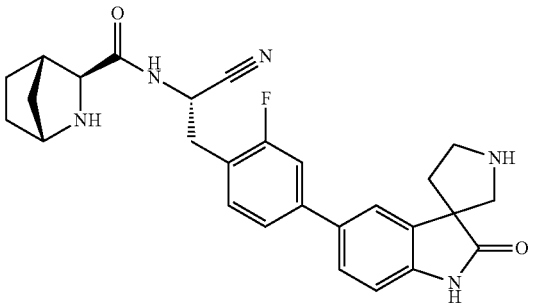 | I-1.5.15 | A/TSA | 58 |
| 17 | 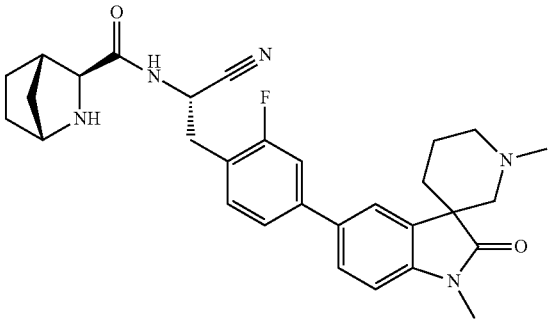 | I-1.5.16 | A/TSA | 46 |
| 18 | 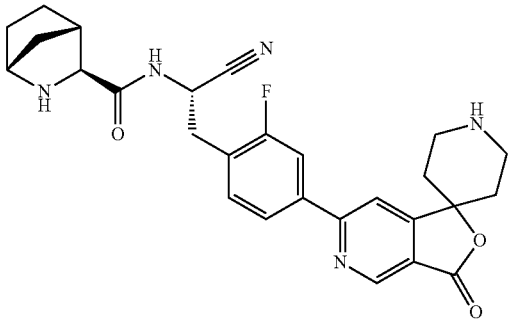 | I-1.5.17 | A/TSA | 35 |

TABLE 6-continued
| # | Structure | Educt | Synth./ Deprot. Method | Yield [%] |
|---|---|---|---|---|
| 19 | 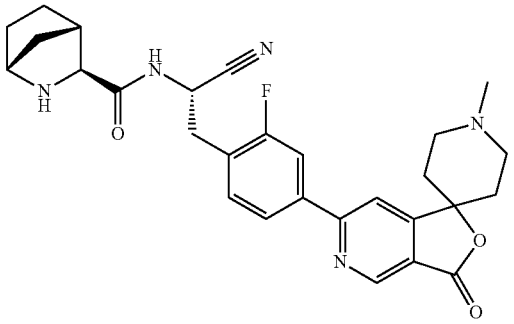 | I-1.5.18 | A/TSA | 73 |
| 20 | 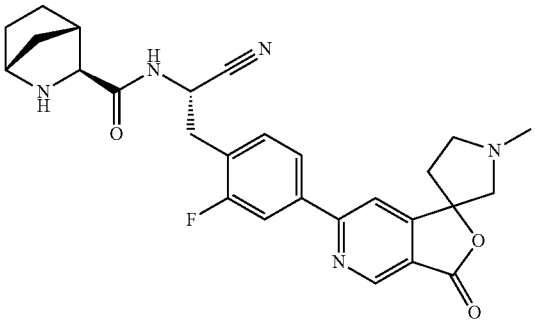 | I-1.5.19 | A/TSA | 47 |
| 21 | 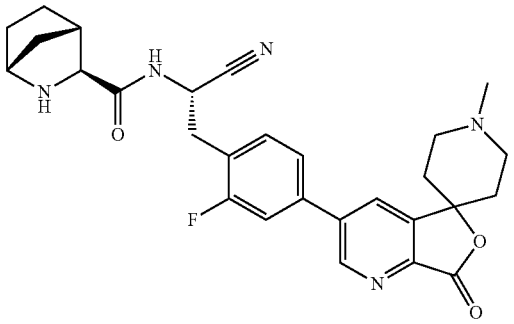 | I-1.5.20 | A/TSA | 36 |
| 22 | 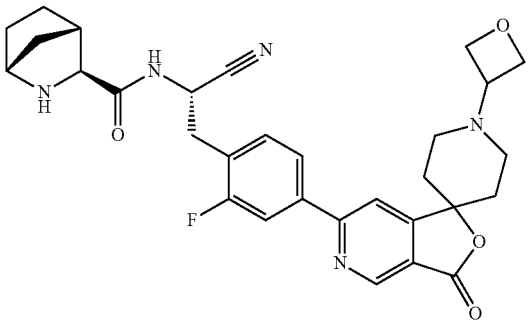 | I-1.5.21 | A/TSA | 35 |

TABLE 6-continued
| # | Structure | Educt | Synth./ Deprot. Method | Yield [%] |
|---|---|---|---|---|
| 23 | 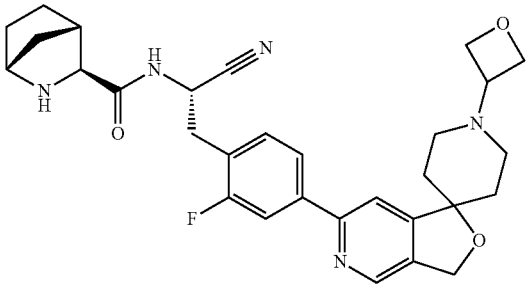 | I-1.5.22 | A/TSA | 83 |
| 24 | 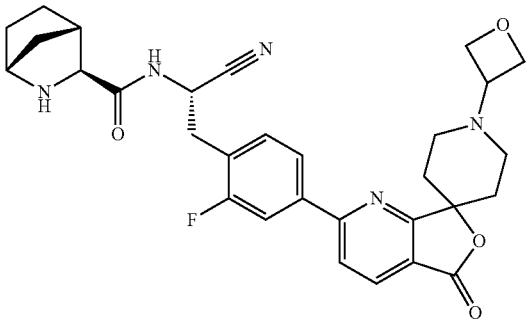 | I-1.5.23 | A/TSA | >95 |
| 25 | 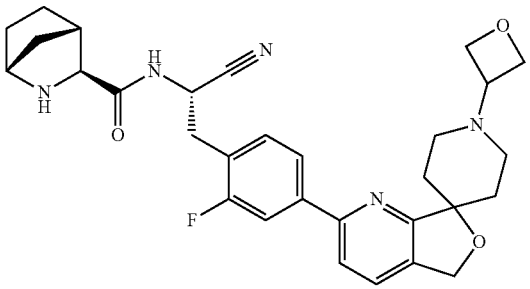 | I-1.5.24 | A/TSA | 88 |
| 26 | 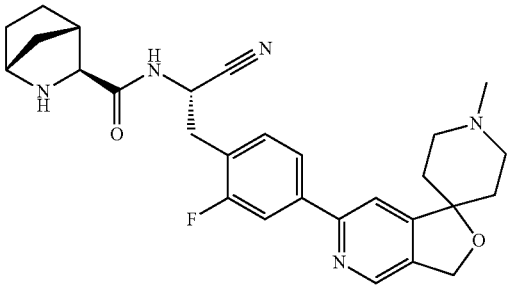 | I-2.5 | B/TSA | 28 |
| 27 | 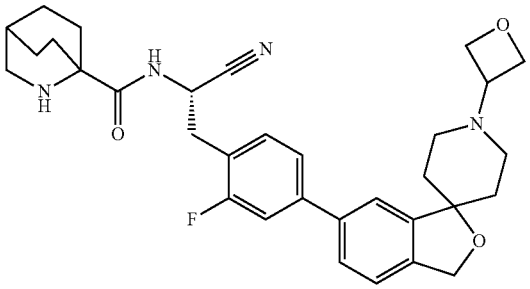 | I-3.5 | C/TSA | 61 |

TABLE 7

| Ex. | m/z [M + H]+ | rt [mm] | LC-MS-Method |
|---|---|---|---|
| 1 | 531 | 1.00 | Z011_S03 |
| 2 | 473 | 1.19 | Z011_S03 |
| 3 | 488 | 0.89 | Z012_S04 |
| 4 | 502 | 0.73 | Z012_S04 |
| 5 | 516 | 0.74 | Z012_S04 |
| 6 | 502 | 0.70 | Z012_S04 |
| 7 | 489 | 0.72 | Z012_S04 |
| 8 | 503 | 0.72 | Z012_S04 |
| 9 | 475 | 0.91 | Z011_S03 |
| 10 | 489 | 0.96 | Z011_S03 |
| 11 | 461 | 0.91 | Z011_S03 |
| 12 | 475 | 0.97 | Z011_S03 |
| 13 | 475 | 0.76 | Z012_S04 |
| 14 | 489 | 1.05 | Z011_S03 |
| 15 | 487 | 1.17 | Z011_S03 |
| 16 | 474 | 0.89 | Z011_S03 |
| 17 | 516 | 0.60 | Z020_S01 |
| 18 | 490 | 0.90 | Z011_S03 |
| 19 | 504 | 0.95 | Z011_S03 |
| 20 | 490 | 0.92 | Z011_S03 |
| 21 | 504 | 0.92 | Z011_S03 |
| 22 | 546 | 0.94 | Z011_S03 |
| 23 | 532 | 0.96 | Z011_S03 |
| 24 | 546 | 0.93 | Z011_S03 |
| 25 | 532 | 0.97 | Z011_S03 |
| 26 | 490 | 0.96 | Z011_S03 |
| 27 | 545 | 1.02 | Z011_S03 |

TABLE 8

| List of abbreviations | |
|---|---|
| ACN | acetonitrile |
| aq. | aqueous |
| BOC, boc | tert-butyloxycarbonyl |
| d | day |
| DBU | 1,8-diazabicyclo[5.4.0]undec-7-ene |
| DCM | dichloromethane |
| DEA | diethylamine |
| DIPEA | N,N-diisopropylethylamine |
| DIPE | diisopropyl ether |
| DMAP | 4-dimethylaminopyridine |
| DMF | N,N-dimethylformamide |
| DMSO | dimethyl sulfoxide |
| EA, EtOAc | ethyl acetate |
| FA | formic acid |
| h | hour |
| HATU | o-(7-azabenzotriazol-1-yl)-N,N,N',N'-tetramethyluronium hexafluoro-phosphate |
| LiOH | lithium hydroxide |
| MeOH | methanol |
| MeTHF | methyl tetrahydrofuran |
| min | minute |
| NaH | sodium hydride |
| PE | petroleum ether |
| PPA | 1-propanephosphonic acid cyclic anhydride |
| RT, r.t. | room temperature, e.g. 15-25° C. |
| rt | retention time |
| TBME | tert-butyl methyl ether |
| TBTU | o-(1H-benzo-1,2,3-triazol-1-yl)-N,N,N',N'-tetramethyluronium tetrafluoroborate |
| TEA | triethylamine |
| TFA | trifluoroacetic acid |
| THF | tetrahydrofuran |
| TSA | p-toluenesulfonic acid monohydrate |

Other features and advantages of the present invention will become apparent from the following more detailed examples which illustrate, by way of example, the principles of the invention.

Inhibition of Human DPPI (Cathepsin C)

Materials: Microtiterplates (Optiplate-384 F) were purchased from PerkinElmer (Prod. No. 10 6007270). The substrate Gly-Arg-AMC was from Biotrend (Prod.-No. 808756 Custom peptide).

Bovine serum albumin (BSA; Prod. No. A3059) and Dithiothreitol (DTT; Prod. No D0632) were from Sigma. TagZyme buffer was from Riedel-de-Haen (Prod.-No. 04269), NaCl was from Merck (Prod.-No. 1.06404.1000) and morpholinoethane sulfonic acid (MES), was from Serva (Prod.-No. 29834). The DPP1 inhibitor Gly-Phe-DMK was purchased from MP Biomedicals (Prod.-No. 03DK00625). The recombinant human DPPI was purchased from Prozymex. All other materials were of highest grade commercially available.

The following buffers were used: MES buffer: 25 mM MES, 50 mM NaCl, 5 mM DTT, adjusted to pH 6.0, containing 0.1% BSA; TAGZyme Buffer: 20 mM NaH2PO4, 150 mM NaCl adjusted to pH 20 6.0 with HCl Assay Conditions:

The recombinant human DPPI was diluted in TAGZyme buffer to 1 U/ml (38.1 μg/ml, respectively), and then activated by mixing in a 1:2 ratio with a Cysteamine aqueous solution (2 mM) and incubating for 5 min at room temperature. Five uL test compound (final concentration 0.1 nM to 100 μM) in aqua bidest 5 (containing 4% DMSO, final DMSO concentration 1%) were mixed with 10 μL of DPPI in MES buffer (final concentration 0.0125 ng/μL) and incubated for 10 min. Then, 5 μL of substrate in MES buffer (final concentration 50 μM) were added. The microtiter plates were then incubated at room temperature for 30 min. Then, the reaction was stopped by adding 10 μL of Gly-Phe-DMK in 10 MES-buffer (final concentration 1 μM). The fluorescence in the wells was determined using a Molecular Devices SpectraMax M5 Fluorescence Reader (Ex 360 nm, Em 460 nm) or an Envision Fluorescence Reader (Ex 355 nm, Em 460 nm).

Each assay microtiter plate contained wells with vehicle controls (1% DMSO in bidest+0.075% 15 BSA) as reference for non-inhibited enzyme activity (100% Ctl; high values) and wells with inhibitor (Gly-Phe-DMK, in bidest+1% DMSO+0.075% BSA, final concentration 1 μM) as controls for background fluorescence (0% Ctl; low values). The analysis of the data was performed by calculating the percentage of fluorescence in the presence of test compound in comparison to the fluorescence of the vehicle control after 20 subtracting the background fluorescence using the following formula:

(RFU(sample)−RFU(background))*100/(RFU(control)−RFU(background))

Data from these calculations were used to generate IC50 values for inhibition of DPPI, respectively.

TABLE 9

| Example | Inhibition of DPPI $IC_{50}$ [μM] |
|---|---|
| 1 | 0.0011 |
| 2 | 0.0006 |

TABLE 9-continued

| Example | Inhibition of DPPI $IC_{50}$ [μM] |
|---|---|
| 3 | 0.0003 |
| 4 | 0.0004 |
| 5 | 0.0006 |
| 6 | 0.0002 |
| 7 | 0.0005 |
| 8 | 0.0007 |
| 9 | 0.0005 |
| 10 | 0.0006 |
| 11 | 0.0007 |
| 12 | 0.0005 |
| 13 | 0.0006 |
| 14 | 0.0010 |
| 15 | 0.0005 |
| 16 | 0.0005 |
| 17 | 0.0016 |
| 18 | 0.0016 |
| 19 | 0.0010 |
| 20 | 0.0016 |
| 21 | 0.0014 |
| 22 | 0.0048 |
| 23 | 0.0050 |
| 24 | 0.0027 |
| 25 | 0.0018 |
| 26 | 0.0020 |
| 27 | 0.0029 |

Determination of Neutrophil Elastase Activity in U937 Cytosolic Lysate Preparation after Incubation with Test Compound Materials:

Optiplate 384F were purchased from PerkinElmer (Prod. No. #6007270). 24 well Nunclon cell culture plates (No. 142475) and 96 well plates (No. 267245) were from Nunc.

Dimethylsulfoxid (DMSO) was from Sigma (Prod. No. D8418). Nonidet-P40 (NP40) was from USBiological (Prod. No. N3500)

Substrate, specific for Neutrophil elastase, was from Bachem (MeOSuc-Ala-Ala-Pro-Val-AMC; Prod. No. I-1270).

Human neutrophil elastase was from Calbiochem (Prod. No. 324681)

Buffers:

Tris-buffer (100 mM Tris; 1M NaCl; pH 7.5)

Tris-buffer+HSA 0.1%; Human Serum Albumin from Calbiochem (Cat#. 126658)

Serine-protease buffer (20 mM Tris; 100 mM NaCl; pH 7.5)+0.1% HSA

Serine protease lysis buffer: 20 mM Tris-HCl; 100 mM NaCl pH 7.5; +0.2% Nonidet-P40;

PBS: phosphate buffered saline, without Ca and Mg, from Gibco

Cell Culture:

U937 from ECACC (Cat. No. 85011440) cultured in suspension at 37° C. and 5% CO2.

Cell density: 0.2-1 Mio. Cells/ml.

Medium: RPMI1640 GlutaMAX (No. 61870) with 10% FCS from Gibco

Cell Seeding and Treatment:

Compounds in 100% DMSO were diluted in Medium (−FCS) with 10% DMSO and further diluted according to the experiment planned.

20 μl of the compound solution was transferred in the respective wells of the 24 well plate and diluted with 2 ml cell suspension/well containing $1\times10^5$ cells/ml (final concentration of DMSO=0.1%). Compound dilution factor=100

Compounds (up to 7 concentrations) were tested in triplicates with 3 wells for the DMSO 0.1% control, incubated for 48 hours without medium change at 37° C., 5% CO2 and 95% relative humidity.

Cell Harvesting and Cell Lysate:

Transfer the cell suspension in 2 ml 96 well assay block. Separate cells from medium by centrifugation (500×g; 10 min; RT); discard the supernatant. Resuspend in 1 ml PBS; centrifugation (500×g; 10 min; RT); wash cells twice with PBS. Add 80 μl Serine protease lysis buffer (ice cold) to the cell pellet; resuspend the pellet and store on ice for 10 minutes. Remove debris by centrifugation at 1000×g for 10 min at 4° C. Transfer 80-100 μl lysate supernatant in 96 well plate and store immediately at −80° C.

Neutrophil Elastase Activity Assay:

Frozen lysates were thaw at 37° C. for 10 minutes and stored on ice. Protein content was determined with Bradford protein assay. Lysates were diluted to 0.2-0.5 mg/ml protein in serine protease buffer+HSA.

Standard: NE (100 μg/ml stock solution in Tris-buffer; stored at −80° C.) was diluted in Tris-buffer+HSA to 750 ng/ml, and further serially diluted 1:2 for the standard curve. Buffer, blank, standard and lysate samples were transferred into 384 well plate Pipetting Plan Blank: 5 μl Tris-buffer+10 μl Serine protease buffer+5 μl Substrate Standard: 5 μl Tris-buffer+10 μl NE (diff. conc.)+5 μl Substrate Lysate: 5 μl Tris-buffer+10 μl Lysat+5 μl Substrate The increase in fluorescence (Ex360 nm/Em 460 nm) is determined after 30 minutes with a Molecular Device Spectramax M5 Fluorescence Reader. The result is interpolated to ng/mg lysate protein using excel formula functions. Percent inhibition in the compound-treated lysate samples is calculated relative to the DMSO-treated control-sample (100−(compound-sample*100)/control-sample)

A test compound will give values between 0% and 100% inhibition of neutrophil elastase. IC50 is calculated using Graphpad Prism; nonlinear fitting (log(inhibitor) vs. response—Variable slope). The IC50 value is interpolated as the concentration of test compound which leads to a neutrophil elastase activity reduction of 50% (relative to the DMSO-treated control).

TABLE 10

| Example | Reduction of NE-activity in U937 cells IC50 [μM] |
|---|---|
| 1 | 0.0010 |
| 2 | 0.0068 |
| 3 | 0.5030 |
| 4 | 0.0910 |
| 5 | 0.0023 |
| 6 | 0.0222 |
| 7 | 0.0349 |
| 8 | 0.0008 |
| 9 | 0.0215 |
| 10 | 0.0014 |
| 11 | 0.0107 |
| 12 | 0.0012 |
| 13 | 0.0167 |
| 14 | 0.0011 |
| 15 | 0.0002 |
| 16 | 0.0738 |
| 17 | 0.0006 |
| 18 | 0.2202 |
| 19 | 0.0050 |
| 20 | 0.0232 |
| 21 | 0.0637 |
| 22 | 0.0157 |
| 23 | 0.0075 |
| 24 | 0.0060 |
| 25 | 0.0016 |

TABLE 10-continued

| Example | Reduction of NE-activity in U937 cells IC50 [μM] |
|---|---|
| 26 | 0.0046 |
| 27 | 0.0007 |

Inhibition of Human Cathepsin K

Materials:

Microtiterplates (Optiplate-384 F were purchased from PerkinElmer (Prod. No. 6007270). The substrate Z-Gly-Pro-Arg-AMC was from Biomol (Prod.-No. P-142). L-Cysteine (Prod. No. 168149) was from Sigma. Sodium actetate was from Merck (Prod.-No. 6268.0250), EDTA was from Fluka (Prod.-No. 03680). The inhibitor E-64 was purchased from Sigma (Prod.-No. E3132). The recombinant human Cathepsin K proenzyme was purchased from Biomol (Prod. No. SE-367). All other materials were of highest grade commercially available.

The following buffers were used: Activation buffer: 32.5 mM sodium acetate, adjusted to pH 3.5 with HCl; Assay buffer: 150 mM sodium acetate, 4 mM EDTA, 20 mM L-Cysteine, adjusted to pH 5.5 with HCl, Assay Conditions:

To activate the proenzyme, 5 μl procathepsin K were mixed with 1 ul activation buffer, and incubated at room temperature for 30 min.

5 μL test compound (final concentration 0.1 nM to 100 μM) in aqua bidest (containing 4% DMSO, final DMSO concentration 1%) were mixed with 10 μL of Cathepsin K in assay buffer (final concentration 2 ng/μL) and incubated for 10 min. Then 5 μL of substrate in assay buffer (final concentration 12.5 μM) were added. The plates were then incubated at room temperature for 60 min. Then, the reaction was stopped by adding 10 μL of E64 in assay buffer (final concentration 1 μM). The fluorescence in the wells was determined using a Molecular Devices SpectraMax M5 Fluorescence Reader (Ex 360 nm, Em 460 nm).

Each assay microtiter plate contains wells with vehicle controls (1% DMSO in bidest) as reference for non-inhibited enzyme activity (100% Ctl; high values) and wells with inhibitor (E64 in bidest+1% DMSO, final concentration 1 μM) as controls for background fluorescence (0% Ctl; low values). The analysis of the data was performed by calculating the percentage of fluorescence in the presence of test compound in comparison to the fluorescence of the vehicle control after subtracting the background fluorescence:

(RFU(sample)−RFU(background))*100/(RFU(control)−RFU(background))

Data from these calculations were used to generate $IC_{50}$ values for inhibition of Cathepsin K, respectively.

Determination of Metabolic Stability with Human Liver Microsomes

The metabolic degradation of the test compound is assayed at 37° C. with pooled human liver microsomes. The final incubation volume of 100 μl per time point contains TRIS buffer pH 7.6 (0.1 M), magnesium chloride (5 mM), microsomal protein (1 mg/ml) and the test compound at a final concentration of 1 μM. Following a short preincubation period at 37° C., the reactions are initiated by addition of beta-nicotinamide adenine dinucleotide phosphate, reduced form (NADPH, 1 mM) and terminated by transferring an aliquot into acetonitrile after different time points. Additionally, the NADPH-independent degradation is monitored in incubations without NADPH, terminated at the last time point. The [%] remaining test compound after NADPH independent incubation is reflected by the parameter c (control) (metabolic stability). The quenched incubations are pelleted by centrifugation (10'000 g, 5 min.) An aliquot of the supernatant is assayed by LC-MS/MS for the amount of parent compound.

The half-life (t1/2 INVITRO) is determined by the slope of the semilogarithmic plot of the concentration-time profile. The intrinsic clearance (CL_INTRINSIC) is calculated by considering the amount of protein in the incubation:

CL_INTRINSIC [μl/min/mg protein]=(ln 2/(half-life [min]*protein content [mg/ml]))*1'000.

The half-life (t½ INVITRO) values of selected compounds in the metabolic stability assay described above are listed in the following table.

TABLE 11

| Example | In vitro stability in human liver microsome incubations t½ [min] |
|---|---|
| 1 | >130 |
| 2 | >130 |
| 3 | >130 |
| 4 | >130 |
| 5 | >130 |
| 6 | 110 |
| 7 | >130 |
| 8 | 74 |
| 9 | >130 |
| 10 | >130 |
| 11 | >130 |
| 12 | 46 |
| 13 | >130 |
| 14 | >130 |
| 15 | >130 |
| 16 | >130 |
| 17 | 60 |
| 18 | >130 |
| 19 | >130 |
| 20 | >130 |
| 21 | >130 |
| 22 | >130 |
| 23 | >130 |
| 24 | >130 |
| 25 | >130 |
| 26 | 55 |
| 27 | 120 |

Target Engagement Mouse Model

Compound Treatment:

To monitor the effect of the test compounds on neutrophil elastase activity in peripheral neutrophils, female Crl:NMRI mice were treated as follows:

Group 1 (6 animals): 0.5 mg/kg test compound in 0.5% Natrosol (pH 2-3)

Group 2 (6 animals): 0.5% Natrosol (pH 2-3)

Group 3 (2 animals): 0.5% Natrosol (pH 2-3)

Test compounds or Natrosol solution were applied on Monday to Friday at 7:00 am and 4:00 pm each day of the first week of the study and on Monday and Tuesday (7:00 am and 4:00 pm) the second week. Test compounds or Natrosol were applied orally.

LPS Challenge and Bronchioalveolar Lavage Preparation:

On Wednesday the second week, animals were treated with test compound or Natrosol solution as described above (7:00 am) followed by a LPS (lipopolysaccharide) inhalation challenge:

Group 1 and 2: 20 minutes inhalation of LPS (E. coli Serotype 055:B5; 1 mg/ml in PBS) using a MiniHeart Hi-Flo continuous nebulizer (Westmed)

Group 3: No LPS challenge 4 hours after the LPS challenge a bronchioalveolar lavage using 2×1 ml Hank's salt solution per animal was prepared from all animals and the cell numbers in the lavage fluid determined using a Sysmex XT-1800i. The cells in the lavage fluid were separated by centrifugation and lysed in lysis buffer (100 mM TRIS pH 7.5, 1 M NaCl, 0.2% NP40).

Neutrophile Elastase (NE) Measurement:

NE activity in the BALF (bronchioalveolar lavage fluid) cell lysate was measured using the fluorescent NE substrate MeOSuc-Ala-Ala-Pro-Val-AMC (Bachem): 10 μl cell lysate were mixed with 5 μl assay buffer (20 mM Tris pH 7.5, 100 mM NaCl, 0.1% human serum albumin) and 5 μl substrate (1 mM in assay buffer) in a 384 well plate (Optiplate 384f, PerkinElmer). The reaction mixture was incubated for 60 min at room temperature and the fluorescence measured (360 nm excitation, 460 nm emission). The obtained fluorescence values were normalized to the BALF neutrophil numbers for each animal. To calculate the inhibition of NE activity by test compounds, the mean fluorescence value of group 3 was subtracted from the fluorescence values for group 1 and 2 and the % inhibition of NE activity in group 1 compared to the mean fluorescence value in group 2 calculated.

Neutrophil elastase activity in BALF lysate after the pretreatment with Cathepsin C inhibitors (7 d bid (twice a day) administration) are listed in the following table:

TABLE 12

| Example | Inhibition of neutrophil elastase activity in BALF lysate after the pretreatment with Cathepsin C inhibitor (dosage: 0.5 mg/kg bid for 7 days) |
|---|---|
| 1 | 96 |
| 25 | 94 |

Crystal Structures of Cathepsin C Ligand Complexes

Methods

Protein:

Recombinant human Cathepsin C (Cat C) was produced according to standard molecular biological protocols (Literature: 1-3).

Crystallization and Soaking:

Prior to crystallization protein buffer was exchanged to 20 mM Bis-Tris pH 7.0, 150 mM NaCl, 2 mM EDTA, 2 mM DTT with a NAP10 column (GE Healthcare). The protein sample was concentrated to 9-10 mg/mL. Crystals were grown at 20° C. in hanging drops using 1.0 μL of protein and 1.0 μL of well solution (0.1 M Bis-Tris-Propane pH 6.0-6.5, 18-20% (w/v) PEG 3350, 200 mM NaF, 1 mM DDT). Crystals appeared overnight and grew to full size within 2-3 days. Ligand co-structures were obtained by soaking apo-crystals in well solution supplemented with 1 mM of the respective ligand (via dilution from 100 mM stock solution in DMSO) overnight. Crystals were then frozen in liquid nitrogen prior to data collection using 20% glycerol and well solution as cryo protectant.

Data Collection, Structure Solution and Refinement:

All diffraction data were collected at 100 K on a rotating anode generator (Rigaku) using CuKα radiation and processed with XDS (Literature: 4). Ligand co-structures were solved by the difference fourier method and refined with program autoBuster (Global Phasing Ltd.) iterated with manual rebuilding using the program coot (Literature: 5). The final data processing and refinement statistics are listed in Table 13. The program PyMOL (DeLano Scientific LLC) was used for figure preparation.

Results

Structure of Cathepsin C Ligand Complexes:

The structure of human Cathepsin C (Cat C) is described in the literature (Literature 2) as a tetramer containing four identical subunits. Each subunit is comprised of three chains: light and heavy chains form the catalytic domain, while the so-called exclusion domain blocks the active site cleft beyond the S2 pocket and is responsible for the exopeptidase activity of Cat C. The structures of Cat C in complex with Examples 11 and 16 (Table 14, FIG. 1) were determined to elucidate the binding mode of this class of compounds. Examples 11 and 16 bind via a covalent interaction of the nitrile group with Cys234. Example 11 is a single enantiomer with the carbon atom adjacent to the nitrile group in (S) configuration while Example 16 (spirocyclic carbon atom has RS stereochemistry) is a mixture of diastereomers. The bicyclic amino acid reaches into the enzyme 51 pocket where it is anchored via hydrogen bonds to backbone atoms of Gly277 and Asn380 as well as to the side chain of Asp1. The bis-aryl system is oriented into the S2 pocket where it is involved in van der Waals interactions to residues Asp1 and Pro3 of the exclusion domain. Surprisingly, we observed an additional interaction of the spirocyclic amine: spiro-azetidine in Example 11 and spiro-pyrrolidine in Example 16. In both cases the basic nitrogen atom forms a salt-bridge to Glu275 consistent with the high enzyme activity of this compound class.

REFERENCES (1) Søren W. Dahl, Torben Halkier, Conni Lauritzen, Iztok Dolenc, John Pedersen, Vito Turk and Boris Turk. (2001) Human Recombinant Pro-dipeptidyl Peptidase I (Cathepsin C) Can Be Activated by Cathepsins L and S but Not by Autocatalytic Processing. Biochemistry 40, 1671-1678.

(2) Dusan Turk, Vojko Janjic, Igor Stern, Marjetka Podobnik, Doriano Lamba, Sùren Weis Dahl, Connie Lauritzen, John Pedersen, Vito Turk and Boris Turk (2001) Structure of human dipeptidyl peptidase I (cathepsin C): exclusion domain added to an endopeptidase framework creates the machine for activation of granular serine proteases. The EMBO Journal 20, 6570-6582.

(3) Furber, M. et al. (2014) Cathepsin C Inhibitors: Property Optimization and Identification of a Clinical Candidate. J. Med. Chem., 57, 2357-2367.

(4) Kabsch, W. (2010) XDS. Acta Crystallogr. D. Biol. Crystallogr. 66, 125-132.

(5) Emsley, P. & Cowtan, K. (2004) Coot: model-building tools for molecular graphics. Acta Crystallogr. D. Biol. Crystallogr. 60, 2126-2132.

TABLE 13

Data Collection and Refinement Statistics

| Data collection[1] | | |
|---|---|---|
| Data set | Example 11 | Example 16 |
| Detector | Saturn944 | Mar345 |
| Space Group | 1222 | 1222 |
| Unit cell dimensions | | |
| a, b, c (Å) | 86.0, 89.3, 114.6 | 86.5, 88.7, 114.5 |
| Resolution (Å) | 1.7 | 1.5 |

TABLE 13-continued

| Data Collection and Refinement Statistics | | |
|---|---|---|
| Completeness (%) | 81.0 (9.1) | 93.3 (43.5) |
| $R_{sym}$ (%) | 4.2 (31.6) | 3.5 (28.0) |
| <I/σ(I)> | 32.1 (2.9) | 32.5 (4.7) |
| Refinement[2] | | |
| R-factor/R-free (%) | 17.8/19.2 | 21.3/21.7 |
| Rmsd bond length (Å) | 0.008 | 0.008 |
| Rmsd bond angles (°) | 0.90 | 0.93 |

[1]Values in parentheses are for the highest resolution shell; $R_{sym} = \Sigma_{hkl}\Sigma_i|I_i-\langle I\rangle/\Sigma_{hkl}\Sigma_i I_i$
[2]R-factor = Σhkl | | Fobs | -k | Fcalc | | /Σhkl | Fobs | ; R-free was calculated using 5% of data excluded from refinement; Rmsd, root mean square deviation.

tors of non-receptor tyrosine kinases as for example LYN, LCK, SYK, ZAP-70, FYN, BTK or ITK, inhibitors of MAP kinases as for example p38, ERK1, ERK2, JNK1, JNK2, JNK3 or SAP, inhibitors of the NF-κB signalling pathway as for example IKK2 kinase inhibitors, iNOS inhibitors, MRP4 inhibitors, leukotriene biosynthese inhibitors as for example 5-Lipoxygenase (5-LO) inhibitors, cPLA2 inhibitors, Leukotriene A4 Hydrolase inhibitors or FLAP inhibitors, Non-steroidal anti-inflammatory agents (NSAIDs), CRTH2 antagonists, DP1-receptor modulators, Thromboxane receptor antagonists, CCR3 antagonists, $CCR^4$ antagonists, CCR1 antagonists, CCR5 antagonists, CCR6 antagonists, CCR7 antagonists, CCR8 antagonists, CCR9 antagonists, CCR30 antagonists, $CXCR^3$ antagonists, $CXCR^4$ antagonists,

TABLE 14

Compounds examined in X-ray crystallography

| Compound | Example 11 | Example 16 |
|---|---|---|
| Structure | 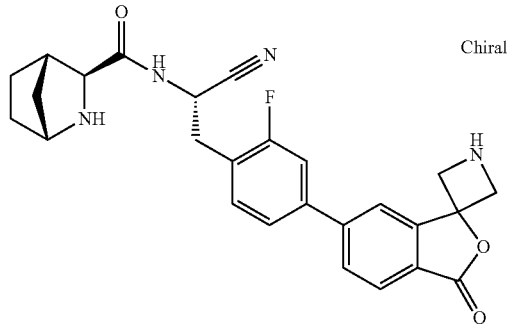 Chiral | 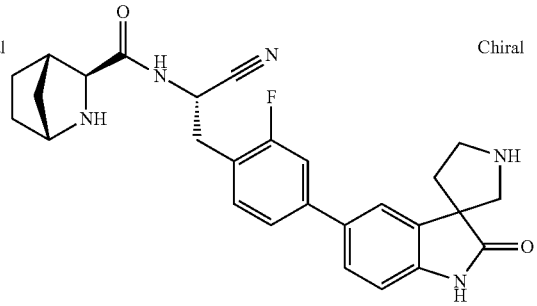 Chiral |
| Stereo isomer | single diastereomer | mixture of diastereomers |
| CatC $IC_{50}$ (nM) | 0.7 | 0.5 |

Pharmaceutical Compositions

Suitable preparations for administering the compounds of formula I will be apparent to those with ordinary skill in the art and include for example tablets, pills, capsules, suppositories, lozenges, troches, solutions, syrups, elixirs, sachets, injectables, inhalatives and powders etc., preferably tablets.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

Combinations

The compounds of general formula I may be used on their own or combined with other active substances of formula I according to the invention. The compounds of general formula I may optionally also be combined with other pharmacologically active substances. These include, β2-adrenoceptor-agonists (short and long-acting), anti-cholinergics (short and long-acting), anti-inflammatory steroids (oral and topical corticosteroids), cromoglycate, methylxanthine, dissociated-glucocorticoidmimetics, PDE3 inhibitors, PDE4-inhibitors, PDE7-inhibitors, LTD4 antagonists, EGFR-inhibitors, Dopamine agonists, PAF antagonists, Lipoxin A4 derivatives, FPRL1 modulators, LTB4-receptor (BLT1, BLT2) antagonists, Histamine H1 receptor antagonists, Histamine H4 receptor antagonists, dual Histamine H1/H3-receptor antagonists, PI3-kinase inhibitors, inhibi- $CXCR^2$ antagonists, $CXCR^1$ antagonists, CXCR5 antagonists, CXCR6 antagonists, $CX3CR^3$ antagonists, Neurokinin (NK1, NK2) antagonists, Sphingosine 1-Phosphate receptor modulators, Sphingosine 1 phosphate lyase inhibitors, Adenosine receptor modulators as for example A2a-agonists, modulators of purinergic rezeptors as for example P2X7 inhibitors, Histone Deacetylase (HDAC) activators, Bradykinin (BK1, BK2) antagonists, TACE inhibitors, PPAR gamma modulators, Rho-kinase inhibitors, interleukin 1-beta converting enzyme (ICE) inhibitors, Toll-Like receptor (TLR) modulators, HMG-CoA reductase inhibitors, VLA-4 antagonists, ICAM-1 inhibitors, SHIP agonists, GABAa receptor antagonist, ENaC-inhibitors, Prostasin-inhibitors, Matriptase-inhibitors, Melanocortin receptor (MC1R, MC2R, MC3R, MC4R, MC5R) modulators, CGRP antagonists, Endothelin antagonists, TNF□ antagonists, anti-TNF antibodies, anti-GM-CSF antibodies, anti-CD46 antibodies, anti-IL-1 antibodies, anti-IL-2 antibodies, anti-IL-4 antibodies, anti-IL-5 antibodies, anti-IL-13 antibodies, anti-IL-4/IL-13 antibodies, anti-TSLP antibodies, anti-OX40 antibodies, mucoregulators, immunotherapeutic agents, compounds against swelling of the airways, compounds against cough, VEGF inhibitors, NE-inhibitors, MMP9 inhibitors, MMP12 inhibitors, but also combinations of two or three active substances.

Preferred are betamimetics, anticholinergics, corticosteroids, PDE4-inhibitors, LTD4-antagonists, EGFR-inhibitors, CRTH2 inhibitors, 5-LO-inhibitors, Histamine receptor antagonists and SYK-inhibitors, NE-inhibitors, MMP9 inhibitors, MMP12 inhibitors, but also combinations of two or three active substances, i.e.:

Betamimetics with corticosteroids, PDE4-inhibitors, CRTH2-inhibitors or LTD4-antagonists, Anticholinergics with betamimetics, corticosteroids, PDE4-inhibitors, CRTH2-inhibitors or LTD4-antagonists, Corticosteroids with PDE4-inhibitors, CRTH2-inhibitors or LTD4-antagonists PDE4-inhibitors with CRTH2-inhibitors or LTD4-antagonists CRTH2-inhibitors with LTD4-antagonists.

Indications

The compounds of the invention and their pharmaceutically acceptable salts have activity as pharmaceuticals, in particular as inhibitors of dipeptidyl peptidase I activity, and thus may be used in the treatment of:

1. respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; alpha1 -antitrypsin deficiency, bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, polyangiitis (Wegener Granulomatosis) and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

2. skin: psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

3. eyes: blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial;

4. genitourinary: nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female);

5. allograft rejection: acute and chronic following, for example, transplantation of kidney, heart, liver, lung, bone marrow, skin or cornea or following blood transfusion; or chronic graft versus host disease;

6. other auto-immune and allergic disorders including rheumatoid arthritis, irritable bowel syndrome, systemic lupus erythematosus, multiple sclerosis, Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome and Sazary syndrome;

7. oncology: treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes; and, 8. infectious diseases: virus diseases such as genital warts, common warts, plantar warts, hepatitis B, hepatitis C, herpes simplex virus, molluscum contagiosum, variola, human immunodeficiency virus (HIV), human papilloma virus (HPV), cytomegalovirus (CMV), varicella zoster virus (VZV), rhinovirus, adenovirus, coronavirus, influenza, parainfluenza; bacterial diseases such as tuberculosis and mycobacterium avium, leprosy; other infectious diseases, such as fungal diseases, chlamydia, Candida, aspergillus, cryptococcal meningitis, Pneumocystis carnii, cryptosporidiosis, histoplasmosis, toxoplasmosis, trypanosome infection and leishmaniasis.

9. pain: Recent literature data from Cathepsin C-deficient mice point to a modulatory role of Cathepsin C in pain sensation. Accordingly, inhibitors of Cathepsin C may also be useful in the clinical setting of various form of chronic pain, e.g. inflammatory or neuropathic pain.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the active ingredient will be administered at dosages and in a manner which allows a pharmaceutically effective amount to be delivered based upon patient's unique condition.

What is claimed:

1. A compound of formula I or a pharmaceutically acceptable salt thereof,

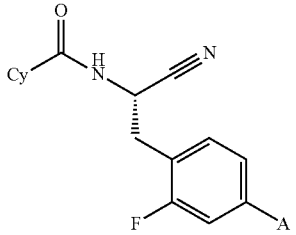

wherein

Cy is

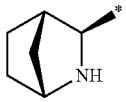

or

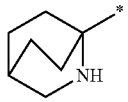

;

A is

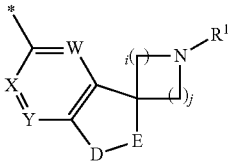

wherein

W is selected from the group consisting of CH and N;

X is selected from the group consisting of CH and N;

Y is selected from the group consisting of CH and N;

with the proviso that a maximum of one of W, X and Y can be N;

D-E is selected from the group consisting of $N(R^2)$—C(O), $CH_2CH_2$, C(O)—O and $CH_2$—O;

$R^2$ is selected from the group consisting of H and $C_{1-3}$-alkyl;

$R^1$ is selected from the group consisting of H, $C_{1-3}$-alkyl, $CH_3OCH_2CH_2$—, oxetanyl, tetrahydrofuranyl, 4-tetrahydropyranyl and 3-tetrahydropyranyl;

i is 1, 2 or 3;

j is 1, 2 or 3;

with the proviso that the sum of i+j is 2, 3 or 4.

2. A compound of formula I according to claim 1, or a pharmaceutically acceptable salt thereof, wherein Cy is

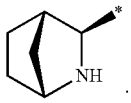

.

3. A compound of formula I according to claim 1, or a pharmaceutically acceptable salt thereof, wherein Cy is

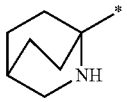

.

4. A compound of formula I according to claim 1, or a pharmaceutically acceptable salt thereof, wherein $R^1$ is selected from the group consisting of H, $CH_3$— and oxetanyl.

5. A compound of formula I according to claim 1, or a pharmaceutically acceptable salt thereof, wherein $R^2$ is selected from the group consisting of H and $CH_3$.

6. A compound of formula I according to claim 1, or a pharmaceutically acceptable salt thereof, wherein D-E is $CH_2$—O.

7. A compound of formula I according to claim 1, or a pharmaceutically acceptable salt thereof, wherein $R^1$ is selected from the group consisting of H, $CH_3$ and oxetanyl;

$R^2$ is $CH_3$,

W is selected from the group consisting of CH and N;

X is selected from the group consisting of CH and N;

Y is [selected from the group consisting of] CH;

with the proviso that a maximum of one of W[,] *and* X [and Y] can be N;

D-E is selected from the group consisting of $N(R^2)$—C(O), $CH_2CH_2$, C(O)—O and $CH_2$—O;

i is 1 or 2;

j is 1 or 2;

with the proviso that the sum of i+j is 2, 3 or 4.

8. A compound of formula I according to claim 1, or a pharmaceutically acceptable salt thereof, wherein A is selected from the group consisting of formulas A1, A2, A3, A4, A5, A6, A7, A8, A9, A10, A11, A12, A13 and A14 (shown below):

A1

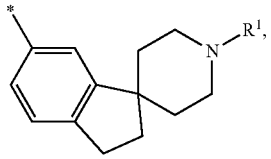

A2

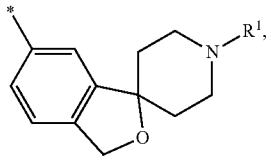

A3

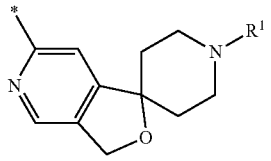

A4

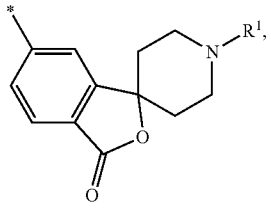

-continued
A5
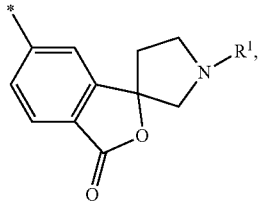
A6
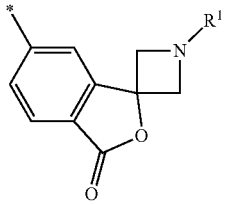
A7
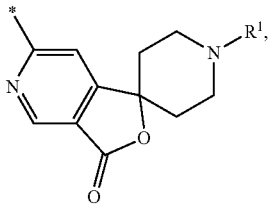
A8
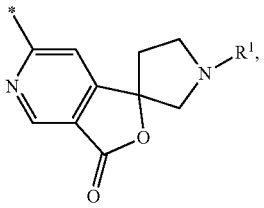
A9
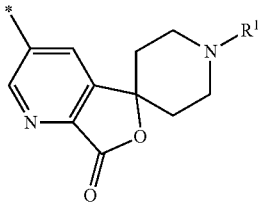
A10
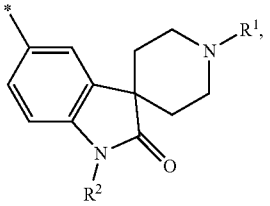
A11
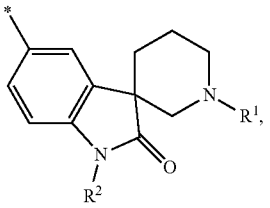
-continued
A12
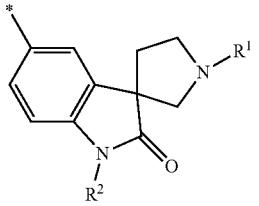
A13
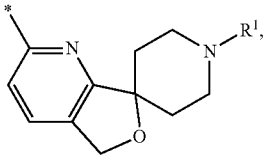
A14
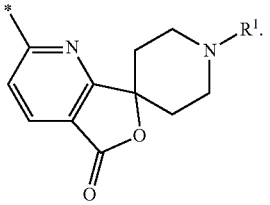
9. A compound of formula I according to claim 8, or a pharmaceutically acceptable salt thereof, wherein
A is selected from the group consisting of A2, A3, A4, A5, A6, A7, A10, A13 and A14 (shown below):
A2
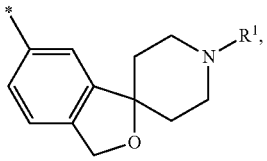
A3
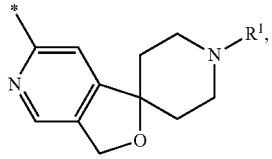
A4
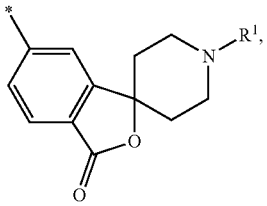
A5
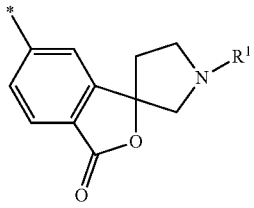

-continued
A6
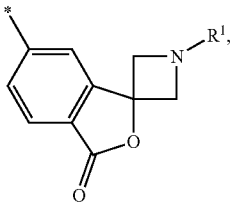
A7
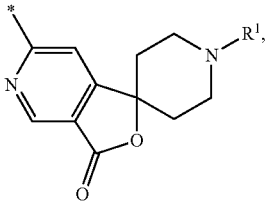
A10
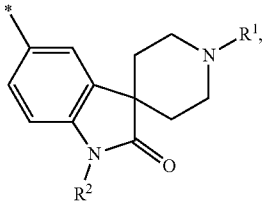
A13
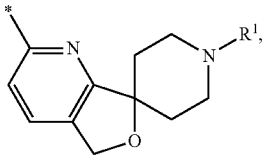
A14
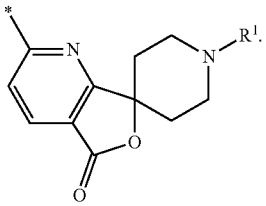
10. A compound of formula I according to claim 8, or a pharmaceutically acceptable salt thereof, wherein
A is selected from the group consisting of A2 and A13 (shown below):
A2
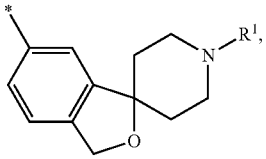
A13
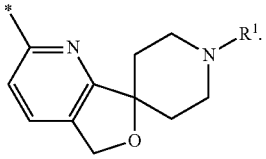
11. A compound [of formula I,] selected from the group consisting of examples 1, 5, 8, 10, 12, 13, 14, 19, 22, 23, 24, 25 and 27 (shown below):
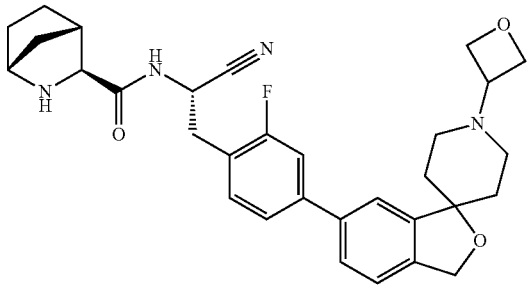
Ex. 1
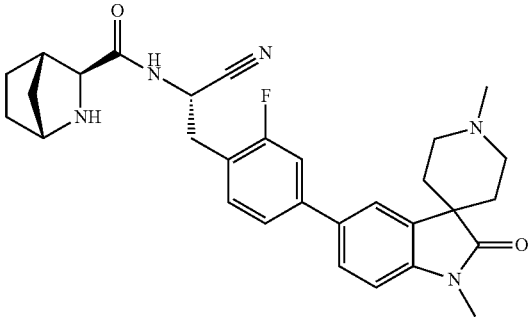
Ex. 5
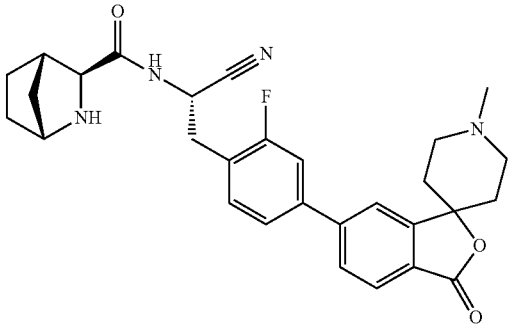
Ex. 8
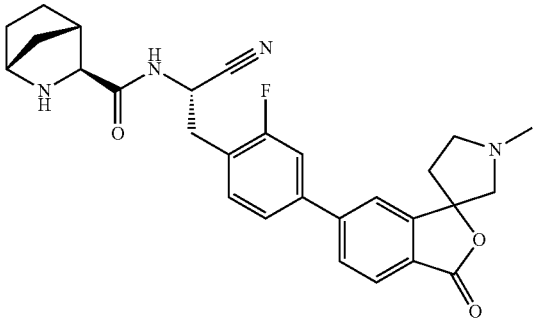
Ex. 10

-continued
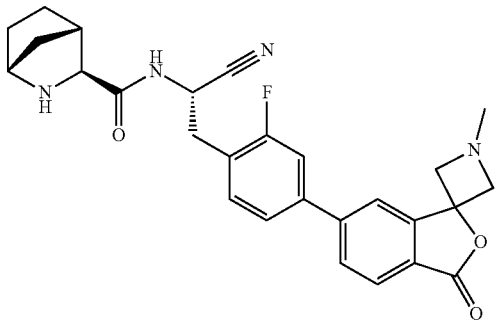
Ex.12
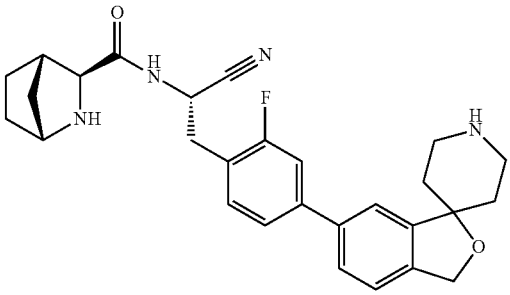
Ex. 13
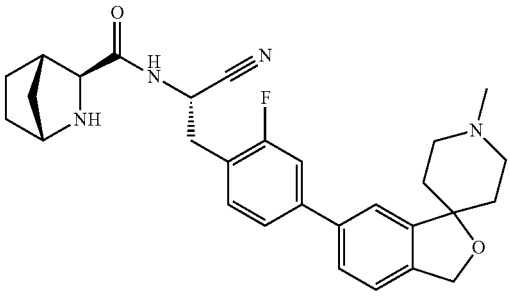
Ex. 14
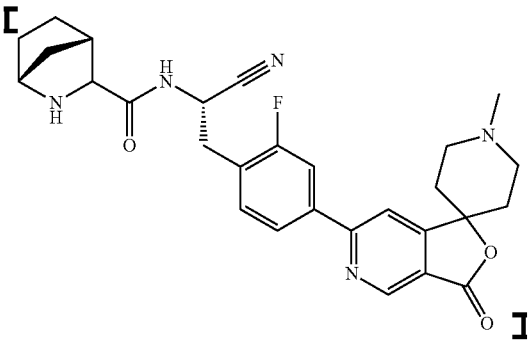
-continued
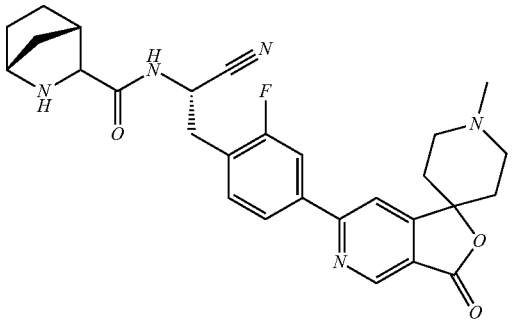
Ex. 19
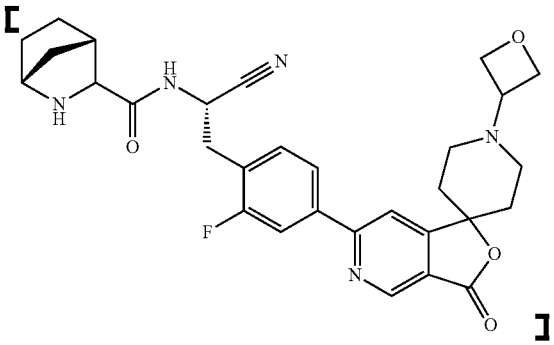
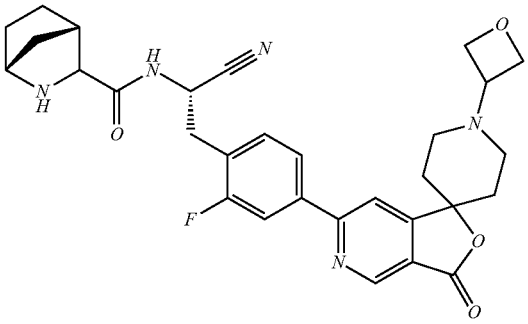
Ex. 22
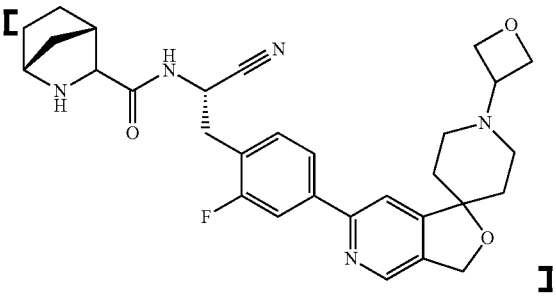

-continued

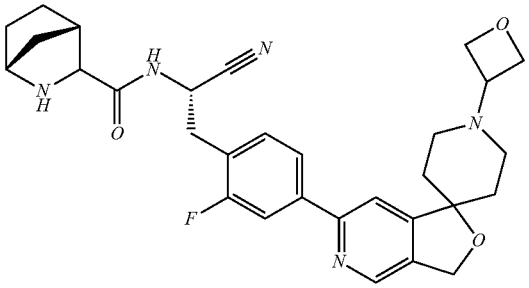

Ex. 23

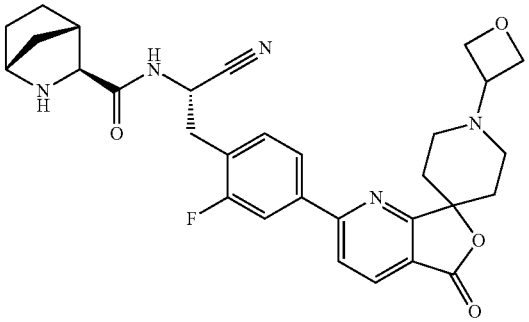

Ex. 24

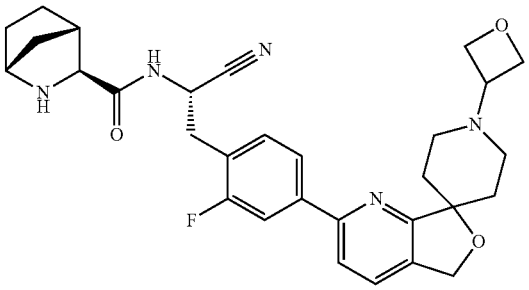

Ex. 25

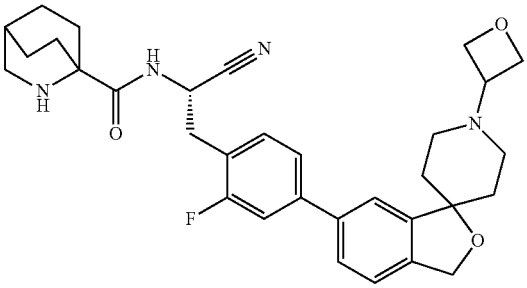

Ex. 27

12. A pharmaceutical composition comprising one or more compounds of formula I according to claim 1 or a pharmaceutically active salt thereof.

13. A pharmaceutical composition comprising one or more compounds of formula I according to claim 1 or a pharmaceutically active salt thereof and a pharmaceutically active compound selected from the group consisting of betamimetics, anticholinergics, corticosteroids, PDE4-inhibitors, LTD4-antagonists, EGFR-inhibitors, CRTH2 inhibitors, 5-LO-inhibitors, Histamine receptor antagonists, CCR9 antagonists [and], SYK-inhibitors, NE-inhibitors, MMP9 inhibitors[,] *and* MMP12 inhibitors.

14. A method of treatment of chronic obstructive pulmonary disease, cystic fibrosis (CF), idiopathic pulmonary fibrosis, bronchiectasis, ANCA-associated vasculitis, emphysema, acute respiratory distress syndrome (ARDS), and Alpha-1-antitrypsin deficiency (A1ATD), comprising administering to the patient a therapeutically effective amount of a compound of formula I according to claim 1 or a pharmaceutically acceptable salt thereof.

15. A compound [of formula I] according to claim 11[.] *having the formula:*

Ex. 1

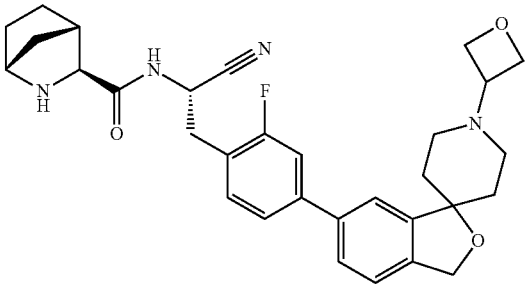

16. A compound of [formula I] according to claim 11[.] *having the formula:*

Ex. 5

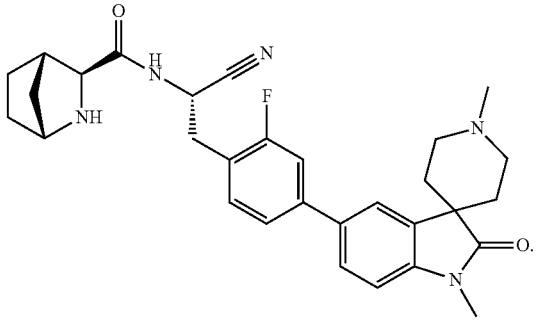

17. A compound [of formula I] according to claim 11[.] *having the formula:*

Ex. 8

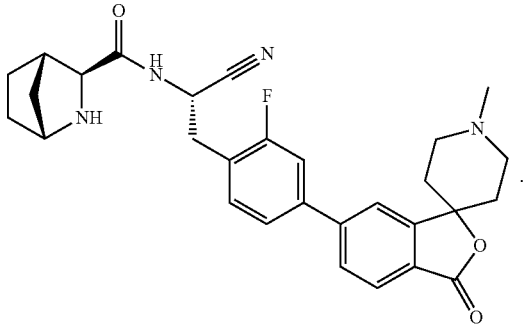

18. A compound [of formula I] according to claim 11[,] *having the formula:*

Ex. 10

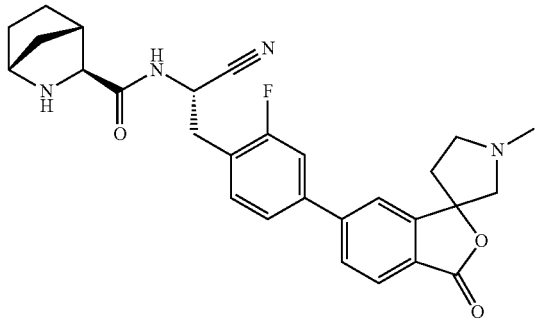

19. A compound [of formula I] according to claim 11[,] *having the formula:*

Ex.12

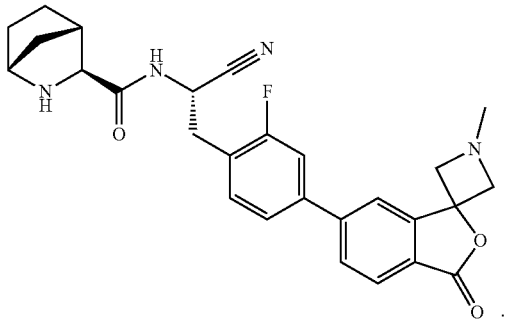

20. A compound [of formula I] according to claim 11[,] *having the formula:*

Ex. 13

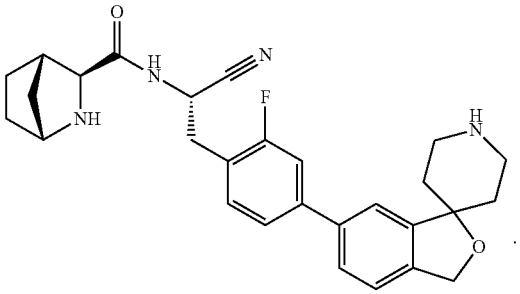

21. A compound [of formula I] according to claim 11[,] *having the formula:*

Ex. 14

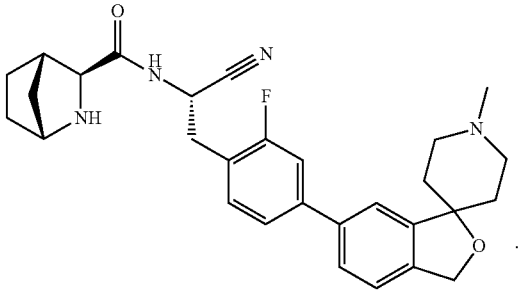

22. A compound [of formula I] according to claim 11[,] *having the formula:*

Ex. 19

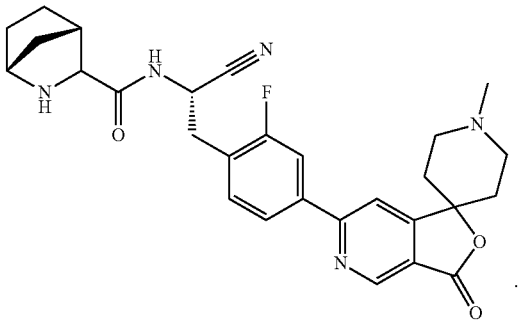

23. A compound [of formula I] according to claim 11[,] *having the formula:*

Ex. 22

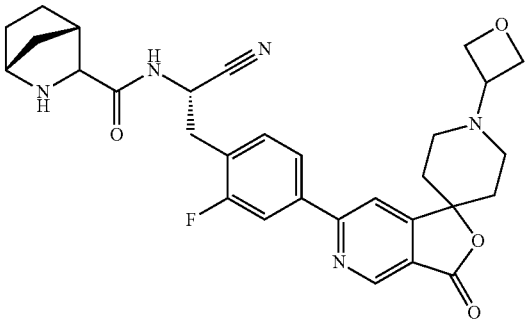

24. A compound [of formula I] according to claim 11[,] *having the formula:*

Ex. 23

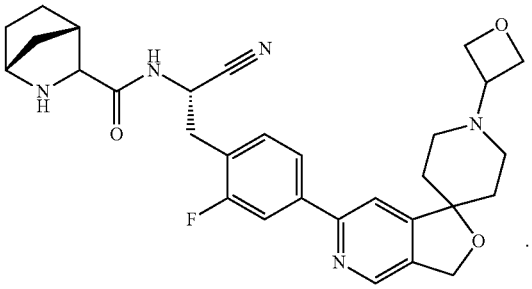

25. A compound [of formula I] according to claim 11[.] *having the formula:*

Ex. 24

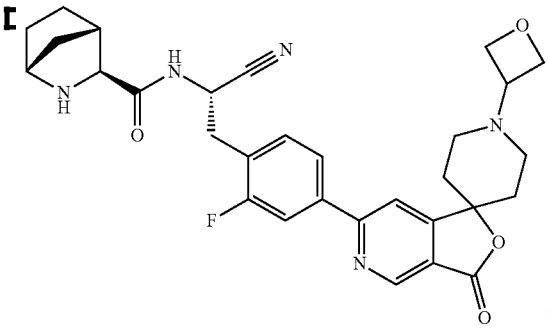

26. A compound [of formula I] according to claim 11[.] *having the formula:*

Ex. 25

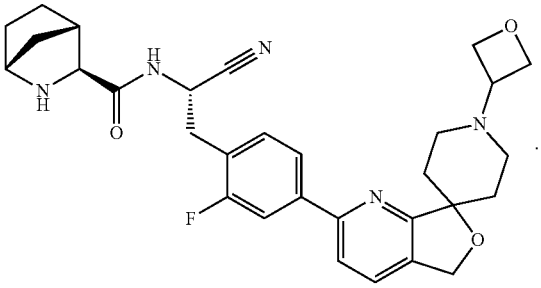

27. A compound [of formula I] according to claim 11[.] *having the formula:*

Ex. 27

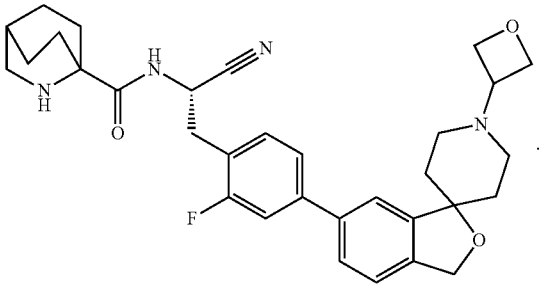

28. A pharmaceutical composition comprising one or more compounds of formula I according to claim 11 or a pharmaceutically active salt thereof.

29. The method of claim 14 wherein the disease is Alpha-1-antitrypsin deficiency (A1ATD).

30. The method of claim 14 wherein the disease is chronic pulmonary obstructive disease and emphysema.

*31. A compound selected from the group consisting of examples 1, 5, 8, 10, 12, 13, 14, 19, 22, 23, 24, 25 and 27 (shown below):*

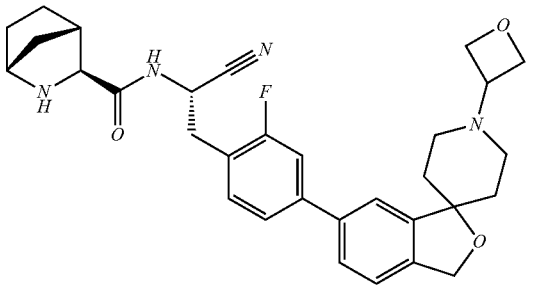

*Ex. 1*

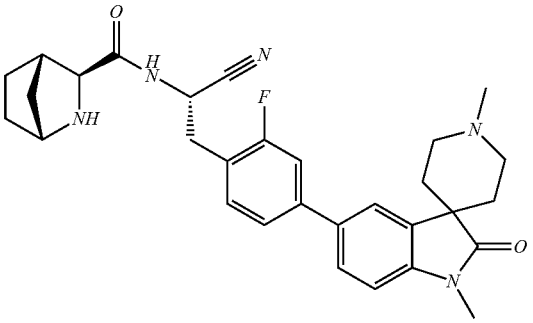

*Ex. 5*

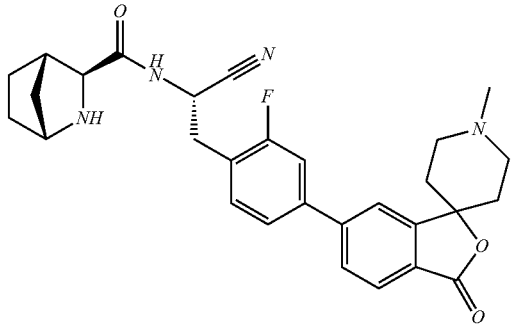
Ex. 8
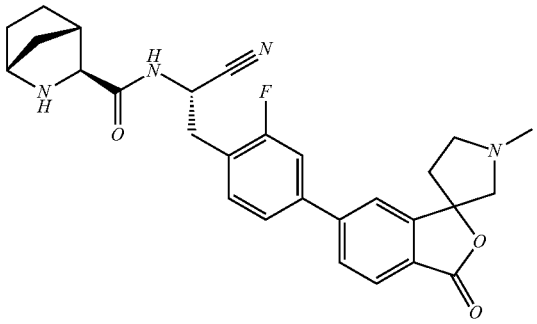
Ex. 10
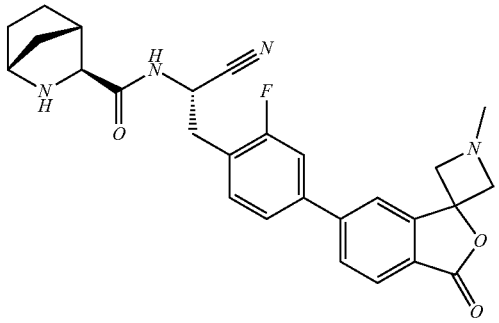
Ex.12
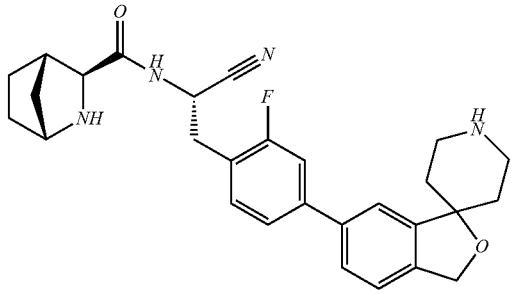
Ex. 13
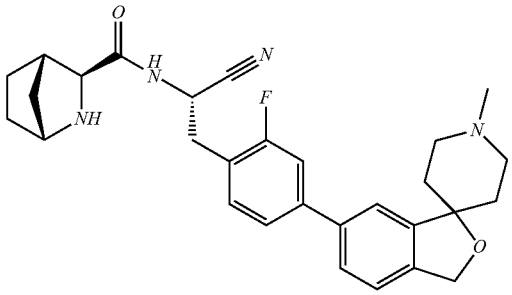
Ex. 14
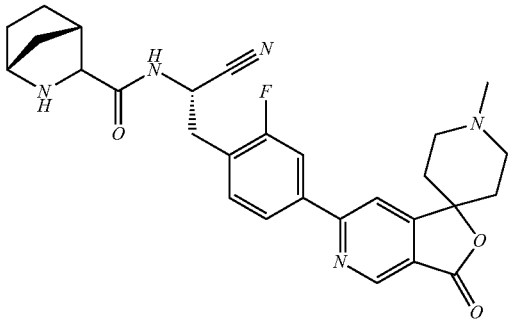
Ex. 19
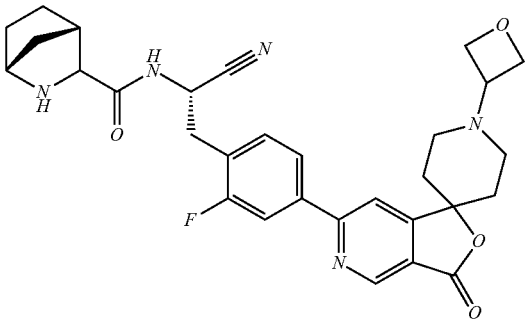
Ex. 22
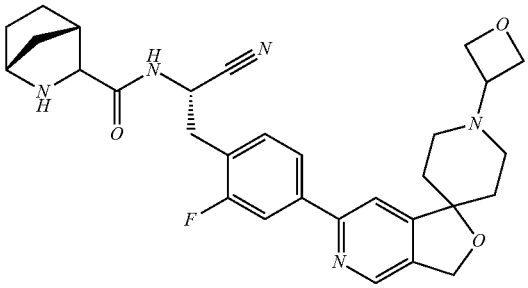
Ex. 23

-continued

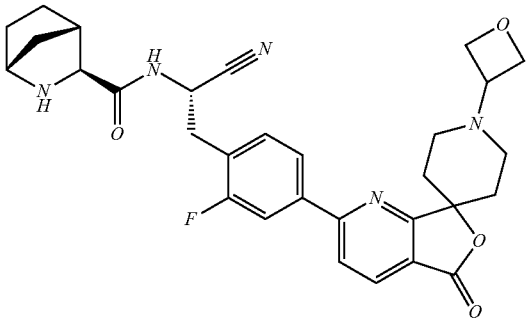

Ex. 24

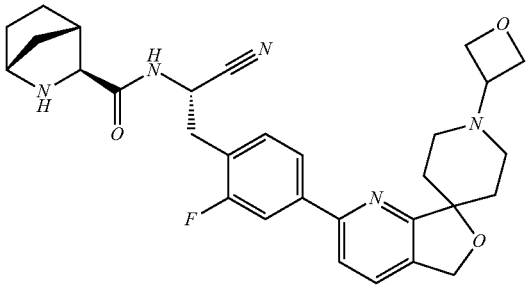

Ex. 25

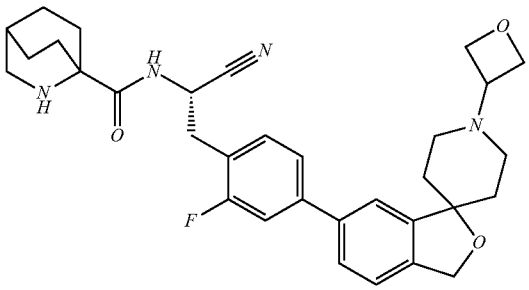

Ex. 27

*or a pharmaceutically acceptable salt thereof.*

*32. A compound or a pharmaceutically acceptable salt thereof according to claim 31 having the formula:*

Ex. 1

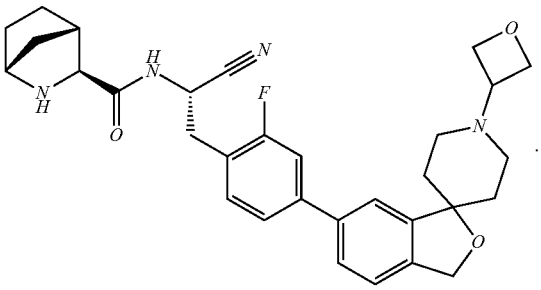

*33. A compound or a pharmaceutically acceptable salt thereof according to claim 31 having the formula:*

Ex. 5

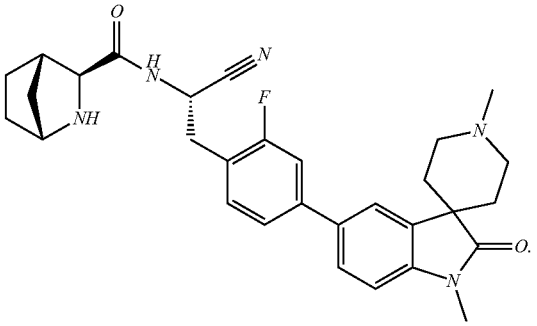

*34. A compound or a pharmaceutically acceptable salt thereof according to claim 31 having the formula:*

Ex. 8

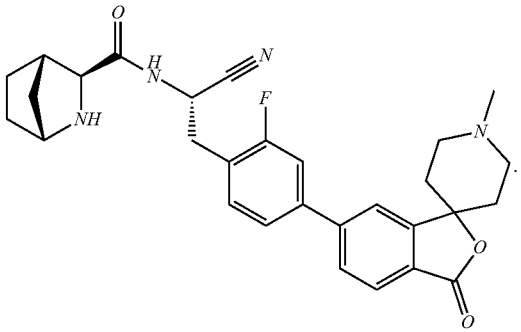

*35. A compound or a pharmaceutically acceptable salt thereof according to claim 31 having the formula:*

Ex. 10

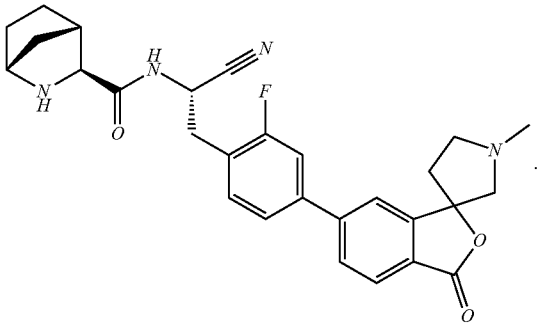

*36. A compound or a pharmaceutically acceptable salt thereof according to claim 31 having the formula:*

Ex. 12

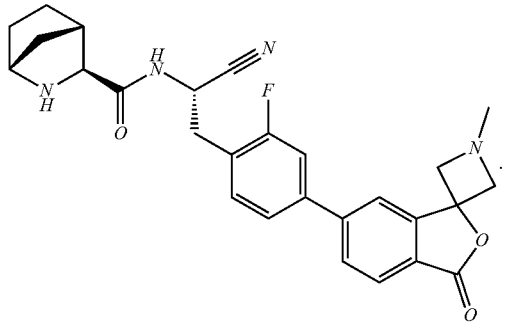

37. A compound or a pharmaceutically acceptable salt thereof according to claim 31 having the formula:

Ex. 13

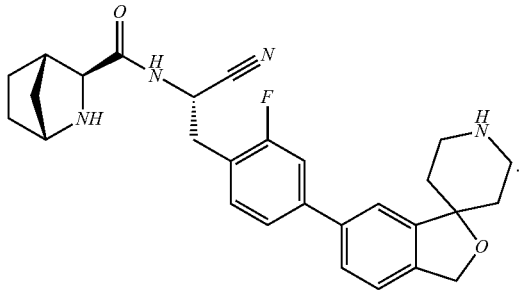

38. A compound or a pharmaceutically acceptable salt thereof according to claim 31 having the formula:

Ex. 14

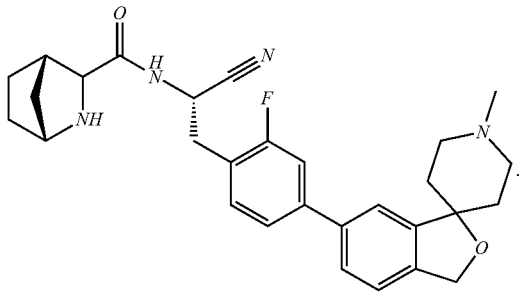

39. A compound or a pharmaceutically acceptable salt thereof according to claim 31 having the formula:

Ex. 19

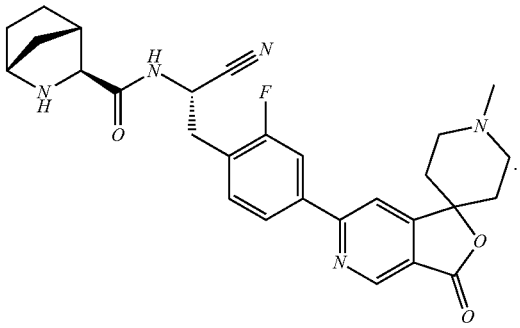

40. A compound or a pharmaceutically acceptable salt thereof according to claim 31 having the formula:

Ex. 22

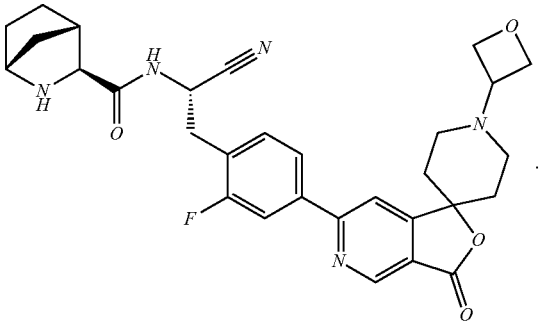

41. A compound or a pharmaceutically acceptable salt thereof according to claim 31 having the formula:

Ex. 23

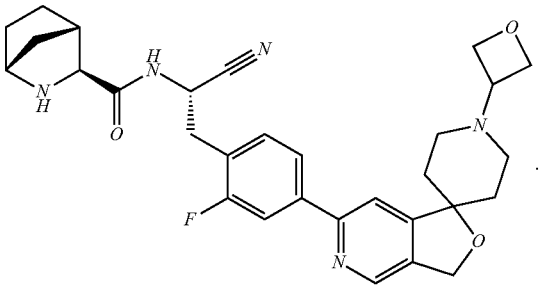

42. A compound or a pharmaceutically acceptable salt thereof according to claim 31 having the formula:

Ex. 24

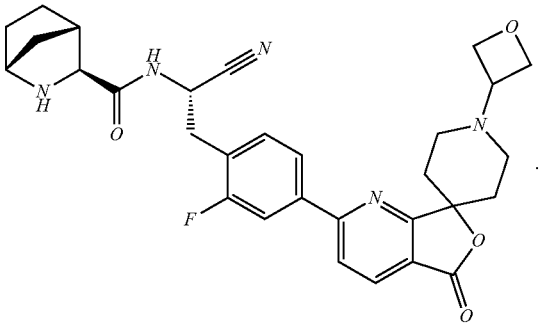

*43. A compound or a pharmaceutically acceptable salt thereof according to claim 31 having the formula:*
*Ex. 25*
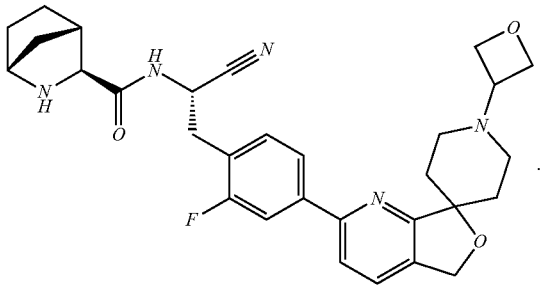
*44. A compound or a pharmaceutically acceptable salt thereof according to claim 31 having the formula:*
*Ex. 27*
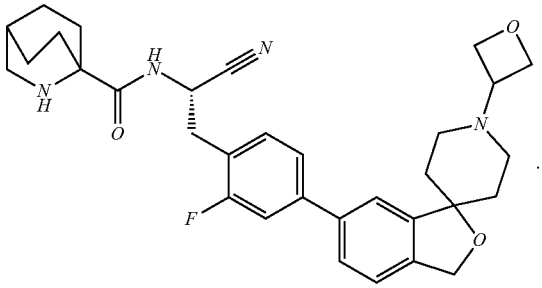
* * * * *